US012773250B2

(12) United States Patent
Darwish et al.

(10) Patent No.: US 12,773,250 B2
(45) Date of Patent: Oct. 27, 2026

(54) DEVICES, SYSTEMS AND METHODS FOR TREATMENT OF LUNG AIRWAYS

(71) Applicant: Galvanize Therapeutics, Inc., Redwood City, CA (US)

(72) Inventors: Asmaa Darwish, San Jose, CA (US); Gil Laroya, Santa Clara, CA (US); Jeff Norton, Redwood City, CA (US); Kevin J. Taylor, San Mateo, CA (US); Paul Brian Friedrichs, Belmont, CA (US); William S. Krimsky, Forest Hill, MD (US)

(73) Assignee: Galvanize Therapeutics, Inc., Redwood City, CA (US)

( * ) Notice: Subject to any disclaimer, the term of this patent is extended or adjusted under 35 U.S.C. 154(b) by 149 days.

(21) Appl. No.: 18/945,229

(22) Filed: Nov. 12, 2024

(65) Prior Publication Data

US 2025/0295442 A1 Sep. 25, 2025

Related U.S. Application Data

(63) Continuation of application No. PCT/US2023/022109, filed on May 12, 2023.

(Continued)

(51) Int. Cl.

*A61B 18/00* (2006.01)
*A61B 1/00* (2006.01)

(Continued)

(52) U.S. Cl.

CPC .......... *A61B 18/00* (2013.01); *A61B 1/00128* (2013.01); *A61B 1/0052* (2013.01);

(Continued)

(58) Field of Classification Search

CPC ... A61B 1/00128; A61B 1/0052; A61B 1/018; A61B 1/2676; A61B 18/00;

(Continued)

(56) References Cited

U.S. PATENT DOCUMENTS

| | | | |
|---|---|---|---|
| 874,178 | A | 12/1907 | Forest |
| 4,249,541 | A | 2/1981 | Pratt |

(Continued)

FOREIGN PATENT DOCUMENTS

| | | | |
|---|---|---|---|
| AT | 306859 | B | 4/1973 |
| AU | 200048007 | | 11/2000 |

(Continued)

OTHER PUBLICATIONS

Appelbaum, Liat et al. US Findings After Irreversible Electroporation Ablation: Radiologic-pathologic Correlation. Radiology 262(1):117-125 (2012).

(Continued)

*Primary Examiner* — Tigist S Demie
(74) *Attorney, Agent, or Firm* — Greenberg Traurig, LLP; Christopher C. Bolten

(57) ABSTRACT

Devices, systems and methods are provided for treating a variety of conditions, such as with pulsed electric field energy, particularly conditions of the lung anatomy. Such treatment typically involves the use of a treatment catheter with access through an endoscope, such as a bronchoscope. Maneuvering the catheter and the endoscope at the same time involves dexterity and coordination, often beyond the ability of one person to achieve without the help of others. In particular, the user is tasked with gross movement of both the catheter and endoscope in relation to the body while at the same time performing fine movement of the catheter in relation to the endoscope and various mechanisms of the catheter and endoscope themselves. Devices, systems and (Continued)

methods are provided to assist the user in performing such tasks solo. Likewise, devices, systems and methods are provided for improved performance of the treatment devices, such as to flush the devices in vivo to remove mucus and other bodily fluids for improved outcomes.

20 Claims, 19 Drawing Sheets

Related U.S. Application Data

(60) Provisional application No. 63/341,937, filed on May 13, 2022.

(51) Int. Cl.
*A61B 1/005* (2006.01)
*A61B 1/018* (2006.01)
*A61B 1/267* (2006.01)

(52) U.S. Cl.
CPC ............ *A61B 1/018* (2013.01); *A61B 1/2676* (2013.01); *A61B 2018/00267* (2013.01); *A61B 2018/00541* (2013.01); *A61B 2018/0091* (2013.01)

(58) Field of Classification Search
CPC ........... A61B 2018/00267; A61B 2018/00541; A61B 2018/0091; A61M 25/0097; A61M 25/02
See application file for complete search history.

(56) References Cited

U.S. PATENT DOCUMENTS 4,822,470 A 4/1989 Chang
5,232,856 A 8/1993 Firth
5,304,120 A 4/1994 Crandell et al.
5,386,837 A 2/1995 Sterzer
5,507,724 A 4/1996 Hofmann et al.
5,601,588 A 2/1997 Tonomura et al.
5,683,384 A 11/1997 Gough et al.
5,704,908 A 1/1998 Hofmann et al.
5,833,710 A 11/1998 Jacobson
5,906,609 A 5/1999 Assa et al.
5,972,026 A 10/1999 Laufer et al.
6,009,347 A 12/1999 Hofmann
6,038,478 A 3/2000 Yuen et al.
6,041,252 A 3/2000 Walker et al.
6,078,490 A 6/2000 Walters
6,083,255 A 7/2000 Laufer et al.
6,107,699 A 8/2000 Swanson
6,120,493 A 9/2000 Hofmann
6,200,333 B1 3/2001 Laufer
6,219,577 B1 4/2001 Brown et al.
6,233,482 B1 5/2001 Hofmann et al.
6,248,056 B1 6/2001 Persson
6,261,831 B1 7/2001 Agee
6,273,907 B1 8/2001 Laufer
6,283,988 B1 9/2001 Laufer et al.
6,283,989 B1 9/2001 Laufer et al.
6,299,633 B1 10/2001 Laufer
6,326,177 B1 12/2001 Schoenbach et al.
6,366,808 B1 4/2002 Schroeppel et al.
6,411,852 B1 6/2002 Danek et al.
6,488,673 B1 12/2002 Laufer et al.
6,520,950 B1 2/2003 Hofmann et al.
6,569,149 B2 5/2003 Dev et al.
6,634,363 B1 10/2003 Danek et al.
6,678,558 B1 1/2004 Dimmer et al.
6,697,670 B2 2/2004 Chomenky et al.
6,733,485 B1 5/2004 Whitehurst et al.
6,738,663 B2 5/2004 Schroeppel et al.
6,770,070 B1 8/2004 Balbierz
6,795,728 B2 9/2004 Chornenky et al.
6,892,099 B2 5/2005 Jaafar et al.
6,994,706 B2 2/2006 Chornenky et al.
7,027,869 B2 4/2006 Danek et al.
7,054,685 B2 5/2006 Dimmer et al.
7,104,987 B2 9/2006 Biggs et al.
7,130,697 B2 10/2006 Chornenky et al.
7,171,263 B2 1/2007 Darvish
7,198,635 B2 4/2007 Danek et al.
7,200,445 B1 4/2007 Dalbec et al.
7,211,083 B2 5/2007 Chornenky et al.
7,255,693 B1 8/2007 Johnston et al.
7,264,002 B2 9/2007 Danek et al.
7,273,055 B2 9/2007 Danek et al.
7,344,533 B2 3/2008 Pearson et al.
7,395,112 B2 7/2008 Keisari et al.
7,412,284 B2 8/2008 Hofmann
7,412,285 B2 8/2008 Schroeppel et al.
7,425,212 B1 9/2008 Danek et al.
7,445,618 B2 11/2008 Eggers et al.
7,542,802 B2 6/2009 Danek et al.
7,556,624 B2 7/2009 Laufer et al.
7,565,205 B2 7/2009 Palti
7,565,206 B2 7/2009 Palti
7,594,925 B2 9/2009 Danek et al.
7,599,745 B2 10/2009 Palti
7,599,746 B2 10/2009 Palti
7,620,451 B2 11/2009 Demarais et al.
7,655,004 B2 2/2010 Long
7,680,543 B2 3/2010 Azure
7,708,768 B2 5/2010 Danek et al.
7,713,740 B2 5/2010 Jaroszeski et al.
7,722,606 B2 5/2010 Azure
7,740,017 B2 6/2010 Danek et al.
7,742,811 B2 6/2010 Schroeppel et al.
7,756,583 B2 7/2010 Demarais et al.
7,765,010 B2 7/2010 Chornenky et al.
7,770,584 B2 8/2010 Danek et al.
7,805,201 B2 9/2010 Palti
7,819,908 B2 10/2010 Ingenito
7,824,870 B2 11/2010 Kovalcheck et al.
7,837,679 B2 11/2010 Biggs et al.
RE42,016 E 12/2010 Chornenky et al.
7,853,331 B2 12/2010 Kaplan et al.
7,853,333 B2 12/2010 Demarais
7,854,734 B2 12/2010 Biggs et al.
7,879,610 B1 2/2011 Heller et al.
7,906,124 B2 3/2011 Laufer et al.
7,917,227 B2 3/2011 Palti
RE42,277 E 4/2011 Jaafar et al.
7,921,855 B2 4/2011 Danek et al.
7,931,647 B2 4/2011 Wizeman et al.
7,937,143 B2 5/2011 Demarais et al.
7,938,123 B2 5/2011 Danek et al.
7,938,824 B2 5/2011 Chornenky et al.
7,949,407 B2 5/2011 Kaplan et al.
7,959,628 B2 6/2011 Schaer et al.
7,992,572 B2 8/2011 Danek et al.
8,007,496 B2 8/2011 Rioux et al.
8,014,854 B2 9/2011 Schroeppel et al.
8,019,414 B2 9/2011 Palti
8,024,048 B2 9/2011 Schroeppel et al.
8,026,223 B1 9/2011 Heller et al.
RE42,835 E 10/2011 Chornenky et al.
8,048,067 B2 11/2011 Davalos et al.
RE43,009 E 12/2011 Chornenky et al.
8,105,324 B2 1/2012 Palanker et al.
8,109,926 B2 2/2012 Azure
8,114,070 B2 2/2012 Rubinsky et al.
8,120,207 B2 2/2012 Sanders et al.
8,131,371 B2 3/2012 Demarals et al.
8,145,316 B2 3/2012 Deem et al.
8,145,317 B2 3/2012 Demarais et al.
8,150,519 B2 4/2012 Demarais et al.
8,150,520 B2 4/2012 Demarais et al.
8,161,978 B2 4/2012 Danek et al.
8,181,656 B2 5/2012 Danek et al.
8,221,411 B2 7/2012 Francischelli et al.
8,231,603 B2 7/2012 Hobbs et al.
8,235,983 B2 8/2012 Webster et al.

(56) References Cited

U.S. PATENT DOCUMENTS 8,244,345 B2 8/2012 Palti
8,251,070 B2 8/2012 Danek et al.
8,251,986 B2 8/2012 Chornenky et al.
8,257,413 B2 9/2012 Danek et al.
8,267,094 B2 9/2012 Danek et al.
8,282,631 B2 10/2012 Davalos et al.
8,292,882 B2 10/2012 Danek et al.
8,298,222 B2 10/2012 Rubinsky et al.
8,298,224 B2 10/2012 Danek et al.
8,406,870 B2 3/2013 Palti
8,425,505 B2 4/2013 Long
8,428,710 B2 4/2013 Kuriyama et al.
8,443,810 B2 5/2013 Danek et al.
8,449,538 B2 5/2013 Long
8,459,268 B2 6/2013 Danek et al.
8,464,723 B2 6/2013 Danek et al.
8,465,484 B2 6/2013 Davalos et al.
8,465,486 B2 6/2013 Danek et al.
8,480,667 B2 7/2013 Kaplan et al.
8,500,713 B2 8/2013 Ferek-Petric
8,504,147 B2 8/2013 Deem et al.
8,512,334 B2 8/2013 Nuccitelli et al.
8,521,274 B2 8/2013 Gutsol et al.
8,534,291 B2 9/2013 Danek et al.
8,540,710 B2 9/2013 Johnson et al.
8,562,588 B2 10/2013 Hobbs et al.
8,568,403 B2 10/2013 Soltesz et al.
8,579,888 B2 11/2013 Hoey et al.
8,584,681 B2 11/2013 Danek et al.
8,600,494 B2 12/2013 Schroeppel et al.
8,603,087 B2 12/2013 Rubinsky et al.
8,620,423 B2 12/2013 Demarais et al.
8,632,534 B2 1/2014 Pearson et al.
8,634,929 B2 1/2014 Chornenky et al.
8,636,726 B1 1/2014 Wells et al.
8,640,711 B2 2/2014 Danek et al.
8,647,338 B2 2/2014 Chornenky et al.
8,652,130 B2 2/2014 Kreindel
8,676,309 B2 3/2014 Deem et al.
8,721,632 B2 5/2014 Hoey et al.
8,733,367 B2 5/2014 Danek et al.
8,740,895 B2 6/2014 Mayse et al.
8,753,335 B2 6/2014 Moshe et al.
8,774,922 B2 7/2014 Zarins et al.
8,777,943 B2 7/2014 Mayse et al.
8,802,643 B1 8/2014 Heller et al.
8,814,860 B2 8/2014 Davalos et al.
8,828,945 B2 9/2014 Laufer et al.
8,888,769 B2 11/2014 Biggs et al.
8,903,488 B2 12/2014 Callas et al.
8,906,006 B2 12/2014 Chornenky et al.
8,911,430 B2 12/2014 Hoey et al.
8,911,439 B2 12/2014 Mayse et al.
8,920,413 B2 12/2014 Danek et al.
8,926,606 B2 1/2015 Davalos et al.
8,927,518 B1 1/2015 Heller et al.
8,944,071 B2 2/2015 Loomas et al.
8,968,210 B2 3/2015 Mugan et al.
8,974,417 B2 3/2015 Kimura et al.
8,992,513 B2 3/2015 Delaney
8,992,517 B2 3/2015 Davalos et al.
9,005,189 B2 4/2015 Davalos et al.
9,017,324 B2 4/2015 Mayse et al.
9,027,564 B2 5/2015 Danek et al.
9,033,976 B2 5/2015 Danek et al.
9,037,230 B2 5/2015 Goldfarb et al.
9,078,665 B2 7/2015 Moss et al.
9,095,323 B2 8/2015 Chu et al.
9,101,764 B2 8/2015 Nuccitelli et al.
9,108,052 B2 8/2015 Jarrard
9,125,666 B2 9/2015 Steinke et al.
9,144,449 B2 9/2015 Burr et al.
9,168,373 B2 10/2015 Nuccitelli et al.
9,173,704 B2 11/2015 Hobbs et al.
9,186,128 B2 11/2015 Mugan et al.
9,198,733 B2 12/2015 Neal et al.
9,199,091 B2 12/2015 Danek et al.
9,211,155 B2 12/2015 Fruland et al.
9,242,041 B2 1/2016 Kosik et al.
9,259,235 B2 2/2016 Chierchia et al.
9,265,563 B2 2/2016 Racz et al.
9,272,132 B2 3/2016 Laufer et al.
9,277,957 B2 3/2016 Long et al.
9,283,374 B2 3/2016 Hollett et al.
9,289,606 B2 3/2016 Paul et al.
9,295,516 B2 3/2016 Pearson et al.
9,301,796 B2 4/2016 Burr et al.
9,308,043 B2 4/2016 Zarins et al.
9,308,044 B2 4/2016 Zarins et al.
9,314,620 B2 4/2016 Long et al.
9,327,122 B2 5/2016 Zarins et al.
9,332,973 B2 5/2016 McWeeney et al.
9,339,328 B2 5/2016 Ortiz et al.
9,339,618 B2 5/2016 Deem et al.
9,358,024 B2 6/2016 Danek et al.
9,375,268 B2 6/2016 Long
9,414,881 B2 8/2016 Callas et al.
9,439,726 B2 9/2016 Zarins et al.
9,486,266 B2 11/2016 Soltesz et al.
9,510,888 B2 12/2016 Lalonde
9,526,568 B2 12/2016 Ohri et al.
9,572,619 B2 2/2017 Laufer et al.
9,598,691 B2 3/2017 Davalos
9,610,067 B2 4/2017 Sekikawa
9,610,364 B1 4/2017 Heller et al.
9,629,912 B2 4/2017 Soikum et al.
9,649,153 B2 5/2017 Mayse et al.
9,649,154 B2 5/2017 Mayse et al.
9,655,669 B2 5/2017 Palti et al.
9,656,055 B2 5/2017 Weissberg et al.
9,656,066 B2 5/2017 Nuccitelli et al.
9,668,809 B2 6/2017 Mayse et al.
9,675,406 B2 6/2017 Moss et al.
9,675,412 B2 6/2017 Mayse et al.
9,681,909 B2 6/2017 Bhargav et al.
9,700,368 B2 7/2017 Callas et al.
9,717,552 B2 8/2017 Cosman et al.
9,724,155 B2 8/2017 Nuccitelli et al.
9,788,707 B2 10/2017 Tinkham et al.
9,789,331 B2 10/2017 Danek et al.
9,820,724 B2 11/2017 Mamiya
9,820,797 B2 11/2017 Burr et al.
9,833,617 B2 12/2017 Travers et al.
9,867,648 B2 1/2018 Mulcahey et al.
9,867,652 B2 1/2018 Sano et al.
9,877,708 B2 1/2018 McWeeney et al.
9,888,956 B2 2/2018 Model et al.
9,895,189 B2 2/2018 Pearson
9,931,161 B2 4/2018 Willis
9,931,163 B2 4/2018 Danek et al.
9,943,684 B2 4/2018 Nuccitelli et al.
9,956,391 B2 5/2018 Weissberg et al.
9,974,609 B2 5/2018 Hollett et al.
9,987,081 B1 6/2018 Bowers et al.
9,993,296 B2 6/2018 Ladtkow et al.
9,999,465 B2 6/2018 Long et al.
10,010,666 B2 7/2018 Rubinsky et al.
10,016,232 B1 7/2018 Bowers et al.
D831,199 S 10/2018 Holton et al.
D832,426 S 10/2018 Holton et al.
10,130,423 B1 11/2018 Viswanathan et al.
10,136,943 B1 11/2018 Cosman, Jr. et al.
10,143,512 B2 12/2018 Rubinsky et al.
10,143,759 B1 12/2018 Heller et al.
10,149,714 B2 12/2018 Mayse et al.
10,154,869 B2 12/2018 Onik et al.
10,154,874 B2 12/2018 Davalos et al.
10,166,071 B2 1/2019 Sherman et al.
10,172,673 B2 1/2019 Viswanathan et al.
10,238,447 B2 3/2019 Neal et al.
10,245,105 B2 4/2019 Davalos et al.
10,271,893 B2 4/2019 Stewart et al.
10,292,755 B2 5/2019 Arena et al.
10,322,286 B2 6/2019 Viswanathan et al.

(56) References Cited

U.S. PATENT DOCUMENTS 10,391,125 B2 8/2019 Nuccitelli et al.
10,426,847 B2 10/2019 Pierce et al.
10,448,989 B2 10/2019 Arena et al.
10,471,254 B2 11/2019 Sano et al.
10,499,980 B2 12/2019 Shuman et al.
10,639,098 B2 5/2020 Cosman
10,694,972 B2 6/2020 Davalos et al.
10,702,337 B2 7/2020 Waldstreicher et al.
10,722,322 B2 7/2020 Vazales
10,779,887 B2 9/2020 Deem et al.
10,849,678 B2 12/2020 Onik et al.
10,874,451 B2 12/2020 Athos et al.
10,939,958 B2 3/2021 Waldstreicher et al.
10,945,714 B2 3/2021 Ralph
11,039,819 B2 6/2021 Gonzalez
11,051,871 B2 7/2021 Nuccitelli et al.
11,052,246 B2 7/2021 Stewart et al.
11,065,372 B2 7/2021 Stender et al.
11,071,530 B2 7/2021 Wang et al.
11,167,095 B2 11/2021 Ralph et al.
11,324,543 B2 5/2022 Waldstreicher et al.
11,369,433 B2 6/2022 Waldstreicher et al.
11,382,681 B2 7/2022 Arena et al.
11,471,208 B2 10/2022 Waldstreicher et al.
11,547,851 B2 1/2023 Krimsky et al.
11,638,603 B2 5/2023 Sano et al.
11,696,797 B2 7/2023 Onik
11,723,712 B2 8/2023 Athos et al.
11,737,810 B2 8/2023 Davalos et al.
11,903,690 B2 2/2024 Davalos et al.
11,938,317 B2 3/2024 Krimsky et al.
11,952,568 B2 4/2024 Neal et al.
12,059,197 B2 8/2024 Davalos et al.
12,173,280 B2 12/2024 Neal, II et al.
12,178,496 B2 12/2024 Jauregui Johnston et al.
12,201,349 B2 1/2025 Pearson et al.
12,349,967 B2 7/2025 Waldstreicher et al.
12,403,305 B2 9/2025 Waldstreicher et al.
12,458,434 B2 11/2025 O'Brien et al.
2001/0008016 A1 7/2001 Kotani et al.
2001/0020166 A1 9/2001 Daly et al.
2002/0010491 A1 1/2002 Schoenbach et al.
2002/0022839 A1 2/2002 Stewart et al.
2002/0103483 A1 8/2002 Edwards
2002/0104318 A1 8/2002 Jaafar et al.
2002/0115991 A1 8/2002 Edwards
2002/0188242 A1 12/2002 Wu
2002/0198567 A1 12/2002 Keisari et al.
2003/0170898 A1 9/2003 Gundersen et al.
2003/0199050 A1 10/2003 Mangano et al.
2004/0029240 A1 2/2004 Acker
2004/0044338 A1 3/2004 Lennox et al.
2004/0047855 A1 3/2004 Ingenito
2004/0068296 A1 4/2004 Palti
2004/0102818 A1 5/2004 Hakky et al.
2004/0158288 A1 8/2004 Keisari et al.
2004/0176804 A1 9/2004 Palti
2005/0010270 A1 1/2005 Laufer
2005/0049542 A1 3/2005 Sigg et al.
2005/0096584 A1 5/2005 Ferek-Petric
2005/0096647 A1 5/2005 Steinke et al.
2005/0170510 A1 8/2005 Huang et al.
2005/0171523 A1 8/2005 Rubinsky et al.
2005/0171574 A1 8/2005 Rubinsky et al.
2005/0171575 A1 8/2005 Dev et al.
2005/0177150 A1 8/2005 Amoah et al.
2005/0222646 A1 10/2005 Kroll et al.
2005/0288730 A1 12/2005 Deem et al.
2006/0008808 A1 1/2006 Yang et al.
2006/0162731 A1* 7/2006 Wondka ........... A61B 17/12104
128/207.14
2006/0264752 A1 11/2006 Rubinsky et al.
2006/0269531 A1 11/2006 Beebe et al.
2006/0293725 A1 12/2006 Rubinsky et al.
2006/0293731 A1 12/2006 Rubinsky et al.
2007/0021803 A1 1/2007 Deem et al.
2007/0025919 A1 2/2007 Deem et al.
2007/0083239 A1 4/2007 Demarais et al.
2007/0093802 A1 4/2007 Danek et al.
2007/0106296 A1 5/2007 Laufer et al.
2007/0106348 A1 5/2007 Laufer
2007/0112349 A1 5/2007 Danek et al.
2007/0118184 A1 5/2007 Danek et al.
2007/0118190 A1 5/2007 Danek et al.
2007/0123958 A1 5/2007 Laufer
2007/0129720 A1 6/2007 Demarais et al.
2007/0156135 A1 7/2007 Rubinsky et al.
2007/0191904 A1 8/2007 Libbus et al.
2007/0239213 A1 10/2007 Palti
2008/0015571 A1 1/2008 Rubinsky et al.
2008/0071264 A1 3/2008 Azure
2008/0132884 A1 6/2008 Rubinsky et al.
2008/0132885 A1 6/2008 Rubinsky et al.
2008/0161801 A1 7/2008 Steinke et al.
2008/0195174 A1 8/2008 Walker et al.
2008/0200912 A1 8/2008 Long
2008/0231337 A1 9/2008 Krishnaswamy et al.
2008/0269586 A1 10/2008 Rubinsky et al.
2008/0306570 A1 12/2008 Rezai et al.
2008/0319372 A1 12/2008 Palti et al.
2009/0043301 A1 2/2009 Jarrard et al.
2009/0069797 A1 3/2009 Danek et al.
2009/0118726 A1 5/2009 Auth et al.
2009/0157002 A1 6/2009 Dumot et al.
2009/0192504 A1 7/2009 Askew
2009/0192505 A1 7/2009 Askew et al.
2009/0192508 A1 7/2009 Laufer et al.
2009/0247933 A1 10/2009 Maor et al.
2009/0281477 A1 11/2009 Mikus et al.
2009/0292342 A1 11/2009 Rubinsky et al.
2009/0306644 A1 12/2009 Mayse et al.
2009/0318914 A1 12/2009 Utley et al.
2010/0004623 A1 1/2010 Hamilton, Jr. et al.
2010/0023004 A1 1/2010 Francischelli et al.
2010/0121270 A1 5/2010 Gunday et al.
2010/0130975 A1 5/2010 Long
2010/0147701 A1 6/2010 Field
2010/0152725 A1 6/2010 Pearson et al.
2010/0160906 A1 6/2010 Jarrard
2010/0179530 A1 7/2010 Long et al.
2010/0204688 A1 8/2010 Hoey et al.
2010/0228248 A1 9/2010 Griffin
2010/0240995 A1 9/2010 Nuccitelli et al.
2010/0256628 A1 10/2010 Pearson et al.
2010/0256630 A1 10/2010 Hamilton, Jr. et al.
2010/0261994 A1 10/2010 Davalos et al.
2010/0274236 A1 10/2010 Krimsky
2010/0324616 A1 12/2010 Livnat et al.
2011/0112527 A1 5/2011 Hamilton, Jr. et al.
2011/0118732 A1 5/2011 Rubinsky et al.
2011/0152855 A1 6/2011 Mayse et al.
2011/0166565 A1 7/2011 Wizeman et al.
2011/0190662 A1 8/2011 Mcweeney
2011/0196288 A1 8/2011 Kaplan et al.
2011/0202052 A1 8/2011 Gelbart et al.
2011/0208166 A1 8/2011 Dumot et al.
2011/0288545 A1 11/2011 Beebe et al.
2012/0098351 A1 4/2012 Ross
2012/0109122 A1 5/2012 Arena et al.
2012/0143120 A1 6/2012 Goldfarb et al.
2012/0150172 A1 6/2012 Ortiz et al.
2012/0197243 A1 8/2012 Sherman et al.
2012/0220998 A1 8/2012 Long et al.
2012/0220999 A1 8/2012 Long
2012/0226101 A1 9/2012 Tinkham et al.
2012/0226271 A1 9/2012 Callas et al.
2012/0277741 A1 11/2012 Davalos et al.
2012/0310237 A1 12/2012 Swanson
2012/0315704 A1 12/2012 Beebe et al.
2012/0330299 A1 12/2012 Webster et al.
2012/0330306 A1 12/2012 Long et al.
2013/0006144 A1 1/2013 Clancy et al.
2013/0023873 A1 1/2013 Danek et al.
2013/0030425 A1 1/2013 Stewart et al.

(56) References Cited

U.S. PATENT DOCUMENTS

2013/0030430 A1 1/2013 Stewart et al.
2013/0035747 A1 2/2013 Danek et al.
2013/0184702 A1 7/2013 Neal et al.
2013/0196441 A1 8/2013 Rubinsky et al.
2013/0211402 A1 8/2013 Danek et al.
2013/0218158 A1 8/2013 Danek et al.
2013/0225996 A1 8/2013 Dillard et al.
2013/0226167 A1 8/2013 Kaplan et al.
2013/0253415 A1 9/2013 Sano et al.
2013/0261389 A1 10/2013 Long
2013/0261683 A1 10/2013 Soikum et al.
2014/0018789 A1 1/2014 Kaplan et al.
2014/0018790 A1 1/2014 Kaplan et al.
2014/0025063 A1 1/2014 Kaplan et al.
2014/0039489 A1 2/2014 Davalos et al.
2014/0039491 A1 2/2014 Bakos et al.
2014/0046322 A1 2/2014 Callas et al.
2014/0052126 A1 2/2014 Long et al.
2014/0058294 A1 2/2014 Gross et al.
2014/0066913 A1 3/2014 Sherman
2014/0074078 A1 3/2014 Kumar et al.
2014/0081263 A1 3/2014 Mesallum
2014/0107478 A1 4/2014 Seward et al.
2014/0114378 A1 4/2014 Danek et al.
2014/0121663 A1 5/2014 Pearson et al.
2014/0128949 A1 5/2014 Hollett et al.
2014/0148635 A1 5/2014 Danek et al.
2014/0296844 A1 10/2014 Kevin et al.
2014/0324036 A1 10/2014 Sachs et al.
2014/0324037 A1 10/2014 Hoey et al.
2014/0330332 A1 11/2014 Danek et al.
2014/0341801 A1 11/2014 Laufer et al.
2014/0378964 A1 12/2014 Pearson
2015/0005766 A1 1/2015 Rioux et al.
2015/0025605 A1 1/2015 Kaplan et al.
2015/0038959 A1 2/2015 Biggs et al.
2015/0039059 A1 2/2015 Mokelke et al.
2015/0045788 A1 2/2015 Litscher et al.
2015/0066005 A1 3/2015 Fan et al.
2015/0066108 A1 3/2015 Shi et al.
2015/0080884 A1 3/2015 Zarins et al.
2015/0088120 A1 3/2015 Garcia et al.
2015/0105775 A1 4/2015 Wizeman et al.
2015/0112321 A1 4/2015 Cadouri
2015/0119879 A1 4/2015 Jameson et al.
2015/0141984 A1 5/2015 Loomas et al.
2015/0150618 A1 6/2015 Onik et al.
2015/0164584 A1 6/2015 Davalos et al.
2015/0173943 A1 6/2015 Loomas et al.
2015/0182282 A1 7/2015 Zemel et al.
2015/0182560 A1 7/2015 Calle et al.
2015/0201996 A1 7/2015 Rubinsky et al.
2015/0223879 A1 8/2015 Danek et al.
2015/0230855 A1 8/2015 Chornenky et al.
2015/0258352 A1 9/2015 Lin et al.
2015/0289923 A1 10/2015 Davalos et al.
2015/0305794 A1 10/2015 Danek et al.
2015/0313664 A1 11/2015 Jarrard
2015/0320478 A1 11/2015 Cosman, Jr. et al.
2015/0320479 A1 11/2015 Cosman, Jr. et al.
2015/0320999 A1 11/2015 Nuccitelli et al.
2015/0327944 A1 11/2015 Neal, II et al.
2015/0342669 A1 12/2015 Flanagan et al.
2016/0000499 A1 1/2016 Lennox et al.
2016/0008016 A1 1/2016 Cioanta et al.
2016/0008066 A1 1/2016 Kaplan et al.
2016/0022349 A1 1/2016 Woloszko et al.
2016/0030014 A1 2/2016 McWeeney et al.
2016/0030016 A1 2/2016 McWeeney et al.
2016/0038230 A1 2/2016 Danek et al.
2016/0058493 A1 3/2016 Neal, II et al.
2016/0066977 A1 3/2016 Neal, II et al.
2016/0066990 A1 3/2016 Kaplan et al.
2016/0074091 A1 3/2016 Amoah et al.
2016/0081745 A1 3/2016 Rajagopalan et al.
2016/0113703 A1 4/2016 Danek et al.
2016/0128767 A1 5/2016 Azamian et al.
2016/0166310 A1 6/2016 Stewart et al.
2016/0199131 A1 7/2016 Allison et al.
2016/0206370 A1 7/2016 Fruland et al.
2016/0235974 A1 8/2016 Holochwost et al.
2016/0262601 A1* 9/2016 Viebach ............... A61B 1/0125
2016/0262795 A1 9/2016 Urbanski et al.
2016/0287314 A1 10/2016 Arena et al.
2016/0303293 A1 10/2016 Doyle et al.
2016/0310211 A1 10/2016 Long
2016/0324573 A1 11/2016 Mickelson et al.
2016/0331441 A1 11/2016 Konings
2016/0338758 A9 11/2016 Davalos et al.
2016/0354142 A1 12/2016 Pearson et al.
2016/0354145 A1 12/2016 Stern et al.
2016/0361109 A1 12/2016 Weaver et al.
2016/0367310 A1 12/2016 Onik et al.
2017/0000584 A1 1/2017 Blanco et al.
2017/0035499 A1 2/2017 Stewart et al.
2017/0049513 A1 2/2017 Cosman, Jr. et al.
2017/0065330 A1 3/2017 Mickelsen et al.
2017/0065339 A1 3/2017 Mickelsen
2017/0065340 A1 3/2017 Long
2017/0065343 A1 3/2017 Mickelsen
2017/0087224 A1 3/2017 Quake
2017/0105763 A1 4/2017 Karve et al.
2017/0105793 A1 4/2017 Cao et al.
2017/0117603 A1 4/2017 Kreis et al.
2017/0119465 A1 5/2017 Long et al.
2017/0135723 A1 5/2017 Zarembinski
2017/0156783 A1 6/2017 Mckernon et al.
2017/0188793 A1* 7/2017 Ouyang ............. A61B 1/00066
2017/0189097 A1 7/2017 Viswanathan et al.
2017/0189579 A1 7/2017 Davalos
2017/0215939 A1 8/2017 Palti et al.
2017/0215953 A1 8/2017 Long et al.
2017/0216353 A1 8/2017 Nuccitelli et al.
2017/0216585 A1 8/2017 Goldfarb et al.
2017/0224363 A1 8/2017 Watanabe et al.
2017/0239480 A1 8/2017 Zarins et al.
2017/0246455 A1 8/2017 Athos et al.
2017/0252090 A1 9/2017 Smith et al.
2017/0266283 A1 9/2017 Soikum et al.
2017/0266438 A1 9/2017 Sano et al.
2017/0281934 A1 10/2017 Giladi et al.
2017/0304002 A1 10/2017 Beebe et al.
2017/0311789 A1 11/2017 Mulcahey et al.
2017/0312021 A1 11/2017 Pilcher et al.
2017/0319843 A1 11/2017 Beebe et al.
2017/0319851 A1 11/2017 Athos et al.
2017/0325894 A1 11/2017 Krimsky
2017/0326361 A1 11/2017 Kreis et al.
2017/0333104 A1 11/2017 Forde et al.
2017/0333109 A1 11/2017 Gilbert
2017/0333112 A1 11/2017 Nuccitelli et al.
2017/0360326 A1 12/2017 Davalos et al.
2018/0000895 A1 1/2018 Pierce et al.
2018/0001056 A1 1/2018 Leeflang et al.
2018/0008127 A1 1/2018 Tinkham et al.
2018/0014868 A1 1/2018 O'Connor et al.
2018/0028250 A1 2/2018 O'Connor
2018/0028267 A1 2/2018 Onik et al.
2018/0036058 A1 2/2018 Fan et al.
2018/0042655 A1 2/2018 Burr et al.
2018/0042674 A1 2/2018 Mickelsen
2018/0042675 A1 2/2018 Long
2018/0043153 A1 2/2018 Viswanathan et al.
2018/0064488 A1 3/2018 Long et al.
2018/0071014 A1 3/2018 Neal et al.
2018/0078755 A1 3/2018 Kreis et al.
2018/0085160 A1 3/2018 Viswanathan et al.
2018/0085575 A1 3/2018 Travers et al.
2018/0104486 A1 4/2018 Yoon et al.
2018/0110557 A1 4/2018 Muratori et al.
2018/0110978 A1 4/2018 Beebe et al.
2018/0125565 A1 5/2018 Sano et al.
2018/0132922 A1 5/2018 Neal, II
2018/0153467 A1 6/2018 Lichtenstein et al.

(56) References Cited

U.S. PATENT DOCUMENTS

| | | | |
|---|---|---|---|
| 2018/0153937 A1 | 6/2018 | Nuccitelli et al. | |
| 2018/0154142 A1 | 6/2018 | Guo et al. | |
| 2018/0193082 A1 | 7/2018 | Rubinsky et al. | |
| 2018/0193088 A1 | 7/2018 | Sutton et al. | |
| 2018/0200510 A1 | 7/2018 | Nuccitelli et al. | |
| 2018/0221078 A1 | 8/2018 | Howard et al. | |
| 2018/0263685 A1 | 9/2018 | Onik et al. | |
| 2018/0289954 A1 | 10/2018 | Hebb et al. | |
| 2018/0303543 A1 | 10/2018 | Stewart et al. | |
| 2018/0311497 A1 | 11/2018 | Viswanathan et al. | |
| 2018/0344378 A1 | 12/2018 | Wolf et al. | |
| 2018/0360531 A1 | 12/2018 | Holmes, Jr. et al. | |
| 2019/0022333 A1 | 1/2019 | Baillargeon et al. | |
| 2019/0030328 A1 | 1/2019 | Stewart et al. | |
| 2019/0038895 A1 | 2/2019 | Pianca et al. | |
| 2019/0046791 A1 | 2/2019 | Ebbers et al. | |
| 2019/0059864 A1 | 2/2019 | Gonzalez | |
| 2019/0069950 A1 | 3/2019 | Viswanathan et al. | |
| 2019/0083169 A1 | 3/2019 | Single et al. | |
| 2019/0099214 A1 | 4/2019 | Rubinsky et al. | |
| 2019/0105408 A1 | 4/2019 | Heller et al. | |
| 2019/0117963 A1 | 4/2019 | Travers et al. | |
| 2019/0117969 A1 | 4/2019 | Schmidt et al. | |
| 2019/0126037 A1 | 5/2019 | Ivorra | |
| 2019/0151015 A1 | 5/2019 | Viswanathan et al. | |
| 2019/0160283 A1 | 5/2019 | Nuccitelli et al. | |
| 2019/0201089 A1* | 7/2019 | Waldstreicher .... | A61B 18/1492 |
| 2019/0216899 A1 | 7/2019 | Bright | |
| 2019/0223938 A1 | 7/2019 | Arena et al. | |
| 2019/0223943 A1 | 7/2019 | Forsyth et al. | |
| 2019/0232048 A1 | 8/2019 | Latouche et al. | |
| 2019/0239949 A1 | 8/2019 | Nuccitelli et al. | |
| 2019/0254735 A1 | 8/2019 | Stewart et al. | |
| 2019/0269826 A1 | 9/2019 | Peyman | |
| 2019/0269912 A1 | 9/2019 | Viswanathan et al. | |
| 2019/0275260 A1 | 9/2019 | Ralph et al. | |
| 2019/0282294 A1 | 9/2019 | Davalos et al. | |
| 2019/0299019 A1 | 10/2019 | Chornenky et al. | |
| 2019/0307781 A1 | 10/2019 | Krex et al. | |
| 2019/0328445 A1 | 10/2019 | Sano et al. | |
| 2019/0350971 A1 | 11/2019 | Nuccitelli et al. | |
| 2019/0351224 A1 | 11/2019 | Sano et al. | |
| 2019/0365362 A1 | 12/2019 | Ralph | |
| 2020/0000938 A1 | 1/2020 | Pierce et al. | |
| 2020/0009377 A1 | 1/2020 | Chang et al. | |
| 2020/0016067 A1 | 1/2020 | Gotlib et al. | |
| 2020/0038093 A1 | 2/2020 | Onik | |
| 2020/0046423 A1 | 2/2020 | Viswanathan et al. | |
| 2020/0046967 A1 | 2/2020 | Ivey et al. | |
| 2020/0060754 A1 | 2/2020 | Shuman et al. | |
| 2020/0060755 A1 | 2/2020 | Shuman et al. | |
| 2020/0078047 A1 | 3/2020 | Lambe et al. | |
| 2020/0129228 A1 | 4/2020 | Henkes et al. | |
| 2020/0260987 A1 | 8/2020 | Davalos et al. | |
| 2020/0275973 A1 | 9/2020 | O'Brien et al. | |
| 2020/0298008 A1 | 9/2020 | Asirvatham | |
| 2020/0323583 A1 | 10/2020 | Qiao | |
| 2020/0398048 A1 | 12/2020 | Krimsky et al. | |
| 2021/0022794 A1 | 1/2021 | Viswanathan | |
| 2021/0023362 A1 | 1/2021 | Lorenzo et al. | |
| 2021/0038280 A1 | 2/2021 | Pikramenos | |
| 2021/0052882 A1 | 2/2021 | Wasson et al. | |
| 2021/0085777 A1 | 3/2021 | Steinmetz et al. | |
| 2021/0137410 A1 | 5/2021 | O'Brien et al. | |
| 2021/0146126 A1 | 5/2021 | Waldstreicher et al. | |
| 2021/0161582 A1 | 6/2021 | Byrd et al. | |
| 2021/0236815 A1 | 8/2021 | Waldstreicher et al. | |
| 2021/0236816 A1 | 8/2021 | Waldstreicher et al. | |
| 2021/0315639 A1 | 10/2021 | Manucherhabadi et al. | |
| 2021/0393327 A1 | 12/2021 | Eyster et al. | |
| 2022/0054188 A1 | 2/2022 | Palushi et al. | |
| 2022/0104875 A1 | 4/2022 | Gleiman et al. | |
| 2022/0161027 A1 | 5/2022 | Aycock et al. | |
| 2022/0233237 A1 | 7/2022 | Adams et al. | |
| 2022/0249157 A1 | 8/2022 | Viswanathan et al. | |
| 2022/0330886 A1 | 10/2022 | Varadan et al. | |
| 2022/0387095 A1 | 12/2022 | Neal, II et al. | |
| 2022/0395323 A1 | 12/2022 | Waldstreicher et al. | |
| 2023/0082389 A1 | 3/2023 | Waldstreicher et al. | |
| 2023/0149706 A1 | 5/2023 | Krimsky et al. | |
| 2023/0165629 A1 | 6/2023 | Tehrani et al. | |
| 2023/0172650 A1 | 6/2023 | Castellvi et al. | |
| 2023/0240746 A1 | 8/2023 | Gundert et al. | |
| 2023/0248414 A1 | 8/2023 | Sano et al. | |
| 2023/0405313 A1 | 12/2023 | Pastori et al. | |
| 2024/0032984 A1 | 2/2024 | Castellvi et al. | |
| 2024/0173557 A1 | 5/2024 | Neal, II et al. | |
| 2024/0180878 A1 | 6/2024 | Spera | |
| 2024/0216038 A1 | 7/2024 | Girouard et al. | |
| 2024/0277245 A1 | 8/2024 | Davalos et al. | |
| 2024/0350185 A1 | 10/2024 | O'Brien et al. | |
| 2024/0350187 A1 | 10/2024 | Waldstreicher et al. | |
| 2024/0390672 A1 | 11/2024 | Neal et al. | |
| 2025/0032787 A1 | 1/2025 | Krimsky et al. | |
| 2025/0040985 A1 | 2/2025 | Girouard et al. | |
| 2025/0064510 A1 | 2/2025 | Waldstreicher et al. | |
| 2025/0213299 A1 | 7/2025 | Nafie et al. | |
| 2025/0261991 A1 | 8/2025 | O'Brien et al. | |

FOREIGN PATENT DOCUMENTS

| | | | |
|---|---|---|---|
| AU | 2004235684 | A1 | 1/2005 |
| AU | 2015355241 | A1 | 6/2017 |
| AU | 2016246146 | A1 | 10/2017 |
| AU | 2020200688 | B2 | 7/2021 |
| CA | 2370223 | A1 | 10/2000 |
| CA | 2981867 | A1 | 10/2016 |
| CN | 1867299 | A | 11/2006 |
| CN | 101198287 | A | 6/2008 |
| CN | 101426551 | A | 5/2009 |
| CN | 101553180 | A | 10/2009 |
| CN | 101909649 | A | 12/2010 |
| CN | 102014779 | A | 4/2011 |
| CN | 102105115 | A | 6/2011 |
| CN | 102421386 | A | 4/2012 |
| CN | 102725021 | A | 10/2012 |
| CN | 103027745 | A | 4/2013 |
| CN | 103252016 | A | 8/2013 |
| CN | 103281978 | A | 9/2013 |
| CN | 103313671 | A | 9/2013 |
| CN | 103582463 | A | 2/2014 |
| CN | 103750899 | A | 4/2014 |
| CN | 103781433 | A | 5/2014 |
| CN | 103796603 | A | 5/2014 |
| CN | 104080418 | A | 10/2014 |
| CN | 104363849 | A | 2/2015 |
| CN | 104470454 | A | 3/2015 |
| CN | 104602634 | A | 5/2015 |
| CN | 104602754 | A | 5/2015 |
| CN | 104703557 | A | 6/2015 |
| CN | 105073051 | A | 11/2015 |
| CN | 105939686 | A | 9/2016 |
| CN | 107194119 | A | 9/2017 |
| CN | 107205772 | A | 9/2017 |
| CN | 107921258 | A | 4/2018 |
| CN | 108024803 | A | 5/2018 |
| CN | 108778172 | A | 11/2018 |
| CN | 108778173 | A | 11/2018 |
| CN | 109788979 | A | 5/2019 |
| CN | 110573104 | A | 12/2019 |
| CN | 113558744 | A | 10/2021 |
| CO | 2017010662 | A2 | 3/2018 |
| DE | 60023283 | T2 | 7/2006 |
| DK | 0987989 | T3 | 10/2006 |
| EP | 1173103 | A2 | 1/2002 |
| EP | 0935482 | B1 | 5/2005 |
| EP | 1173103 | B1 | 10/2005 |
| EP | 1804905 | A1 | 7/2007 |
| EP | 1991303 | A2 | 11/2008 |
| EP | 2170198 | A1 | 4/2010 |
| EP | 2317951 | A1 | 5/2011 |
| EP | 2413833 | A1 | 2/2012 |
| EP | 2488251 | A2 | 8/2012 |
| EP | 2642937 | A2 | 10/2013 |

(56) References Cited

FOREIGN PATENT DOCUMENTS

| | | | |
|---|---|---|---|
| EP | 2661236 | A1 | 11/2013 |
| EP | 2736432 | A1 | 6/2014 |
| EP | 2762195 | A2 | 8/2014 |
| EP | 2777579 | A1 | 9/2014 |
| EP | 2170198 | B1 | 4/2015 |
| EP | 1648555 | B1 | 9/2015 |
| EP | 2957248 | A1 | 12/2015 |
| EP | 1804905 | B1 | 2/2016 |
| EP | 2736432 | B1 | 3/2016 |
| EP | 3003461 | A2 | 4/2016 |
| EP | 2661236 | B1 | 8/2016 |
| EP | 3091925 | A1 | 11/2016 |
| EP | 3113605 | A1 | 1/2017 |
| EP | 3142584 | A1 | 3/2017 |
| EP | 3143124 | A1 | 3/2017 |
| EP | 3154464 | A1 | 4/2017 |
| EP | 3003470 | B1 | 8/2017 |
| EP | 3226794 | A1 | 10/2017 |
| EP | 3282953 | A1 | 2/2018 |
| EP | 3290082 | A2 | 3/2018 |
| EP | 3139997 | B1 | 9/2018 |
| EP | 3113605 | B1 | 10/2018 |
| EP | 3399931 | A1 | 11/2018 |
| EP | 3399933 | A1 | 11/2018 |
| EP | 3154463 | B1 | 3/2019 |
| EP | 3471631 | A1 | 4/2019 |
| EP | 2994045 | B1 | 5/2019 |
| EP | 3003461 | B1 | 5/2019 |
| EP | 3091921 | B1 | 6/2019 |
| EP | 3456278 | A3 | 6/2019 |
| EP | 3495018 | A1 | 6/2019 |
| EP | 3206613 | B1 | 7/2019 |
| EP | 3569144 | A1 | 11/2019 |
| ES | 2246853 | T3 | 3/2006 |
| ES | 2361460 | T3 | 6/2011 |
| IN | 200601622 | | 5/2007 |
| JP | H09285182 | A | 10/1997 |
| JP | 2001103741 | A | 4/2001 |
| JP | 2001506157 | A | 5/2001 |
| JP | 2002065626 | A | 3/2002 |
| JP | 2002541905 | A | 12/2002 |
| JP | 2003529401 | A | 10/2003 |
| JP | 2004516867 | A | 6/2004 |
| JP | 2006320176 | A | 11/2006 |
| JP | 2007504910 | A | 3/2007 |
| JP | 4242436 | B2 | 3/2009 |
| JP | 4243436 | B2 | 3/2009 |
| JP | 2010509032 | A | 3/2010 |
| JP | 2011519699 | A | 7/2011 |
| JP | 2011524785 | A | 9/2011 |
| JP | 2012515018 | A | 7/2012 |
| JP | 2013543745 | A | 12/2013 |
| JP | 2015128596 | A | 7/2015 |
| JP | 2015524732 | A | 8/2015 |
| JP | 2016195826 | A | 11/2016 |
| JP | 2017518805 | A | 7/2017 |
| JP | 2017529169 | A | 10/2017 |
| JP | 2019500170 | A | 1/2019 |
| JP | 2019524396 | A | 9/2019 |
| JP | 2020518335 | A | 6/2020 |
| JP | 2021500153 | A | 1/2021 |
| JP | 2023536906 | A | 8/2023 |
| PT | 987989 | E | 11/2006 |
| WO | WO-9814238 | A1 | 4/1998 |
| WO | WO-9906101 | A1 | 2/1999 |
| WO | WO-0062699 | A2 | 10/2000 |
| WO | WO-0110319 | A1 | 2/2001 |
| WO | WO-2001055294 | A1 | 8/2001 |
| WO | WO-0232333 | A1 | 4/2002 |
| WO | WO-02098501 | A2 | 12/2002 |
| WO | WO-03047684 | A2 | 6/2003 |
| WO | WO-2004037341 | A2 | 5/2004 |
| WO | WO-2004110371 | A2 | 12/2004 |
| WO | WO-2005044371 | A1 | 5/2005 |
| WO | WO-2005065284 | A2 | 7/2005 |
| WO | WO-2005065284 | A3 | 11/2005 |
| WO | WO-2005115535 | A2 | 12/2005 |
| WO | WO-2005032646 | A3 | 4/2006 |
| WO | WO-2006036706 | A1 | 4/2006 |
| WO | WO-2006052940 | A2 | 5/2006 |
| WO | WO-2006085150 | A2 | 8/2006 |
| WO | WO-2006116198 | A2 | 11/2006 |
| WO | WO-2006116608 | A2 | 11/2006 |
| WO | WO-2006131816 | A2 | 12/2006 |
| WO | WO-2007001747 | A2 | 1/2007 |
| WO | WO-2007001751 | A1 | 1/2007 |
| WO | WO-2007039799 | A3 | 7/2007 |
| WO | WO-2007100727 | A2 | 9/2007 |
| WO | WO-2007103070 | A2 | 9/2007 |
| WO | WO-2008034100 | A2 | 3/2008 |
| WO | WO-2008063195 | A1 | 5/2008 |
| WO | WO-2008087489 | A2 | 7/2008 |
| WO | WO-2009009398 | A1 | 1/2009 |
| WO | WO-2009137800 | A2 | 11/2009 |
| WO | WO-2009137819 | A1 | 11/2009 |
| WO | WO-2009154654 | A1 | 12/2009 |
| WO | WO-2010014480 | A1 | 2/2010 |
| WO | WO-2010022275 | A1 | 2/2010 |
| WO | WO-2010080974 | A1 | 7/2010 |
| WO | WO-2010093692 | A2 | 8/2010 |
| WO | WO-2010107947 | A1 | 9/2010 |
| WO | WO-2010117806 | A1 | 10/2010 |
| WO | WO-2010118387 | A1 | 10/2010 |
| WO | WO-2010141417 | A2 | 12/2010 |
| WO | WO-2010151277 | A1 | 12/2010 |
| WO | WO-2011047387 | A2 | 4/2011 |
| WO | WO-2011135294 | A1 | 11/2011 |
| WO | WO-2012071526 | A2 | 5/2012 |
| WO | WO-2012088149 | A2 | 6/2012 |
| WO | WO-2012118659 | A1 | 9/2012 |
| WO | WO-2013052501 | A1 | 4/2013 |
| WO | WO-2014025394 | A1 | 2/2014 |
| WO | WO-2014105964 | A1 | 7/2014 |
| WO | WO-2014181167 | A1 | 11/2014 |
| WO | WO-2014197240 | A2 | 12/2014 |
| WO | WO-2014197632 | A2 | 12/2014 |
| WO | WO-2014204978 | A1 | 12/2014 |
| WO | WO-2015085162 | A1 | 6/2015 |
| WO | WO-2015103530 | A1 | 7/2015 |
| WO | WO-2015103574 | A1 | 7/2015 |
| WO | WO-2015171921 | A2 | 11/2015 |
| WO | WO-2015175570 | A1 | 11/2015 |
| WO | WO-2015192018 | A1 | 12/2015 |
| WO | WO-2015192027 | A1 | 12/2015 |
| WO | WO-2016014264 | A1 | 1/2016 |
| WO | WO-2016036891 | A1 | 3/2016 |
| WO | WO-2016060983 | A1 | 4/2016 |
| WO | WO-2016061002 | A1 | 4/2016 |
| WO | WO-2016089781 | A1 | 6/2016 |
| WO | WO-2016100325 | A1 | 6/2016 |
| WO | WO-2016112359 | A1 | 7/2016 |
| WO | WO-2016123608 | A2 | 8/2016 |
| WO | WO-2016126778 | A1 | 8/2016 |
| WO | WO-2016149575 | A1 | 9/2016 |
| WO | WO-2016154473 | A1 | 9/2016 |
| WO | WO-2016164930 | A1 | 10/2016 |
| WO | WO-2016178697 | A1 | 11/2016 |
| WO | WO-2016179712 | A1 | 11/2016 |
| WO | WO-2016180934 | A1 | 11/2016 |
| WO | WO-2016201264 | A1 | 12/2016 |
| WO | WO-2017024123 | A1 | 2/2017 |
| WO | WO-2017109261 | A1 | 6/2017 |
| WO | WO-2017114001 | A1 | 7/2017 |
| WO | WO-2017119934 | A1 | 7/2017 |
| WO | WO-2017120169 | A1 | 7/2017 |
| WO | WO-2017151260 | A1 | 9/2017 |
| WO | WO-2017173089 | A1 | 10/2017 |
| WO | WO-2017175116 | A1 | 10/2017 |
| WO | WO-2017200954 | A1 | 11/2017 |
| WO | WO-2017201394 | A1 | 11/2017 |
| WO | WO-2017218734 | A1 | 12/2017 |
| WO | WO-2018005511 | A1 | 1/2018 |
| WO | WO-2018010659 | A1 | 1/2018 |
| WO | WO-2018026985 | A1 | 2/2018 |

(56) References Cited

FOREIGN PATENT DOCUMENTS

| | | | |
|---|---|---|---|
| WO | WO-2018065806 | A1 | 4/2018 |
| WO | WO-2018067999 | A1 | 4/2018 |
| WO | WO-2018075946 | A1 | 4/2018 |
| WO | WO-2018106672 | A1 | 6/2018 |
| WO | WO-2018187244 | A2 | 10/2018 |
| WO | WO-2018200800 | A1 | 11/2018 |
| WO | WO-2018201037 | A1 | 11/2018 |
| WO | WO-2019032474 | A1 | 2/2019 |
| WO | WO-2019055512 | A1 | 3/2019 |
| WO | WO-2019084011 | A1 | 5/2019 |
| WO | WO-2019095604 | A1 | 5/2019 |
| WO | WO-2019100016 | A1 | 5/2019 |
| WO | WO-2019108540 | A1 | 6/2019 |
| WO | WO-2019133606 | A1 | 7/2019 |
| WO | WO-2019133608 | A1 | 7/2019 |
| WO | WO-2019157359 | A1 | 8/2019 |
| WO | WO-2019178500 | A1 | 9/2019 |
| WO | WO-2019197973 | A1 | 10/2019 |
| WO | WO-2020005186 | A2 | 1/2020 |
| WO | WO-2020010188 | A1 | 1/2020 |
| WO | WO-2020018662 | A1 | 1/2020 |
| WO | WO-2020061192 | A1 | 3/2020 |
| WO | WO-2020118383 | A1 | 6/2020 |
| WO | WO-2020150709 | A1 | 7/2020 |
| WO | WO-2020215007 | A1 | 10/2020 |
| WO | WO-2021011733 | A1 | 1/2021 |
| WO | WO-2021108292 | A1 | 6/2021 |
| WO | WO-2021127558 | A1 | 6/2021 |
| WO | WO-2021207385 | A1 | 10/2021 |
| WO | WO-2022031797 | A1 | 2/2022 |
| WO | WO-2022204479 | A1 | 9/2022 |
| WO | WO-2022260723 | A1 | 12/2022 |
| WO | WO-2022261418 | A1 | 12/2022 |
| WO | WO-2023044124 | A1 | 3/2023 |
| WO | WO-2023172773 | A1 | 9/2023 |
| WO | WO-2023212250 | A1 | 11/2023 |
| WO | WO-2023220419 | A1 | 11/2023 |
| WO | WO-2024196823 | A2 | 9/2024 |
| WO | WO-2024254966 | A1 | 12/2024 |
| WO | WO-2025043024 | A2 | 2/2025 |
| WO | WO-2025081663 | A1 | 4/2025 |
| WO | WO-2025235871 | A1 | 11/2025 |

OTHER PUBLICATIONS

Arena, Christopher B et al. High-frequency Irreversible Electroporation (H-FIRE) for Non-thermal Ablation Without Muscle Contraction. Biomedical Engineering Online 10:102, 1-21 (2011).

Cerveri, I. et al. Variations in the Prevalence Across Countries of Chronic Bronchitis and Smoking Habits in Young Adults. The European Respiratory Journal 18(1):85-92 (2001).

Charalambous, Pabos et al. The Efficacy and Safety of the Open Approach Irreversible Electroporation in the Treatment of Pancreatic Cancer: A Systematic Review. European Journal of Surgical Oncology : The Journal of the European Society of Surgical Oncology and the British Association of Surgical Oncology 46(9): 1565-1572 (2020).

Cheetham, Jon et al. Effects of Functional Electrical Stimulation on Denervated Laryngeal Muscle in a Large Animal Model. Artificial Organs 39(10):876-885 (2015).

Co-pending U.S. Appl. No. 09/095,323, inventor Laufer; Michael D., filed Jun. 10, 1998.

Co-pending U.S. Appl. No. 19/197,872, inventors Krimsky; William Sanford et al., filed May 2, 2025.

Co-pending U.S. Appl. No. 19/224,643, inventors Waldstreicher; Jonathan Reuben et al., filed May 30, 2025.

Criner, Gerard. Chronic Bronchitis: The Case for an Unmet Medical Need. ERS (2017).

Davalos, Rafael V. et al. Implications and Considerations of Thermal Effects When Applying Irreversible Electroporation Tissue Ablation Therapy. The Prostate 75(10): 1114-1118 (2015).

Dean, David A. Chapter 15 Gene Electrotransfer to Lung. Springer Science+Business Media, LLC :165-175 (2011).

Dupuy, Damian E. et al. Irreversible Electroporation in a Swine Lung Model. Cardiovascular and Interventional Radiology 34(2):391-395 (2011).

Edd, Jon F. et al. In vivo results of a new focal tissue ablation technique: irreversible electroporation. IEEE Transactions on Biomedical Engineering 53(7):1409-1415 (2006).

EP20792123.0 Extended European Search Report dated Dec. 21, 2022.

EP21785398.5 Extended European Search Report dated Apr. 4, 2024.

EP22210537.1 Extended European Search Report dated Apr. 26, 2023.

EP22776703.5 Extended European Search Report dated Dec. 23, 2024.

EP23174654.6 Extended European Search Report dated Jun. 23, 2023.

EP23178276.4 Extended European Search Report dated Jun. 26, 2023.

EP25166670.7 Extended European Search Report dated May 15, 2025.

FastStats—Chronic Lower Respiratory Disease. Centers for Disease Control and Prevention (CDC) / National Center for Health Statistics (NCHS). Jan. 16, 2021; [retrieved on Feb. 4, 2021]. Available at URL: https://www.cdc.gov/nchs/fastats/copd.htm pp. 1-2.

Fernandez-Bussy, S. et al. Histopathologic results post bronchial rheoplasty. D94. Copd: Epidemiology and Therapy. American Thoracic Society 199:A7043 (2019). (Abstract Only).

Fernandez-Bussy, Sebastian et al. Histopathologic Results Post Bronchial Rheoplasty. American Thoracic Society (2019).

Frandsen, Stine Krog et al. Calcium electroporation in three cell lines: a comparison of bleomycin and calcium, calcium compounds, and pulsing conditions. Biochimica et Biophysica Acta (BBA)—General Subjects 1840(3):1204-1208 (2014).

Global Strategy for the Diagnosis, Management, and Prevention of COPD. Global Initiative for Chronic Obstructive Lung Disease : 1-42 (2017).

Health at a Glance: Europe (2012 and 2014 reports). OECD, Available at URL: https://www.oecd.org/en/publications/health-at-a-glance-europe-2012_9789264183896-en.html ; https://www.oecd.org/en/publications/health-at-a-glance-europe-2014_health_glance_eur-2014-en.html.

Kim, Hong Bae et al. Physicochemical Factors That Affect Electroporation of Lung Cancer and Normal Cell Lines. Biochemical and Biophysical Research Communications 517(4):703-708 (2019).

Kim, Victor et al. Bronchial rheoplasty increases distal airway volume in chronic bronchitis. European Respiratory Journal 54(suppl 63): PA2040, (2019). (Abstract Only).

Kim, Victor et al. The Chronic Bronchitic Phenotype of COPD: An Analysis of the COPDGene Study. Chest 140(3):626-633 (2011).

Kundalia, Kaushal et al. Margin ACcentuation for resectable Pancreatic cancer using Irreversible Electroporation-Results from the MACPIE-I study. European Journal of Surgical Oncology 47(10):2571-2578 (2021).

Lu, Jiamiao et al. Sequence-modified antibiotic resistance genes provide sustained plasmid-mediated transgene expression in mammals. Molecular Therapy 25(5):1187-1198 (2017).

Maor, Elad et al. Irreversible electroporation attenuates neointimal formation after angioplasty. IEEE Transactions on Biomedical Engineering 55(9):2268-2274 (2008).

Maor, Elad et al. The effect of irreversible electroporation on blood vessels. Technology in cancer research and treatment 6(4):307-312 (2007).

Miklovic, Tyler et al. A comprehensive characterization of parameters affecting high-frequency irreversible electroporation lesions. Annals of biomedical engineering 45:2524-2534 (2017).

Novickij, Vitalij et al. High Frequency Electroporation Efficiency is Under Control of Membrane Capacitive Charging and Voltage Potential Relaxation. Bioelectrochemistry 119:92-97 (2018).

PCT/US2017/039527 International Search Report and Written Opinion dated Dec. 7, 2017.

(56) References Cited

OTHER PUBLICATIONS

PCT/US2018/067501 International Search Report and Written Opinion dated Mar. 13, 2019.
PCT/US2018/067504 International Search Report and Written Opinion dated Mar. 13, 2019.
PCT/US2020/028844 International Search Report and Written Opinion dated Sep. 4, 2020.
PCT/US2021/026221 International Search Report and Written Opinion dated Jul. 21, 2021.
PCT/US2022/021888 International Search Report and Written Opinion dated Jun. 16, 2022.
PCT/US2023/022109 International Search Report and Written Opinion dated Aug. 15, 2023.
Reddy, Vivek Y. et al. Pulsed field ablation of paroxysmal atrial fibrillation: 1-year outcomes of Impulse, Pefcat, and Pefcat II. Clinical Electrophysiology 7(5):614-627 (2021).
Ricke, Jens. et al. Irreversible Electroporation (IRE) Fails to Demonstrate Efficacy in a Prospective Multicenter Phase II Trial on Lung Malignancies: The ALICE Trial. Cardiovascular and Interventional Radiology 38(2):401-408 (2015).
Rubinsky, Boris et al. Irreversible electroporation: a new ablation modality—clinical implications. Technology in cancer research & treatment 6(1):37-48 (2007).
Sano, Michael B. et al. Burst and continuous high frequency irreversible electroporation protocols evaluated in a 3D tumor model. Physics in Medicine and Biology 63(13): 135022, 1-18 (2018).
Shah, Pallav L, and Christopher Orton. Epithelial Resurfacing: The Bronchial Skin Peel. American Journal of Respiratory and Critical Care Medicine 202(5):641-642 (2020).
Tang, Peter S. et al. Acute Lung Injury and Cell Death: How Many Ways Can Cells Die ?. American Journal of Physiology. Lung Cellular and Molecular Physiology 294(4): L632-L641 (2008).
Timmer, Florentine EF. et al. Irreversible electroporation for locally advanced pancreatic cancer. Techniques in vascular and interventional radiology 23(2): 100675, 1-9 (2020).
Tri, Jason A et al. Electroporation ablation of bronchial smooth muscle cells: A novel non-thermal asthma therapy. Pulmonary and critical care medicine 1(4):1-4 (2016).
U.S. Appl. No. 16/227,796 Notice of Allowance dated Feb. 24, 2022.
U.S. Appl. No. 16/227,796 Notice of Allowance dated Mar. 24, 2022.
U.S. Appl. No. 16/227,796 Office Action dated May 20, 2021.
U.S. Appl. No. 16/227,796 Office Action dated Nov. 10, 2021.
U.S. Appl. No. 16/381,745 Notice of Allowance dated Feb. 25, 2020.
U.S. Appl. No. 16/381,745 Office Action dated Aug. 19, 2019.
U.S. Appl. No. 16/898,320 Notice of Allowance dated Nov. 3, 2020.
U.S. Appl. No. 16/898,320 Office Action dated Jul. 24, 2020.
U.S. Appl. No. 16/914,072 Notice of Allowance dated Jun. 20, 2022.
U.S. Appl. No. 16/914,072 Office Action dated Nov. 26, 2021.
U.S. Appl. No. 16/914,200 Notice of Allowance dated Sep. 8, 2022.
U.S. Appl. No. 16/914,200 Office Action dated May 4, 2022.
U.S. Appl. No. 16/914,200 Office Action dated Oct. 22, 2021.
U.S. Appl. No. 17/212,833 Notice of Allowance dated May 6, 2025.
U.S. Appl. No. 17/212,833 Office Action dated Sep. 6, 2024.
U.S. Appl. No. 17/214,688 Notice of Allowance dated Feb. 4, 2022.
U.S. Appl. No. 17/214,688 Notice of Allowance dated Mar. 2, 2022.
U.S. Appl. No. 17/214,688 Office Action dated May 25, 2021.
U.S. Appl. No. 17/214,688 Office Action dated Sep. 7, 2021.
U.S. Appl. No. 17/502,640 Notice of Allowance dated Sep. 26, 2024.
U.S. Appl. No. 17/502,640 Office Action dated Apr. 28, 2023.
U.S. Appl. No. 17/502,640 Office Action dated Jul. 13, 2022.
U.S. Appl. No. 17/502,640 Office Action dated Mar. 14, 2022.
U.S. Appl. No. 17/502,640 Office Action dated Nov. 27, 2023.
U.S. Appl. No. 17/502,640 Supplemental Notice of Allowability dated Dec. 23, 2024.
U.S. Appl. No. 17/746,361 Office Action dated Apr. 29, 2025.
U.S. Appl. No. 17/824,720 Office Action dated May 19, 2025.
U.S. Appl. No. 17/941,815 Office Action dated Oct. 26, 2023.
U.S. Serial No. 17/962, 142 Office Action dated Apr. 25, 2025.
U.S. Appl. No. 18/077,097 Corrected Notice of Allowability dated Dec. 26, 2023.
U.S. Appl. No. 18/077,097 Notice of Allowance dated Oct. 27, 2023.
U.S. Appl. No. 18/077,097 Office Action dated Aug. 3, 2023.
U.S. Appl. No. 18/416,505 Office Action dated Oct. 1, 2024.
U.S. Appl. No. 18/416,505 Office Action dated Jul. 14, 2025.
U.S. Appl. No. 18/423,043 Office Action dated Nov. 4, 2024.
U.S. Appl. No. 18/645,220 Office Action dated Mar. 17, 2025.
U.S. Appl. No. 18/939,459 Corrected Notice of Allowability dated May 29, 2025.
U.S. Appl. No. 18/939,459 Notice of Allowance dated May 16, 2025.
U.S. Appl. No. 18/939,459 Office Action dated Jan. 16, 2025.
Valipour, A. et al. First-in-Human Results of Bronchial Rheoplasty: An endobronchial Treatment for Chronic Bronchitis. American Thoracic Society :1-20 (2019).
Valipour, Arschang et al. Abstract 823—Bronchial Rheoplasty Treatment for Chronic Bronchitis Using the Rheox System: 12-Month Results of a Prospective, Multi-Center Study. American Thoracic Society. P. 1 (2020).
Valipour, Arschang et al. Abstract D94 Copd: Epidemiology And Therapy, First-in-Human Results of Bronchial Rheoplasty: An Endobronchial Treatment for Chronic Bronchitis (CB). American Thoracic Society International Conference : 1-5 (2019).
Valipour, Arschang, et al. Bronchial Rheoplasty for Treatment of Chronic Bronchitis, American Journal of Respiratory and Critical Care Medicine, vol. 202, No. 5, Sep. 1, 2020, pp. 681-689.
Valipour, Arschang et al. Bronchial Rheoplasty for Treatment of Chronic Bronchitis. Twelve-Month Results from a Multicenter Clinical Trial. American Journal of Respiratory and Critical Care Medicine 202(5):681-689 (2020).
Valipour, Arschang et al. Late Breaking Abstract—Bronchial Rheoplasty For Treatment of Chronic Bronchitis: 6-Month Results from a Prospective Multi-Center Study. European Respiratory Journal 54:RCT448, 1-5 (2019).
Valipour, Arschang et al. Late Breaking Abstract—First-in-Human Results of Bronchial Rheoplasty: An Endobronchial Treatment For Chronic Bronchitis (CB). European Respiratory Journal 52(Suppl_ 62):OA2162, 1-6 (2018).
Verma, Atul. et al. Primer on pulsed electrical field ablation: understanding the benefits and limitations. Circulation: Arrhythmia and Electrophysiology 14(9):e010086, 1-16 (2021).
Xie, Fei et al. Ablation of myocardial tissue with nanosecond pulsed electric fields. PLoS One 10(12):e0144833, 1-15 (2015).
Yavin, Hagai et al. Pulsed field ablation using a lattice electrode for focal energy delivery: biophysical characterization, lesion durability, and safety evaluation. Circulation: Arrhythmia and Electrophysiology 13(6):e008580, 1-10 (2020).
Al-Sakere, et al., Tumor Ablation with Irreversible Electroporation, *PLoS One*, 2(11): e1135. doi:10.1371/journal.pone.0001135 (Nov. 2007).
Arena C.B., et al., "Chapter 10.13: Electroporation Therapy," Comprehensive Biomedical Physics, Springer, Editor: A. Brahme, 2014, vol. 10, pp. 269-287 (20 Pages), Retrieved from URL: http://dx.doi.org/10.1016/8978-0-444-53632-7.01016-9.
Arena, et al., High-frequency irreversible electroporation (H-FIRE) for non-thermal ablation without muscle contraction, *BioMedical Engineering OnLine*, 10:102, http://www.biomedical-engineering-online.com/content/10/1/102 (Nov. 2011).
Bertacchini, et al., Design of an Irreversible Electroporation System for Clinical Use, *Technology in Cancer Research and Treatment*, 6(4):313-320 (Aug. 2007).
Bhonsle S., et al., "Characterization of Irreversible Electroporation Ablation with a Validated Perfused Organ Model," Journal of Vascular and Interventional Radiology, 2016, vol. 27, pp. 1913-1922 (12 Pages), Appendix A—Supplemental Materials and Methods.

(56) References Cited

OTHER PUBLICATIONS

Campelo S., et al., "An Evaluation of Irreversible Electroporation Thresholds in Human Prostate Cancer and Potential Correlations to Physiological Measurements," APL Bioengineering, 2017, vol. 1 (016101), pp. 016101-1-016101-10, Retrieved from URL: https://doi.org/10.1063/1.5005828.
Davalos, et al., Tissue Ablation with Irreversible Electroporation, *Annals of Biomedical Engineering*, 33(2):223-231 (Feb. 2005).
Dev, et al., Medical Applications of Electroporation, *IEEE Transactions on Plasma Science*, 28(1):206-223 (Feb. 2000).
Edd, et al., In Vivo Results of a New Focal Tissue Ablation Technique: Irreversible Electroporation, *IEEE Transactions On Biomedical Engineering*, 53(5): 1409-1415 (Jun. 2006).
Extended European Search Report for European Application No. 20840607.4, dated Jun. 27, 2023, 08 Pages.
Extended European Search Report for European Application No. 21853941.9, dated Jul. 23, 2024, 07 Pages.
Extended European Search Report for European Application No. 22820712.2, dated Apr. 7, 2025, 08 Pages.
Extended European Search Report for European Application No. 22821096.9, dated Aug. 6, 2025, 13 Pages.
Extended European Search Report for European Application No. 25184327.2, dated Jul. 15, 2025, 08 Pages.
Extended European Search Report for European Application No. EP22870831.9, dated Jun. 16, 2025, 10 Pages.
Garcia P.A., et al., "A Parametric Study Delineating Irreversible Electroporation from Thermal Damage Based on a Minimally Invasive Intracranial Procedure," BioMedical Engineering OnLine, Apr. 30, 2011, vol. 10, Article No. 34, 22 Pages, Retrieved from URL: http://www.biomedical-engineering-online.com/content/10/1/34.
Garcia P.A., et al., "An Experimental Investigation of Temperature Changes During Electroporation," URSI General Assembly and Scientific Symposium, Istanbul, Turkey, Aug. 13-20, 2011, 4 Pages.
Garcia P.A., et al., "Intracranial Nonthermal Irreversible Electroporation: In Vivo Analysis," The Journal of Membrane Biology, 2010, vol. 236, pp. 127-136.
Garcia P.A., et al., "Non-Thermal Irreversible Electroporation for Tissue Ablation," Chapter 3, Electroporation in Laboratory and Clinical Investigations, Editors: E. P. Spugnini and al Baldi, 2010, 22 Pages.
International Search Report & Written Opinion dated Aug. 29, 2025 in Int'l PCT Patent Appl. Serial No. PCT/US2025/028619.
International Search Report and Written Opinion for International Application No. PCT/US2020/042260, dated Oct. 14, 2020, 12 Pages.
International Search Report and Written Opinion for International Application No. PCT/US2021/030911, dated Aug. 16, 2021, 10 Pages.
International Search Report and Written Opinion for International Application No. PCT/US2021/044469, dated Nov. 8, 2021, 17 Pages.
International Search Report and Written Opinion for International Application No. PCT/US2022/015217, dated May 6, 2022, 12 Pages.
International Search Report and Written Opinion for International Application No. PCT/US2022/032981, dated Aug. 29, 2022, 15 Pages.
International Search Report and Written Opinion for International Application No. PCT/US2022/044021, dated Jan. 11, 2023, 11 Pages.
International Search Report and Written Opinion for International Application No. PCT/US2023/020282, dated Jul. 21, 2023, 14 Pages.
International Search Report and Written Opinion for International Application No. PCT/US2023/060897, dated Jul. 7, 2023, 15 Pages.
International Search Report and Written Opinion for International Application No. PCT/US2024/020309, dated Jul. 29, 2024, 10 Pages.
International Search Report and Written Opinion for International Application No. PCT/US2024/043295, dated Oct. 30, 2024, 9 Pages.
Invitation to Pay Additional Fees for International Application No. PCT/US2023060897, dated May 15, 2023, 10 Pages.
Jourabchi, et al., Irreversible Electroporation (NanoKnife) in Cancer Treatment, Gastrointestinal Intervention, 3:8-18 (Feb. 2014).
Krassowska, et al., Viability of Cancer Cells Exposed to Pulsed Electric Fields: The Role of Pulse Charge, *Annals of Biomedical Engineering*, 31:80-90 (2003).
Lee, et al., Advanced Hepatic Ablation Technique for Creating Complete Cell Death: Irreversible Electroporation, *Radiology*, 255(2) (Apr. 8, 2010).
Mercadal, et al., Avoiding nerve stimulation in irreversible electroporation: a numerical modeling study, *Phys. Med. Biol.*, 62(20):8060-8079 (Oct. 2004).
Miklavcic, et al., A validated model of in vitro electric field distribution in tissues for electrochemotherapy and for DNA electrotransfer for gene therapy, *Biochimica et Biophysica Acta*, 1523:73-83 (2000).
Miklavcic, et al., The effect of high frequency electric pulses on muscle contractions and antitumor efficiency in vivo for a potential use in clinical electrochemotherapy, *Bioelectrochemistry*, 65:121-128 (2005).
Miller, et al., Cancer Cells Ablation with Irreversible Electroporation, *Technology in Cancer Research & Treatment*, 4(6):699-705 (Dec. 2005).
Mir, et al., Mechanisms of electrochemotherapy, *Advanced Drug Delivery Reviews*, 35:107-118 (1999).
Napotnik, et al., Cell death due to electroporation—A Review, *Bioelectrochemistry*, 141:107871, pp. 1-18 (2021).
Neal II, R. E et al., "The Feasibility of Irreversible Electroporation for the Treatment of Breast Cancer and Other Heterogeneous Systems," Annals of Biomedical Engineering, Dec. 2009, vol. 37, No. 12, pp. 2615-2625.
Neal II R.E., et al., "An "Off-the-Shelf" System for Intraprocedural Electrical Current Evaluation and Monitoring of Irreversible Electroporation Therapy," Cardio Vascular and Interventional Radiology, 2014, vol. 38, No. 3, pp. 736-741 (6 Pages).
Neal II R.E., et al., "Chapter 5.4: Clinical Implications of Irreversible Electroporation: Clinical and Preclinical Findings," Springer, Editors: H Akiyama and R Heller (In Press), 10 Pages.
Neal II R.E., et al., "Experimental Characterization and Numerical Modeling of Tissue Electrical Conductivity during Pulsed Electric Fields for Irreversible Electroporation Treatment Planning," IEEE Transactions on Biomedical Engineering, Apr. 2012, vol. 59, No. 4, pp. 1076-1085.
Neal II R.E., et al., "Hepatic Epithelioid Hemangioendothelioma Treated With Irreversible Electroporation and Antibiotics," Journal of Clinical Oncology, 2013, vol. 31, 5 Pages, Retrieved from URL: http://jco.ascopubs.org/cgl/dol/10.1200/JCO.2012.44.9736.
Neal II R.E., et al., "Improved Local and Systemic Anti-Tumor Efficacy for Irreversible Electroporation in Immunocompetent versus Immunodeficient Mice," PLOS One, May 24, 2013, vol. 8, No. 5 (e64559), 10 Pages, DOI: 10.1371/journal.pone.0064559.
Neal II R.E., et al., "In Vitro and Numerical Support for Combinatorial Irreversible Electroporation and Electrochemotherapy Glioma Treatment," Annals of Biomedical Engineering, 2013, vol. 42, 13 Pages, DOI: 10.1007/s10439-013-0923-2.
Neal II R.E., et al., "In vivo Characterization and Numerical Simulation of Prostate Properties for Non-Thermal Irreversible Electroporation Ablation," The Prostate, 2014, vol. 17, No. 10 (22760), 11 Pages.
Neal II R.E., et al., "In Vivo Irreversible Electroporation Kidney Ablation: Experimentally Correlated Numerical Models," IEEE Transactions on Biomedical Engineering, 2013, 10 Pages, DOI: 10.1109/TBME.2014.2360374.
Neal II R.E., et al., "Spectrum of Imaging and Characteristics for Liver Tumors Treated With Irreversible Electroporation," Journal of Biomedical Science and Engineering, 2012, vol. 5, pp. 813-818.
Neal II R.E., et al., "The Effects of Metallic Implants on Electroporation Therapies: Feasibility of Irreversible Electroporation for

(56) References Cited

OTHER PUBLICATIONS

Brachytherapy Salvage," CardioVascular and Interventional Radiology, 2013, vol. 36, No. 6, pp. 1638-1645 (08 Pages).
Neal II R.E., et al., "Treatment of Breast Cancer through the Application of Irreversible Electroporation Using a Novel Minimally Invasive Single Needle Electrode," Breast Cancer Research and Treatment, Aug. 2010, vol. 123, No. 1, pp. 295-301 (13 Pages).
Neal II R.E., et al., "Successful Treatment of a Large Soft Tissue Sarcoma with Irreversible Electroporation," Journal of Clinical Oncology, May 1, 2011, vol. 29, No. 13, pp. e372-e377, DOI: 10.1200/JCO.2010.33.0902.
O'Brien T.J., et al., "Effects of Internal Electrode Cooling on Irreversible Electroporation Using a Perfused Organ Model," International Journal of Hyperthermia, 2019, vol. 35, No. 1, pp. 44-55 (12 Pages).
Rogers, et al., Strength-Duration Curve for an Electrically Excitable Tissue Extended Down to Near 1 Nanosecond, *IEEE Transactions on Plasma Science*, 32(4): 1587-1599 (Aug. 2004).
Rossmeisl J.H., Jr., et al., "Safety and Feasibility of the Nanoknife System for Irreversible Electroporation Ablative Treatment of Canine Spontaneous Intracranial Gliomas," Journal of Neurosurgery, Jul. 3, 2015, vol. 123, No. 4, pp. 1008-1025 (18 Pages).
Rubinsky, et al., Optimal Parameters for the Destruction of Prostate Cancer Using Irreversible Electroporation, *The Journal of Urology*, 180:2668-2674 (Dec. 2008).
Sano M.B., et al., "Towards the Creation of Decellularized Organ Constructs Using Irreversible Electroporation and Active Mechanical Perfusion," BioMedical Engineering OnLine, 2010, vol. 9, No. 83, 16 Pages, Retrieved from URL: http://www.biomedical-engineering-online.com/content/9/1/83.
Scheffer H.J., et al., "The Influence of a Metal Stent on the Distribution of Thermal Energy during Irreversible Electroporation," PLOS One, Feb. 4, 2016, vol. 11, No. 2 (e0148457), 13 Pages, DOI:10.1371/journal.pone.0148457.
Schoenbach K.H., et al., "Bioelectrics," Springer, Editors: H. Akiyama, R. Heller, 2017, 491 Pages, ISBN 978-4-431-56093-7, ISBN 978-4-431-56095-1 (eBook), DOI: 10.1007/978-4-431-56095-1.
Shah P.L., et al., "Epithelial Resurfacing: The Bronchial Skin Peel," American Thoracic Society, May 22, 2020, pp. 1-8 (9 Pages).
Thomson K.R., et al., "Introduction to Irreversible Electroporation-Principles and Techniques," Techniques in Vascular and Interventional Radiology, 2015, vol. 18, No. 3, pp. 128-134.
Valipour A., et al., "Bronchial Rheoplasty for Treatment of Chronic Bronchitis Twelve-Month Results from a Multicenter Clinical Trial," American Journal of Respiratory and Critical Care Medicine, 2019, vol. 202, No. 5, 27 Pages.
Vollmer, Robin T., Tumor Length In Prostate Cancer, *American Journal of Clinical Pathology*, 130(1): 77-82 (Jul. 2008).
Wandel A., et al., "Optimizing Irreversible Electroporation Ablation with a Bipolar Electrode," The Journal of Vascular and Interventional Radiology, Sep. 2016, vol. 27, No. 9, pp. 1441-1450 (12 Pages).

* cited by examiner

DEVICES, SYSTEMS AND METHODS FOR TREATMENT OF LUNG AIRWAYS

CROSS REFERENCE TO RELATED APPLICATIONS

This application is a continuation of PCT Application No. PCT/US23/22109, filed May 12, 2023, which claims the benefit of U.S. Provisional Application No. 63/341,937 filed May 13, 2022, which is incorporated herein by reference in its entirety.

BACKGROUND

I. Anatomy

FIG. 1 provides an illustration of the pulmonary anatomy. Air travels down the trachea T and into the lungs L where the trachea T branches into a plurality of airways that extend throughout the lungs L. The trachea T first bifurcates into the right and left mainstem bronchi MB at the carina CA. These main bronchi MB further divide into the lobar bronchi LB, segmental bronchi SB, sub-segmental bronchi SSB, and terminate with the alveoli A. The diameters of the airways decrease as they bifurcate. The trachea T can have a luminal diameter ranging from about 15 mm to 22 mm, the mainstem bronchi MB can have a luminal diameter ranging from about 12 mm to 16 mm, the lobar bronchi LB can have a luminal diameter ranging from about 9 mm to 12 mm, and the diameter of subsequent bronchi continue to become smaller. The length of the airway also varies with each segment. In some patients, the trachea T has a length of about 12 cm, the mainstem bronchi MB has a length of about 4.8 cm, the lobar bronchi LB has a length of about 1.9 cm, and the length of subsequent bronchi continue to become shorter. In addition, the airway walls become thinner and have less supporting structure as they move more distally into the lung tissue.

The airways of the lung L are comprised of various layers, each with one or several types of cells. FIG. 2 illustrates a cross-sectional view representative of an airway wall W having a variety of layers and structures. The inner-most cellular layer of the airway wall W is the epithelium or epithelial layer E which includes pseudostratified columnar epithelial cells PCEC, goblet cells GC and basal cells BC. Goblet cells GC are responsible for the secretion of mucus M, which lines the inner wall of the airways forming a mucus blanket. The pseudostratified columnar epithelial cells PCEC include cilia C which extend into the mucus blanket. Cilia C that are attached to the epithelium E beat towards the nose and mouth, propelling mucus M up the airway in order for it to be expelled.

The basal cells BC attach to the basement membrane BM, and beneath the basement membrane BM resides the submucosal layer or lamina propria LP. The lamina propria LP includes a variety of different types of cells and tissue, such as smooth muscle SM. Smooth muscle is responsible for bronchoconstriction and bronchodilation. The lamina propria LP also include submucosal glands SG. Submucosal glands SG are responsible for much of the inflammatory response to pathogens and foreign material. Likewise, nerves N are present. Nerve branches of the vagus nerve are found on the outside of the airway walls or travel within the airway walls and innervate the mucus glands and airway smooth muscle, connective tissue, and various cell types including fibroblasts, lymphocytes, mast cells, in addition to many others. And finally, beneath the lamina propria LP resides the cartilaginous layer CL.

FIG. 3 provides a cross-sectional illustration of the epithelium E of an airway wall W showing types of cellular connections within the airway. Pseudostratified columnar epithelial cells PCEC and goblet cells GC are connected to each other by tight junctions TJ and adherens junctions AJ. The pseudostratified columnar epithelial cells PCEC and goblet cells GC are connected to the basal cells BC by desmosomes D. And, the basal cells BC are connected to the basement membrane BM by hemidesmosomes H.

II. Pulmonary Disorders

FIGS. 4A-4B depict bronchial airways B in healthy and diseased states, respectively. FIG. 4A illustrates a bronchial airway B in a healthy state wherein there is a normal amount of mucus M and no inflammation. FIG. 4B illustrates a bronchial airway B in a diseased state, such as chronic obstructive pulmonary disease, particularly chronic bronchitis. Chronic bronchitis is characterized by a persistent airflow obstruction, chronic cough, and sputum production for at least three months per year for two consecutive years. FIG. 4B illustrates both excess mucus M and inflammation I which leads to airway obstruction. The airway inflammation I is consistent with a thickened epithelial layer E.

A variety of pulmonary disorders and diseases can lead to airway inflammation, damage and obstruction. A few of these disorders, diseases and infections will be described briefly herein.

A. Chronic Obstructive Pulmonary Disease (COPD)

Chronic Obstructive Pulmonary Disease (COPD) is a common disease characterized by chronic irreversible airflow obstruction and persistent inflammation as a result of noxious environmental stimuli, such as cigarette smoke or other pollutants. COPD includes a range of diseases with chronic bronchitis and asthma primarily affecting the airways; whereas, emphysema affects the alveoli, the air sacs responsible for gas exchange. Some individuals have characteristics of both.

In chronic bronchitis, the airway structure and function is altered. In chronic bronchitis, noxious stimuli such as cigarette smoke or pollutants are inhaled and recognized as foreign by the airways, initiating an inflammatory cascade. Neutrophils, lymphocytes, macrophages, cytokines and other markers of inflammation are found in the airways of people with prolonged exposure, causing chronic inflammation and airway remodeling. Goblet cells can undergo hyperplasia, in which the cells increase in number, or hypertrophy, in which the goblet cells increase in size. Overall, the goblet cells produce more mucus as a response to the inflammatory stimulus and to remove the inhaled toxins. The excess mucus causes further airway luminal narrowing, leading to more obstruction and the potential for mucus plugging at the distal airways. Cilia are damaged by the noxious stimuli, and therefore the excess mucus remains in the airway lumen, obstructing airflow from proximal to distal during inspiration, and from distal to proximal during the expiratory phase. Smooth muscle can become hypertrophic and thicker, causing bronchoconstriction. Submucosal glands can also become hyperplastic and hypertrophic, increasing their mucus output, as well as the overall thickness of the airway wall and, which further constricting the diameter of the lumen. All of these mechanisms together contribute to chronic cough and expectoration of copious mucus. In severe cases of mucus plugging, the plugs prevent airflow to the alveoli, contributing to chronic hypoxia and respiratory acidosis.

In addition to a reduction in the luminal diameter or complete plugging of the airway, mucus hypersecretion can also lead to an exacerbation, or general worsening of health. As a consequence of the excess mucus and damaged cilia, pathogens such as bacteria (e.g., *Haemophilus influenzae, Streptococcus pneumoniae, Moraxella catarrhalis, Staphylococcus aureus, Pseudomonas aeruginosa, Burkholderia cepacia*, opportunistic gram-negatives, mycoplasma pneumoniae, and chlamydia pneumoniae), viruses (rhinoviruses, influenze/parainfluenza viruses, respiratory syncytial virus, coronaviruses, herpes simplex virus, adenoviruses), and other organisms (e.g., fungi) can flourish, causing an exacerbation, resulting in a set of symptoms. These include worsening cough, congestion, an increase in sputum quantity, a change in sputum quality, and/or shortness of breath. Treatment for an acute exacerbation can include oral or intravenous steroids, antibiotics, oxygen, endotracheal intubation and the need for mechanical ventilation via a ventilator.

III. Pulmonary Treatments

In some instances, the most effective treatment for a pulmonary disorder is a lifestyle change, particularly smoking cessation. This is particularly the case in COPD. However, many patients are unable or unwilling to cease smoking. A variety of treatments are currently available to reduce symptoms of pulmonary disorders.

A. Interventional Procedures

A variety of thermal ablation approaches have been described as therapies to treat diseased airways, but all have limitations and challenges associated with controlling the ablation and/or targeting specific cell types. Spray cryotherapy is applied by spraying liquid nitrogen directly onto the bronchial wall with the intent of ablating superficial airway cells and initiating a regenerative effect on the bronchial wall. Since the operator (e.g. physician) is essentially 'spray painting' the wall, coverage, dose and/or depth of treatment can be highly operator dependent without appropriate controllers. This can lead to incomplete treatment with skip areas that were not directly sprayed with nitrogen. Lack of exact depth control can also lead to unintended injury to tissues beyond the therapeutic target such as lamina propria and cartilage, especially since airway wall thickness can vary. Radiofrequency and microwave ablation techniques have also been described wherein energy is delivered to the airway wall in a variety of locations to ablate diseased tissue. Due to uncontrolled thermal conduction, an inability to measure actual tissue temperature to control energy delivery, risk of overlapping treatments, and variable wall thickness of the bronchi, these therapies can cause unintended injury to tissues beyond the therapeutic target, as well. In addition, since they all require repositioning of the catheter for multiple energy applications, incomplete treatment can also occur. All of these thermal ablative technologies non-selectively ablate various layers of the airway wall, often undesirably ablating non-target tissues beyond the epithelium or submucosa. As a consequence of damage to tissues beyond the therapeutic targets of the epithelium, an inflammatory cascade can be triggered, resulting in inflammation, which can lead to an exacerbation, and remodeling. As a result, the airway lumen can be further reduced. Thus, continued improvements in interventional procedures are needed which are more controlled, targeted to specific depths and structures that match the physiologic malady, while limiting the amount of inflammatory response and remodeling.

Asthmatx has previously developed a radiofrequency ablation system to conduct Bronchial Thermoplasty. The operator deploys a catheter in the airways and activates the electrode, generating heat in the airway tissue in order to thermally ablate smooth muscle. Because of the acute inflammation associated with the heat generated in the procedure, many patients experience acute exacerbations. In the AIR2 clinical study, patients did not experience a clinically significant improvement in the Asthma Quality of Life Questionnaire at 12 months as compared to a sham group. However, the treatment group had fewer exacerbations and a decrease in emergency room visits. The FDA approved the procedure, but it is not commonly used due to the side effects and the designation by insurers as an investigational procedure.

There is hence an unmet need for interventional procedures which are more controlled, targeted to specific structures and/or pathogens that match the pathophysiologic aberrancy or aberrancies, able to treat relatively large surface areas at the appropriate depth, and limit the amount of inflammatory response and remodeling. Such procedures should be easy to use, safe and effective. Embodiments of the present disclosure meet at least some of these objectives.

SUMMARY

Described herein are embodiments of apparatuses, systems and methods for treating target tissue. Likewise, the invention relates to the following numbered clauses:

1. A grip device for mating a handle of a treatment catheter with an endoscope handle of an endoscope:
   - a mounting element configured to mate with the handle of a treatment catheter, wherein the treatment catheter includes a shaft coupled with the handle and configured to be advanced through a working channel port of the endoscope; and
   - a grip saddle configured to mate with the endoscope handle so that movement of the endoscope handle moves the mated handle of the treatment catheter in unison while the shaft is independently advanceable through the working channel port of the endoscope.
2. A grip device as in clause 1, wherein the grip saddle is shaped to conform to a portion of the endoscope handle.
3. A grip device as in clause 2, wherein the portion of the endoscope handle resides between a suction port and the working channel port.
4. A grip device as in clause 2, wherein the mounting element is coupled to an arm that holds the mounting element at a distance from the grip saddle.
5. A grip device as in clause 4, wherein the distance is sufficient to allow at least a hand to be inserted between the mounting element and the grip saddle.
6. A grip device as in any of clauses 4-5, wherein the mounting element is coupled to the arm by a joint connection which allows the mounting element to rotate in relation to the arm.
7. A grip device as in clause 6, wherein the joint connection allows the mounting element to rotate forward and/or backward.
8. A grip device as in clause 7, the mounting element is configured to receive the handle of the treatment catheter so that forward rotation of the mounting element advances the shaft within the working channel port and backward rotation of the mounting element retracts the shaft within the working channel port.

9. A grip device as in any of clauses 6-8, wherein the joint connection allows the mounting element to rotate left and/or right.

10. A grip device as in any of clauses 6-9, wherein the joint connection comprises a pivot joint.

11. A grip device as in any of clauses 6-9, wherein the joint connection allows the mounting element to rotate in all directions.

12. A grip device as in clause 11, wherein the joint connection comprises a ball joint.

13. A grip device as in any of clauses 1-12, wherein the mounting element is configured to slidably mate with the handle of the treatment catheter.

14. A grip device as in clause 13, wherein the mounting element comprises a mounting rail.

15. A grip device as in any of clauses 13-14, wherein sliding advancement of the handle of the treatment catheter along the mounting element advances the shaft within the working channel port of the endoscope.

16. A grip device as in any of clauses 1-15, wherein the handle of the treatment catheter includes one or more mechanisms for manipulating the treatment catheter, and wherein the mounting element is configured so that the one or more mechanisms is manipulatable by a hand while simultaneously holding the grip saddle against the endoscope handle with the hand.

17. A grip device as in clause 16, wherein the treatment catheter comprises an energy delivery body and wherein manipulation of the one or more mechanisms affects the energy delivery body.

18. A grip device as in clause 17, wherein the energy delivery body comprises an expandable structure and wherein manipulation of the one or more mechanisms expands and/or contracts the expandable structure.

19. A grip device as in clause 18, wherein the one or more mechanisms comprises a lever wherein depression of the lever expands or contracts the expandable structure.

20. A grip device as in clause 18, wherein the one or more mechanisms comprises a trigger actuator having a shape configured for insertion of one or more fingers of the hand therethrough, wherein movement of the trigger actuator expands or contracts the expandable structure.

21. A grip device as in clause 20, wherein the trigger actuator is positioned so that the trigger actuator is movable by the hand while simultaneously holding the grip saddle against the endoscope handle with the hand.

22. A grip device as in any of clauses 18-21, wherein the one or more mechanisms is coupled to the expandable structure by a planetary gear train.

23. A grip device as in any of the above clauses, further comprising at least one attachment mechanism configured to attach the grip saddle to the endoscope handle.

24. A grip device as in any of the above clauses, wherein the mounting element is fixedly attached to the handle of the treatment catheter.

25. A grip device as in any of the above clauses, wherein the grip saddle is fixedly attached to the endoscope handle.

26. A grip device as in any of the above clauses, wherein the treatment catheter comprises an energy delivery body comprising an expandable basket-shaped electrode.

27. A grip device as in any of the above clauses, wherein the endoscope comprises a bronchoscope.

28. A system for treating a patient with the use of an endoscope having an endoscope handle comprising:
  a treatment catheter having a distal end and a proximal end, wherein the treatment catheter includes a handle near the proximal end and a shaft extending toward the distal end and wherein the shaft is configured to be advanced through a working channel port of the endoscope; and
  a grip device configured to mate with the handle of the treatment catheter and the endoscope handle so that movement of the endoscope handle moves the handle of the treatment catheter in unison and so that the shaft is independently advanceable through the working channel port of the endoscope.

29. A system as in clause 28, wherein the grip device comprises a grip saddle configured to conform to a portion of the endoscope handle.

30. A system as in clause 29, wherein the portion of the endoscope handle resides between a suction port and the working channel port.

31. A system as in any of clauses 29-30, wherein the grip device includes a mounting element configured to mate with the handle of the treatment catheter, wherein the mounting element is coupled to an arm that holds the mounting element at a distance from the grip saddle.

32. A system as in clause 31, wherein the distance is sufficient to allow at least a hand to be inserted between the mounting element and the grip saddle.

33. A system as in any of clauses 31-32, wherein the mounting element is coupled to the arm by a joint connection which allows the mounting element to rotate in relation to the arm.

34. A system as in clause 33, wherein the joint connection allows the mounting element to rotate forward and/or backward.

35. A system as in clause 34, the mounting element is configured to receive the handle of the treatment catheter so that forward rotation of the mounting element advances the shaft within the working channel port and backward rotation of the mounting element retracts the shaft within the working channel port.

36. A system as in any of clauses 33-35, wherein the joint connection allows the mounting element to rotate left and/or right.

37. A system as in any of clauses 33-36, wherein the joint connection comprises a pivot joint.

38. A system as in any of clauses 33-36, wherein the joint connection allows the mounting element to rotate in all directions.

39. A system as in clause 38, wherein the joint connection comprises a ball joint.

40. A system as in any of clauses 31-39, wherein the mounting element is configured to slidably mate with the handle of the treatment catheter.

41. A system as in clause 40, wherein the mounting element comprises a mounting rail.

42. A system as in any of clauses 40-41, wherein sliding advancement of the handle of the treatment catheter along the mounting element advances the shaft within the working channel port of the endoscope.

43. A system as in any of clauses 28-42, wherein the handle of the treatment catheter includes one or more mechanisms for manipulating the treatment catheter, and wherein the mounting element is configured so that the one or more mechanisms is manipulatable by a hand while simultaneously holding the grip saddle against the endoscope handle with the hand.

44. A system as in clause 43, wherein the treatment catheter comprises an energy delivery body and wherein manipulation of the one or more mechanisms affects the energy delivery body.
45. A system as in clause 44, wherein the energy delivery body comprises an expandable structure and wherein manipulation of the one or more mechanisms expands and/or contracts the expandable structure.
46. A system as in clause 45, wherein the one or more mechanisms comprises a lever wherein depression of the lever expands or contracts the expandable structure.
47. A system as in clause 45, wherein the one or more mechanisms comprises a trigger actuator having a shape configured for insertion of one or more fingers of the hand therethrough, wherein movement of the trigger actuator expands or contracts the expandable structure.
48. A system as in clause 47, wherein the trigger actuator is positioned so that the trigger actuator is movable by the hand while simultaneously holding the grip saddle against the endoscope handle with the hand.
49. A system as in any of clauses 45-48, wherein the one or more mechanisms is coupled to the expandable structure by a planetary gear train.
50. A system as in any of clauses 28-49, wherein the grip device comprises at least one attachment mechanism configured to attach the grip saddle to the endoscope handle.
51. A system as in any of clauses 28-50, wherein the mounting element is fixedly attached to the handle of the treatment catheter.
52. A system as in any of clauses 28-51, wherein the grip saddle is fixedly attached to the endoscope handle.
53. A system as in any of clauses 28-52, wherein the treatment catheter comprises an energy delivery body comprising an expandable basket-shaped electrode.
54. A system as in any of clauses 28-53, wherein the endoscope comprises a bronchoscope.
55. A system as in any of clauses 28-54, wherein the shaft comprises a lumen and a cap at its distal end, wherein the lumen is fluidly connected with a slot along the cap which directs fluid flowing through the lumen radially outwardly through the slot to outside of the shaft.
56. A system as in clause 55, wherein the slot is contoured so as to direct at least a portion of the fluid flowing therethrough toward the proximal end of the shaft.
57. A system as in any of clauses 55-56, wherein the treatment catheter comprises an energy delivery body disposed along the shaft between the handle and the cap, and wherein the slot is contoured so as to direct at least a portion of the fluid flowing therethrough toward the energy delivery body.
58. A system as in any of clauses 55-57, further comprising a pump couplable with the treatment catheter so as to propel fluid through the lumen and out of the slot.
59. A system as in clause 58, wherein the pump is configured to propel the fluid at a flowrate that is sufficient to cause the fluid to flow out of the slot in a manner that flushes the energy delivery body.
60. A system as in clause 59, wherein the energy delivery body comprises an expandable basket-shaped wire electrode and the flowrate is sufficient to cause the fluid to flow out of the slot in a manner that at least partially removes mucus or bodily fluid from the basket-shaped wire electrode.
61. A system as in clause 58, wherein the endoscope comprises a lens and wherein the flowrate is sufficient to cause the fluid to flow out of the slot in a manner that at least partially removes mucus or bodily fluid from the lens.
62. A system as in any of clauses 28-61, wherein the treatment catheter comprises an energy delivery body along its distal end, and further comprising a generator couplable with the treatment catheter configured to deliver pulsed electric field energy via the energy delivery body.
63. A system as in clause 62, wherein the endoscope comprises a bronchoscope, and wherein the treatment catheter is configured to be advanced through a working channel port of the bronchoscope to treat tissue within a lung passageway of the patient so that the pulsed electric field energy is transmitted to a diseased portion of a wall of the lung passageway in a manner that induces reverse remodeling of the diseased portion of the wall so as to reduce mucus hypersecretion.
64. A system for treating a lung passageway having mucus comprising:
  - a shaft having a longitudinal axis, a lumen, a proximal end, and a distal end;
  - an energy delivery body disposed along the distal end;
  - a handle disposed along the proximal end, wherein the handle includes at least one manipulation mechanism configured to manipulate the energy delivery body so as to contact the lung passageway in a manner that transposes mucus to the energy delivery body; and
  - a cap having a slot, wherein the cap is disposed at the distal end so that the lumen is fluidly connected with the slot and wherein the slot is contoured so that fluid flowing through the lumen is directed through the slot to the outside of the shaft at an angle that directs the fluid toward the energy delivery body in a manner that removes at least a portion of the mucus from the energy delivery body.
65. A system as in clause 64, wherein the slot is contoured so that fluid flowing through the lumen is directed through the slot to the outside of the shaft at an angle that is less than 90 degrees from the longitudinal axis of the shaft.
66. A system as in clause 65, wherein the slot is contoured so that fluid flowing through the lumen is directed through the slot to the outside of the shaft at an angle that is less than or equal to 45 degrees from the longitudinal axis of the shaft.
67. A system as in any of clauses 64-66, wherein the slot is contoured so that fluid flowing through the lumen is directed through the slot to the outside of the shaft circumferentially around the shaft.
68. A system as in any of clauses 64-67, wherein the shaft is configured to be advanced through a working channel of a bronchoscope having a lens, and wherein the slot is contoured so that fluid flowing through the lumen is directed through the slot to the outside of the shaft in a manner that removes at least a portion of the mucus from the lens.
69. A system as in any of clauses 64-68, further comprising a pump couplable with the treatment catheter so as to propel fluid through the lumen and out of the slot.
70. A system as in clause 69, wherein the pump is configured to propel the fluid at a flowrate that is sufficient to cause the fluid to flow out of the slot in a manner that flushes the energy delivery body.
71. A system as in clause 70, wherein the energy delivery body comprises an expandable basket-shaped wire electrode and the flowrate is sufficient to cause the fluid to flow out of the slot in a manner that at least partially removes mucus from the basket-shaped wire electrode.

72. A system as in clause 70, wherein the flowrate is sufficient to cause the fluid to flow out of the slot in a manner that at least partially removes mucus from a lens of a bronchoscope through which the shaft is advanced.
73. A system as in any of clauses 64-72, further comprising a generator couplable with the treatment catheter configured to deliver pulsed electric field energy via the energy delivery body.
74. A system as in clause 73, wherein the shaft is configured to be advanced through a working channel port of a bronchoscope to treat tissue within the lung passageway of the patient so that the pulsed electric field energy is transmitted to a diseased portion of a wall of the lung passageway in a manner that induces reverse remodeling of the diseased portion of the wall so as to reduce mucus hypersecretion.
75. A system as in any of clauses 64-74 wherein the handle includes a grip saddle configured to mate with a bronchoscope handle so that movement of the bronchoscope handle moves the mated handle of the treatment catheter in unison while the shaft is independently advanceable through the working channel port of the bronchoscope.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of embodiments of the present disclosure are set forth with particularity in the appended claims. A better understanding of the features and advantages made possible by some embodiments will be obtained by reference to the following detailed description that sets forth illustrative embodiments, and the accompanying drawings of which:

DETAILED DESCRIPTION

Figure 1:
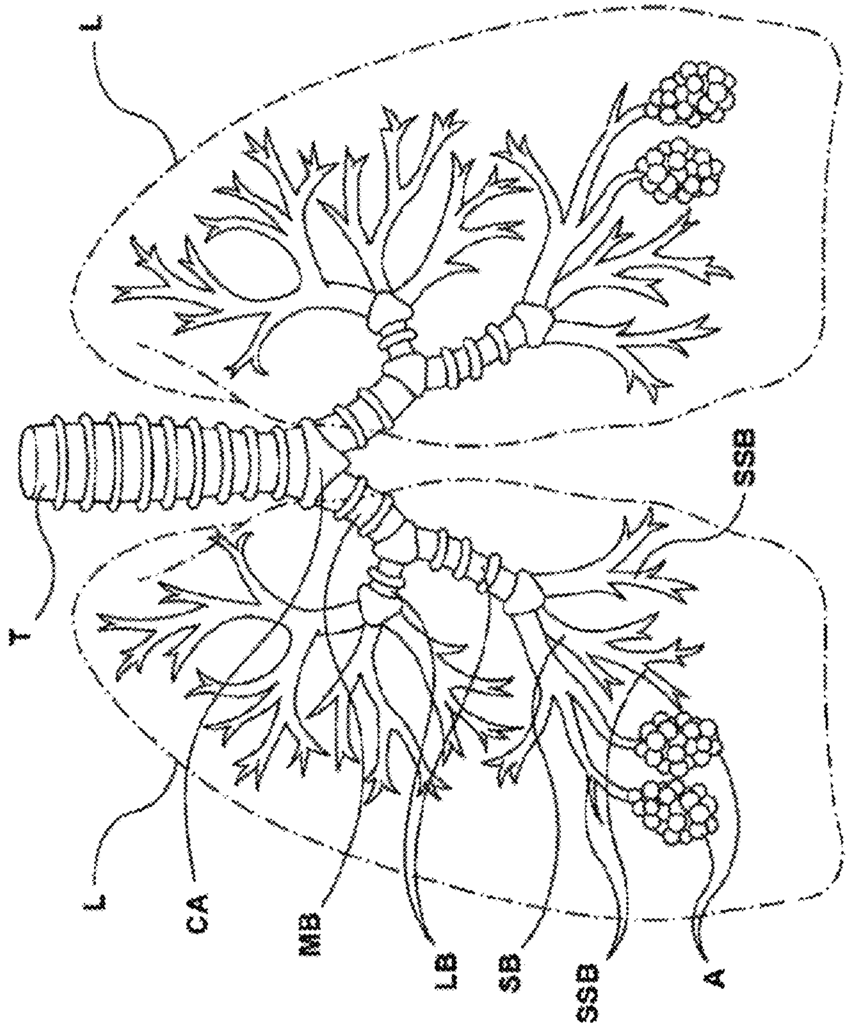
FIG. 1 (PRIOR ART)
FIG. 1 provides an illustration of the pulmonary anatomy.
Figure 2:
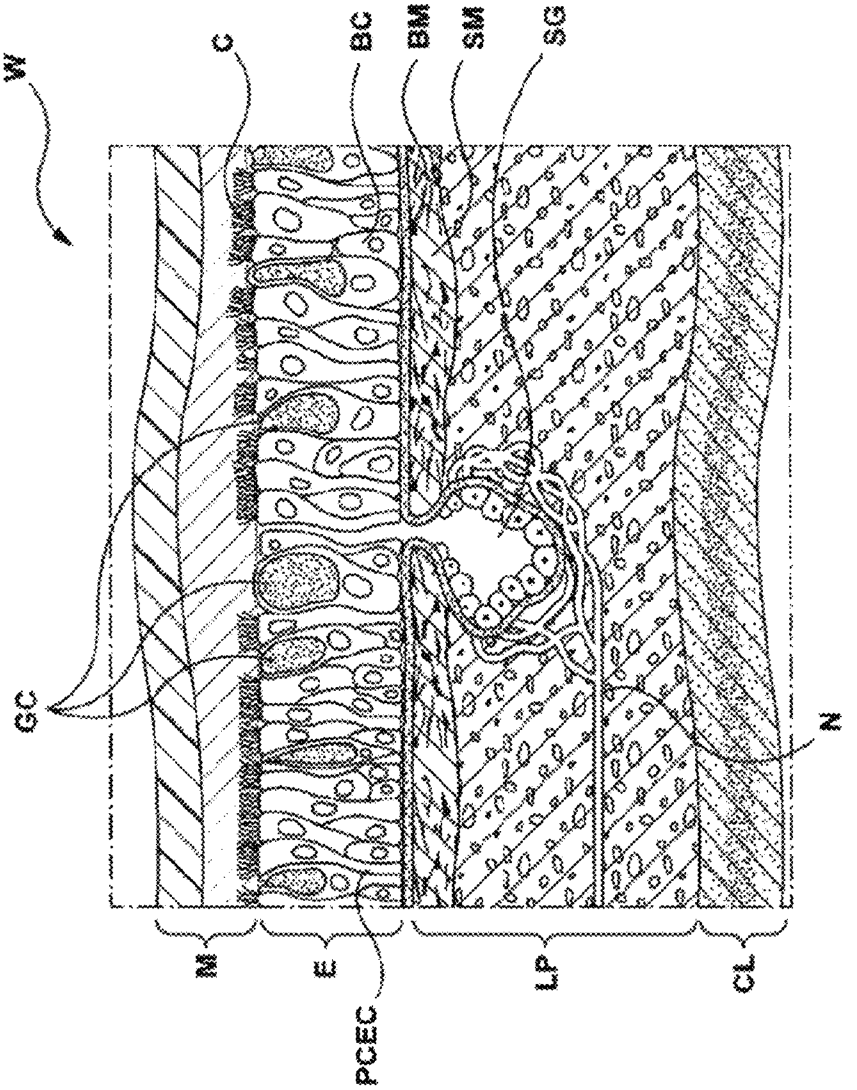
FIG. 2 (PRIOR ART)
FIG. 2 illustrates a cross-sectional view representative of an airway wall having a variety of layers and structures.
Figure 3:
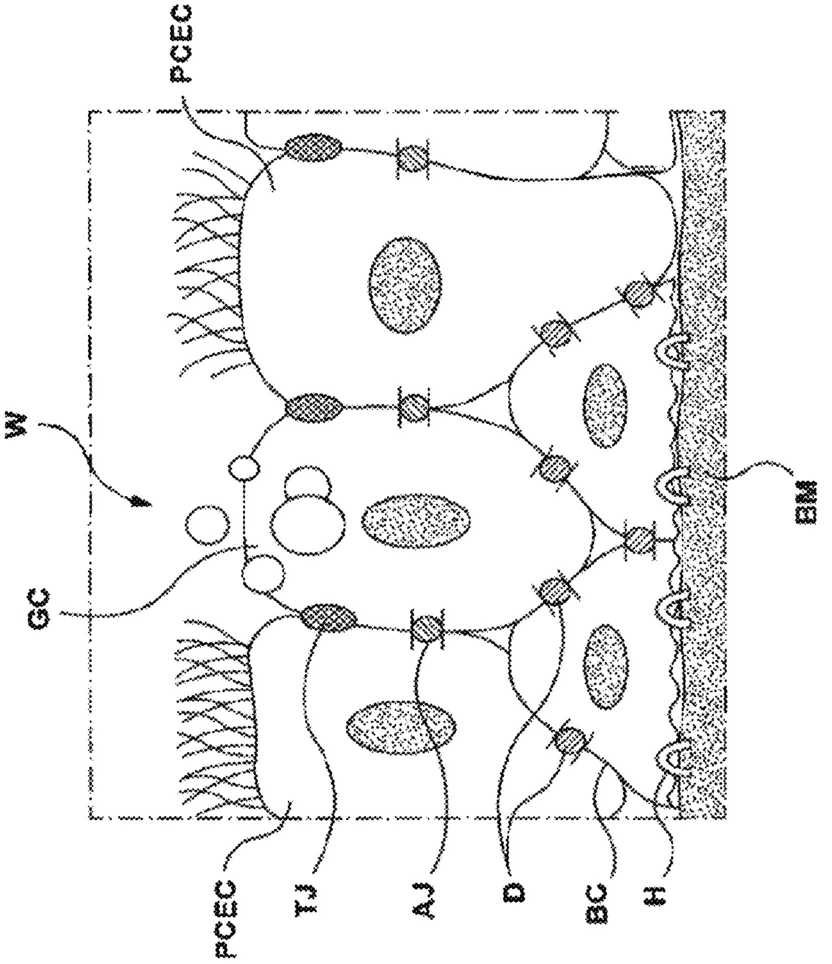
FIG. 3 (PRIOR ART)
FIG. 3 provides a cross-sectional illustration of the epithelium of an airway wall showing types of cellular connection within the airway.
Figure 4B:
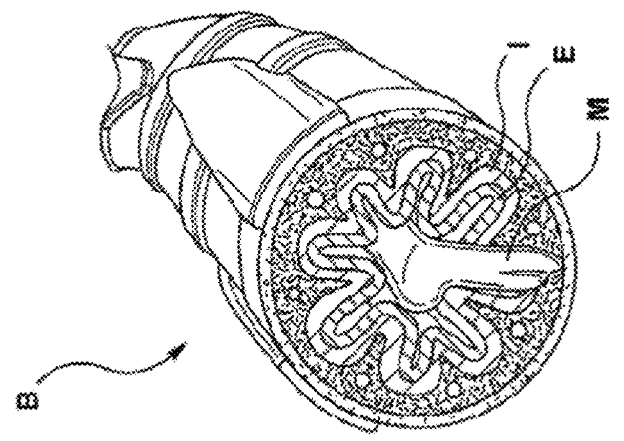
FIG. 4B (PRIOR ART)
FIGS. 4A-4B depict bronchial airways in healthy and diseased states, respectively.
Figure 4A:
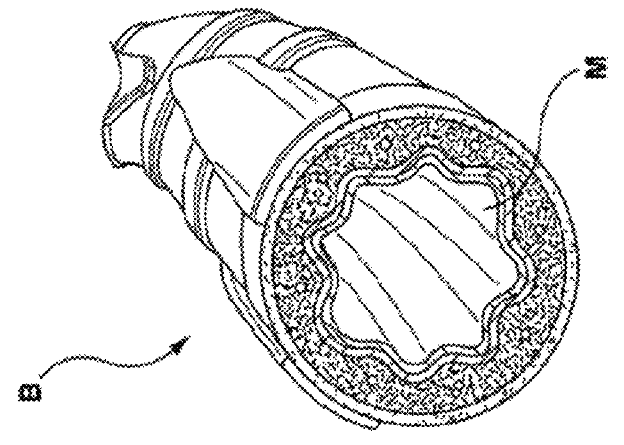
FIG. 4A (PRIOR ART)

Specific embodiments of the disclosed device, delivery system, and methods will now be described with reference to the drawings. Nothing in this detailed description is intended to imply that any particular component, feature, or step is essential to the implementation of any embodiment.

I. Overview

The secretion of mucus in the bronchial airways is an inherent part of the defense of the lungs, protecting the interior membranes and assisting in fighting off infections. The amount of mucus secretion varies with a range of stimuli, including bacteria, particles and chemical irritants. Normal secretion levels rise and fall depending on the transient conditions of the environment. Mucus on the epithelial layer of the bronchial airways traps particles and the ciliated cells permits moving of the mucus out of the lower airways so that it can ultimately be cleared by coughing or swallowing. Mucus also contains antibacterial agents to aid in its defense function. Pathogens and harmless inhaled proteins are thus removed from the respiratory tract and have a limited encounter with other immune components. In the bronchial airways, mucus is produced by goblet cells. Goblet cells produce mucins that are complexed with water in secretory granules and are released into the airway lumen. In the large airways, mucus is also produced by mucus glands. After infection or toxic exposure, the airway epithelium upregulates its mucus secretory ability to cause coughing and release of sputum. Subsequently, the airway epithelium recovers and returns to its normal state, goblet cells disappear, and coughing abates.

However, in some instances, such as in the development of many pulmonary disorders and diseases, the body does not recover, chronically producing too much mucus and causing it to accumulate in the lungs and plug the distal airways. This creates symptoms such as chronic coughing, difficulty breathing, fatigue and chest pain or discomfort. Such hypersecretion of mucus occurs in many disease states and is a major clinical and pathological feature in cystic fibrosis (CF) related bronchiectasis, non-CF bronchiectasis, chronic obstructive pulmonary disease and asthma, to name a few.

These disorders are all associated with an impaired innate lung defense and considerable activation of the host inflammatory response. Abnormal levels of antimicrobial peptides, surfactant, salivary lysozyme, sputum secretory leukocyte protease inhibitor, and macrophages in addition to signaling of toll-like receptors (TLRs), trigger pathways for mucin transcription and NF-KB (nuclear factor kappa-light-chain-enhancer of activated B cells). The increased mucus production and decreased clearance causes decreased ventilation, increased exacerbations and airway epithelial injury. Ciliary activity is disrupted and mucin production is upregulated. There is expansion of the goblet cell population. Epithelial cell proliferation with differentiation into goblet cells increases. Likewise, inflammation is elevated during exacerbations which activates proteases, destroying the elastic fibers that allow air and $CO_2$ to flow in and out of alveoli. In response to injury, the airway epithelium produces even more mucus to clear the airways of inflammatory cells. This progresses the disorder. Pathogens invade the mucus, which cannot be cleared. This primes the airways for another exacerbation cycle. As exacerbation cycles continue, the excessive mucus production leads to a pathological state with increased risk of infection, hospitalization and morbidity.

To interrupt or prevent the cycle of disease progression, the airways are treated with a pulmonary tissue modification system useful for impacting one or more cellular structures in the airway wall such that the airway wall structures are restored from a diseased/remodeled state to a relatively normal state of architecture, function and/or activity. The pulmonary tissue modification system treats pulmonary tissues via delivery of pulsed electric field energy, generally characterized by high voltage pulses. In some embodiments, the energy delivery allows for modification and/or removal of target tissue without a clinically significant inflammatory response, while in other embodiments, some inflammatory response is permissible. This allows for regeneration of healthy new tissue within days of the procedure. The newly regenerated goblet cells are significantly less productive of mucus and the newly generated ciliated pseudostratified columnar epithelial cells regrow normally functioning cilia which more easily expel mucus. Thus, reverse remodeling of the disease is achieved to reduce mucus hypersecretion. The reduction in mucus volume is felt directly by the patient, whose cough and airway obstruction are reduced. Over the ensuing weeks, this translates into a reduction in exacerbations and an improved quality of life.

The delivered energy is considered non-thermal (e.g. below a threshold for thermal ablation; below a threshold for inducing coagulative thermal damage), thereby maintaining the extracellular matrix while reducing or avoiding inflammation. In some embodiments, the algorithm 152 is tailored to affect tissue to a pre-determined depth and/or to target specific types of cells within the airway wall. Typically, depths of up to 0.01 mm, up to 0.02 mm, 0.01-0.02 mm, up to 0.03 mm, 0.03-0.05 mm, up to 0.05 mm, up to 0.08 mm, up to 0.09 mm, up to 0.1 mm, up to 0.2 mm, up to 0.5 mm, up to 0.7 mm, up to 1.0 mm, up to 1.5 mm, up to 2.0 mm, or up to 2.3 mm or less than 2.3 mm can be targeted, particularly when treating a lining of an airway or lung passageway. In some instances, the targeted pre-determined depth is 0.5 mm, such as when targeting airway epithelium and submucosal glands, with significant margin of safety to prevent any morbidity-associated cartilage effects at depths of 2.3 mm. In other instances, the targeted effect depth is more assertive to treat all of the airway epithelial cells and submucosal glands to a depth of up to 1.36 mm, while still preventing safety-associated effects to cartilage at depths of 2.3 mm.

After cell death, the inflammatory cascade ensues. Cell fragments and intracellular contents signal leukocytes and macrophages to enter the affected area of the airway wall W. Over the course of hours to days, the dead cells are cleared from the area via phagocytosis. Unlike thermal ablation which damages the extracellular matrix, phagocytosis is limited to the cellular remains and not the collagen or matrix components of the extracellular matrix.

Figure 5:
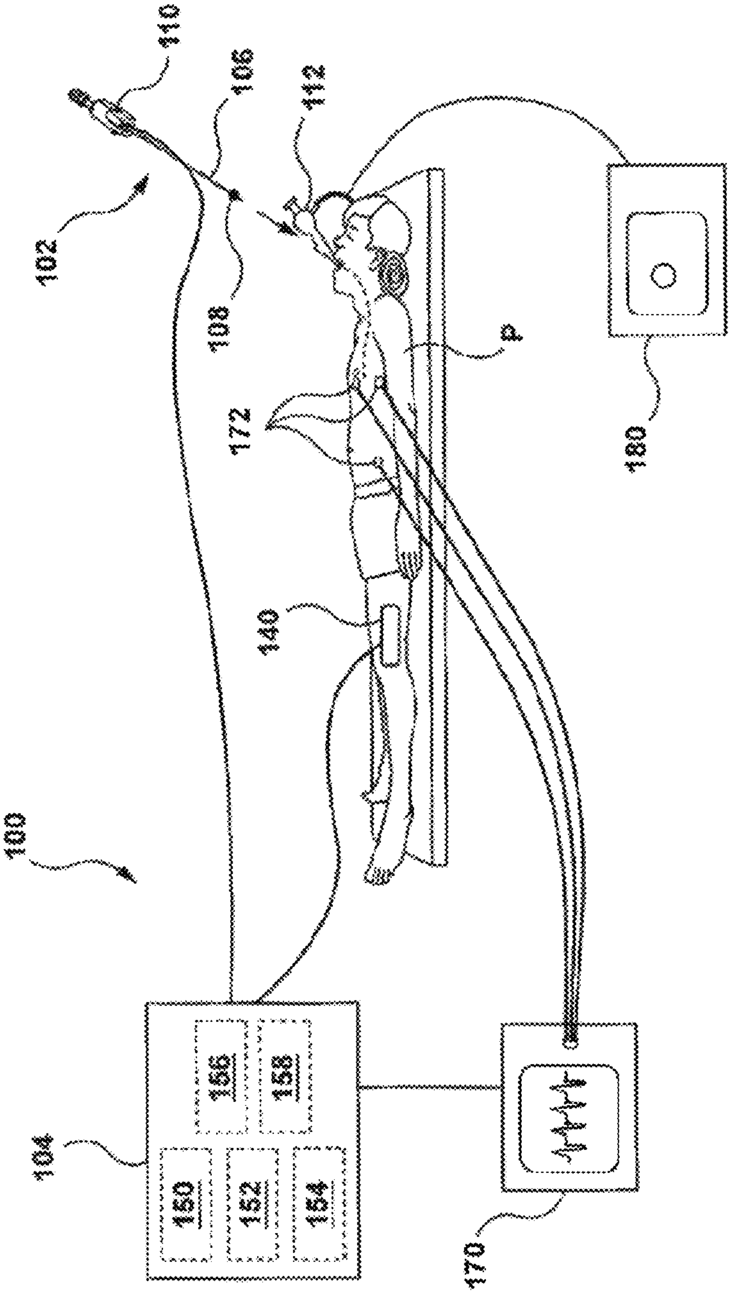
FIG. 5 illustrates an embodiment of a pulmonary tissue modification system used in treatment of a patient.

FIG. 5 illustrates an embodiment of a pulmonary tissue modification system 100 used in treatment of a patient P. In this embodiment, the system 100 comprises a therapeutic energy delivery catheter 102 connectable to a generator 104. The catheter 102 comprises an elongate shaft 106 having at least one energy delivery body 108 near its distal end and a handle 110 at its proximal end. Connection of the catheter 102 to the generator 104 provides electrical energy to the energy delivery body 108, among other features. The catheter 102 is insertable into the bronchial passageways of the patient P by a variety of methods, such as through a lumen in a bronchoscope 112, as illustrated in FIG. 5.

Figure 6:
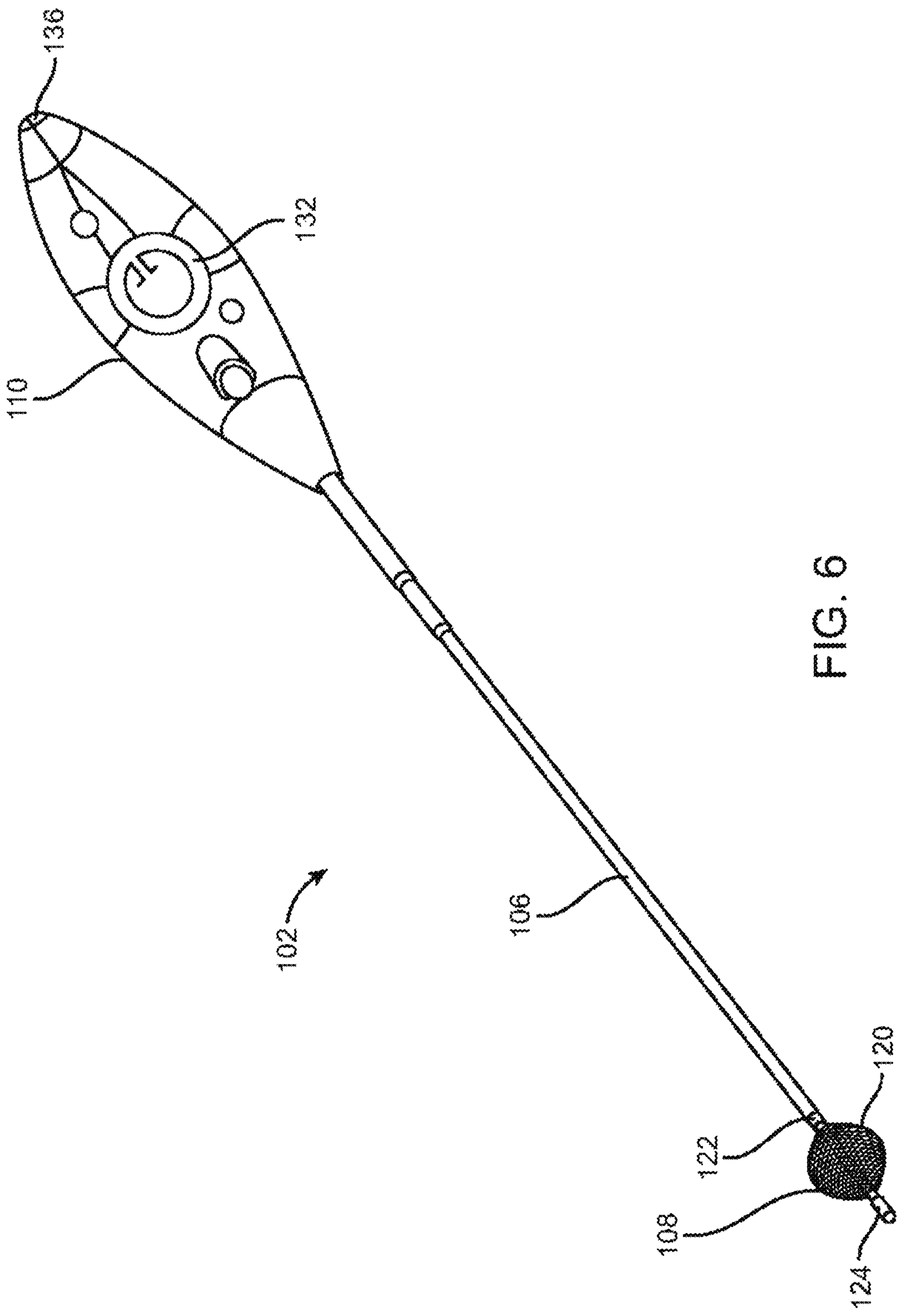
FIG. 6 provides a closer view of an embodiment of a therapeutic energy delivery catheter.

FIG. 6 provides a closer view of an embodiment of a therapeutic energy delivery catheter 102. In this embodiment, the energy delivery body 108 comprises a single monopolar delivery electrode, however it may be appreciated that other types, numbers and arrangements may be used. In this embodiment, the energy delivery body 108 is comprised of a plurality of wires or ribbons 120 constrained by a proximal end constraint 122 and a distal end constraint 124 forming a spiral-shaped basket serving as an electrode. In an alternative embodiment, the wires or ribbons are straight instead of formed into a spiral-shape (i.e., configured to form a straight-shaped basket). In still another embodiment, the energy delivery body 108 is laser cut from a tube.

The catheter 102 includes a handle 110 at its proximal end. In this embodiment, the handle has a streamlined oblong shape. In some embodiments, the handle 110 is removable, such as by pressing a handle removal button. In this embodiment, the handle 110 includes an energy delivery body manipulation mechanism 132 wherein movement of the mechanism 132 causes expansion or retraction/collapse of the energy delivery body 108 (i.e. basket-shaped electrode). In this embodiment, the shaft 106 comprises an outer shaft to which the proximal end of the energy delivery body 108 is attached and an inner shaft to which the distal end of the energy delivery body 108 is attached. Movement of the inner shaft relative to the outer shaft expands and collapses the energy delivery body 108. For example, in some embodiments, retraction of the inner shaft draws the distal end of the energy delivery body 108 toward the proximal end of the energy delivery body 108 thereby expanding the energy delivery body 108. The amount of travel controls the amount of expansion. In this embodiment, the handle 110 also includes a cable plug-in port 136 for connection with the generator 104 which provides energy to the energy delivery body 108.

It may be appreciated that maneuvering the catheter 102 and actuating the energy delivery body 108 involves dexterity and coordination. Typically, the catheter 102 is advanced through an endoscope, such as a bronchoscope, for delivery within the body. Thus, the user has two devices to maneuver and manipulate. In particular, the user is tasked with gross movement of both the catheter 102 and endoscope in relation to the body while at the same time performing fine movement of the catheter 102 in relation to the endoscope and various mechanisms of the catheter and endoscope themselves. This can be challenging for a user to perform alone. The process of navigating a catheter in the lungs and delivering energy to the lung tissue is typically performed by manual operations. The user pushes and pulls the catheter shaft through the lung airways, to position the distal electrode at the desired treatment location. The user then actuates a control on the catheter handle to deploy the electrode in the airway. Once deployed, energy is applied to the electrode, which then applies the energy to the lung airway wall.

One of the limitations of the procedure is shaft position accuracy. The user relies on muscle memory and limited visualization to place the device in the ideal location by detaching the device handle from the bronchoscope and moving the entire handle, which causes user fatigue which then affects procedure accuracy. Another limitation of the procedure is user fatigue during electrode deployment and collapse. The procedure involves as many as 130 actuations and repositions to perform the procedure completely. The repetitive motion of pushing and pulling a plunger can cause fatigue and injury to the user, causing user discomfort and also affecting procedure accuracy. Additionally, the plunger is typically in a non-ergonomic location and employs a non-ergonomic movement, causing fatigue and injury to the user, causing user discomfort and also affecting procedure accuracy. Thus, improved devices, systems and methods are provided herein to solve these issues, making the procedure more user friendly, and improving procedural ease of use, accuracy and ergonomics.

Figure 7:
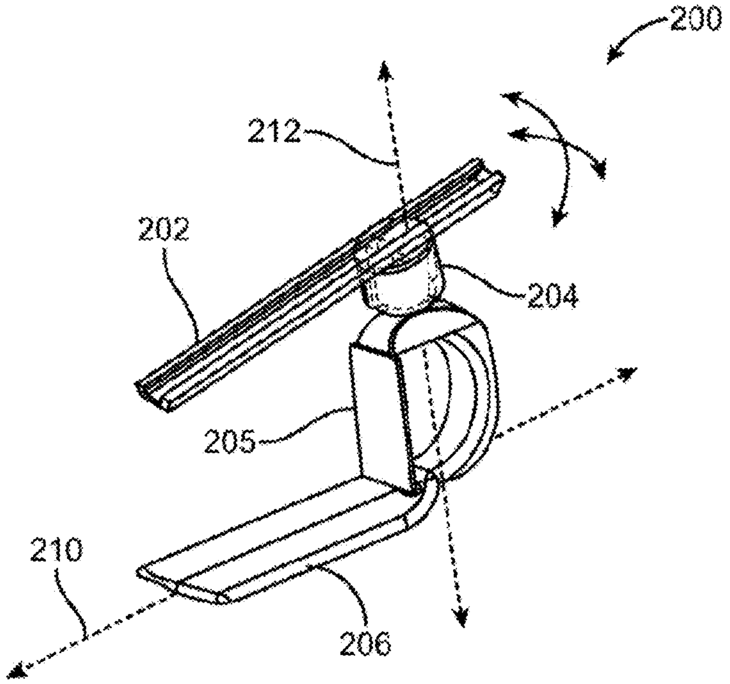
FIG. 7 illustrates a grip device upon which a handle of a therapeutic energy delivery catheter is mountable.

In some embodiments, a grip device 200 is provided, an embodiment of which is illustrated in FIG. 7. The handle 110 of the treatment catheter is mountable on the grip device 200 so that the grip device 200 can be used in conjunction with the handle of another device, particularly an endoscope, such as a bronchoscope 112. This allows the user to hold the handles of both devices with one hand, as will be described and illustrated herein. This leaves the other hand available for moving the catheter 102 in relation to the bronchoscope 112 and manipulating various mechanisms on the catheter 102 and bronchoscope 112 themselves. In this embodiment, the grip device 200 comprises a mounting element 202, an arm 205, a joint connection 204 and grip saddle 206. Here, the mounting element 202 comprises a mounting rail that is generally parallel to the grip saddle 206 with the joint connection 204 therebetween. In some embodiments, the handle 110 of the catheter 102 includes a handle rail 208 along its underside which is mateable with the mounting element 202 of the grip device 200. Typically, the handle rail 208 engages the mounting element 202 and slides along the mounting element 202 to a desired position. The handle 110 may be retained in this position by friction or by a specific mechanism, optionally including a locking feature. Thus, in this embodiment, the handle 110 may be positioned in a variety of locations optionally parallel to and aligned with a longitudinal axis 210 of the grip saddle 206. In this embodiment, the joint connection 204 comprises a ball joint. This allows the mounting element 202 to be rotated in a variety of directions relative to the grip saddle 206. For example, the mounting element 202 may remain in a plane substantially parallel to the grip saddle 206 and rotate angularly around the ball joint, such as angularly around an axis 212 that is perpendicular to the longitudinal axis 210. Or, the mounting element 202 may rotate up and down so as to tip the handle 110 toward or away from the longitudinal axis 210 when mounted on the mounting element 202. Or, the mounting element 202 may tip from side to side, rotating the mounting element 202 around an axis parallel to the longitudinal axis 210. Each of these maneuvers may assist in desirably positioning the catheter 102 in the body when in use.

Figure 8:
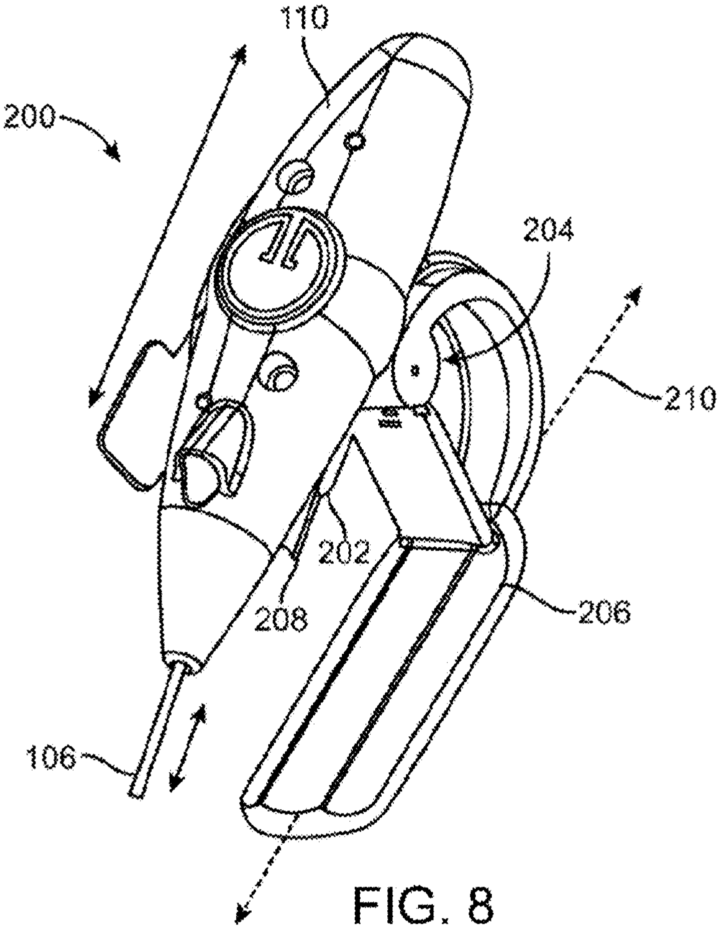
FIG. 8 illustrates another embodiment of a grip device.

FIG. 8 illustrates a similar grip device 200. Here the joint connection 204 comprises a pivot joint. Again, the handle 110 is includes a handle rail 208 that is mateable with the mounting element 202 of the grip device 200. The pivot joint allows the handle 110 to pivot around the joint connection 204 so as to tip the handle 110 toward or away from the longitudinal axis 210.

Figure 9:
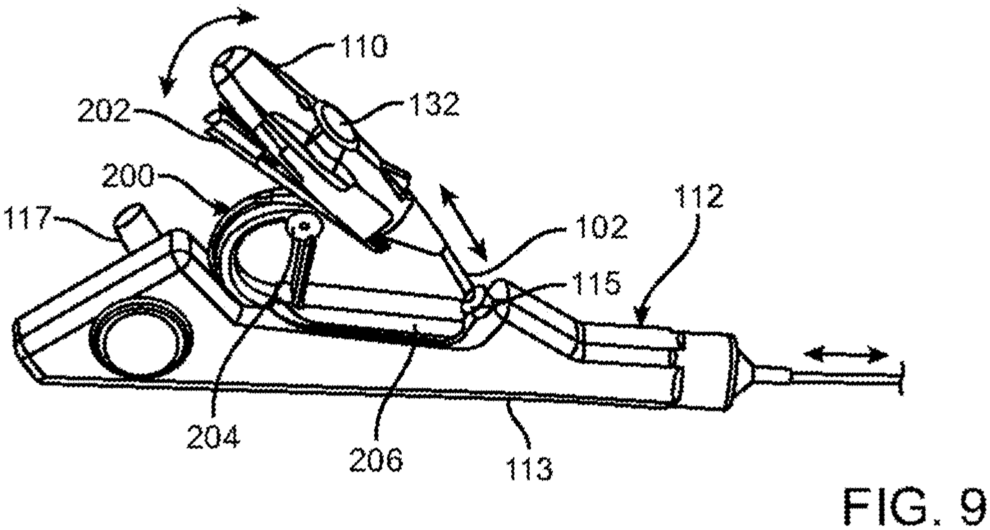
FIG. 9 illustrates the grip device of FIG. 8 positioned on a handle of a bronchoscope.

FIG. 9 illustrates the grip device 200 of FIG. 8 positioned on a bronchoscope handle 113 of a bronchoscope 112. As shown, the grip saddle 206 is disposed upon a side of the handle 113, such as along a contour between a working channel port 115 and a suction port 117. In some embodiments, the grip saddle 206 is contoured to mate with the handle 113, such as having curved edges which curve around the handle 113 to assist in securing its positioning. In some instances, the grip saddle 206 is removably or fixedly attached to the handle 113, such as with Velcro®-style hooks and loops, tape, adhesive, snaps, ties or other attachment mechanisms. In some instances, the handle 113 and/or entire bronchoscope 112 are disposable allowing such fixation without a need for later removal. Such positioning of the grip device 200 allows the shaft 106 of the catheter 102 to be inserted into the working channel port 115 of the bronchoscope 112. Thus, the shaft 106 is able to be advanced or retracted within the working channel by moving the handle 110 along the mounting element 202. Likewise, pivoting of the handle 113 also moves the shaft 106 within the working channel.

Figure 10A:
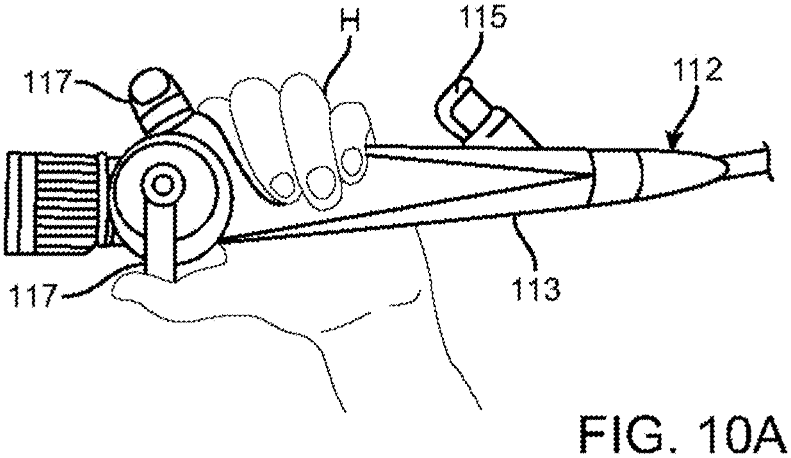
FIG. 10A illustrates a conventional bronchoscope handle and how a user typically holds the handle.
Figure 10B:
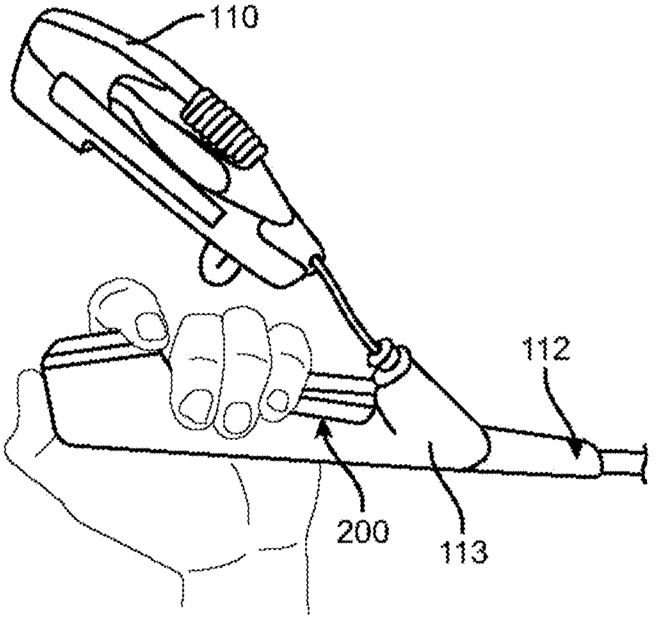
FIG. 10B illustrates the grip device mounted on a model of a bronchoscope handle and how a user is able to hold both the grip device and the bronchoscope handle with one hand.

FIG. 10A illustrates a conventional bronchoscope handle 113 and how a user typically holds the handle 113. As shown, the user grips the handle 113 with one hand H, typically between the working channel port 115 and the suction port 117. Typically, the user manipulates a bronchoscope lever 119 to steer the tip of the bronchoscope 112, such as with a thumb as illustrated. FIG. 10B illustrates the grip device 200 mounted on a model of a bronchoscope handle 113 and how a user is able to hold both the grip device 200 and the bronchoscope handle 113 with one hand. In some instances, the user holds the grip device 200 in place in relation to the bronchoscope handle 113 and in other instances the grip device 200 is secured to the bronchoscope handle 113 with the assistance of an attachment mechanism as previously described. Thus, the user is able to move both the bronchoscope 112 and the catheter 102 in relation to the patient with the gross motion of a single hand due to the catheter 102 being fixed in relation to the bronchoscope 112 by the grip device 200. Movement of the catheter 102 in relation to the bronchoscope 112 can be achieved with the other hand of the user.

Figure 11A:
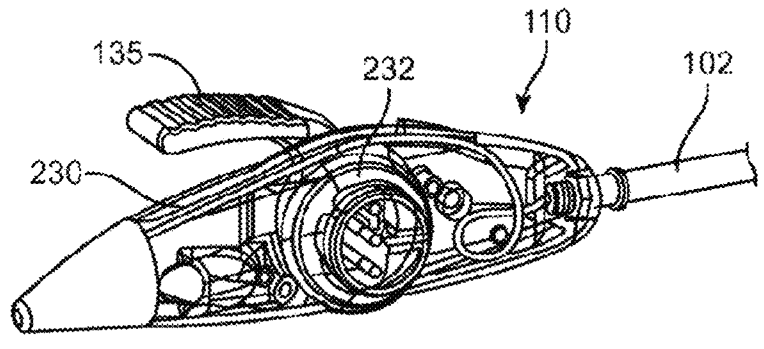
FIGS. 11A-11B illustrate another embodiment of a handle of catheter.
Figure 11B:
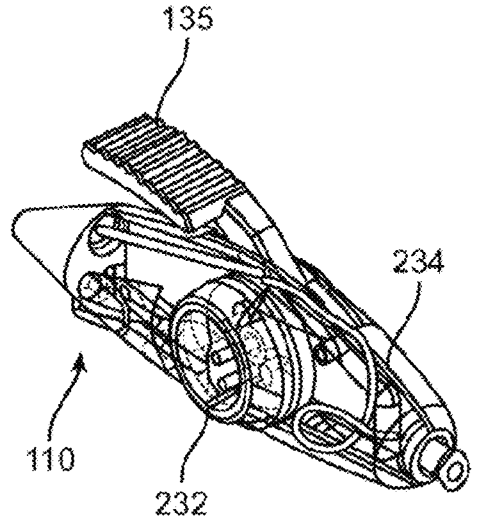

FIGS. 11A-11B illustrate another embodiment of a handle 110 of catheter 102. Here, the energy delivery body manipulation mechanism 132 comprises a lever 135. In this embodiment, depression of the level 135 causes expansion the energy delivery body 108. In particular, in this embodiment, the distal end of the energy delivery body 108 is attached to a cord whereby pulling the cord draws the distal end of the energy delivery body 108 toward the proximal end of the energy delivery body 108 which causes the wire basket electrode to expand. In this embodiment, the cord 230 is attached to a gear, such as a planetary gear 232 within the handle 110. Planetary gears are often used when space and weight are limited, but a larger amount of speed reduction and torque are desired. A planetary gear set is made up of three types of gears: a sun gear, planet gears, and a ring gear. The sun gear is located at the center and transmits torque to the planet gears which are typically mounted on a moveable carrier. The planet gears orbit around the sun gear and mesh with an outer ring gear. Planetary gear systems can vary in complexity from very simple to intricate compound systems. Planetary gear systems are able to produce significant torque because the load is shared among multiple planet gears. This arrangement also creates more contact surfaces and a larger contact area between the gears than a traditional parallel axis gear system. Because of this, the load is more evenly distributed and therefore the gears are more resistant to damage. In this embodiment, the planetary gear increases rotation of a pulley while requiring less travel from the lever 135. In some embodiments, movement of the lever 135 by 35-40 degrees provides a half turn to the planetary gear 232. Thus, the lever 135 increases mechanical advantage and reduces fatigue of the user.

In some embodiments, the user is able to determine the extent of expansion of the energy delivery body 108 by tactile feedback. In other embodiments, expansion is visualized by the bronchoscope 112. And in other embodiments, expansion is conveyed to the user by other means such as audible feedback (e.g. clicking, such as one click per mm of axial movement of the catheter 102). Audible feedback may be produced by a rachet system, etc.

FIG. 11B provides an additional view of the handle 110 of FIG. 11A. Here, a flush tube 234 is shown. In this embodiment, the flush tube 234 allows fluid to be passed through a lumen in the catheter 102. Here, the flush tube 234 is flexible so as to allow it to coil, fold, or bend within the handle 110 during axial translation of the cord 230.

Figure 12A:
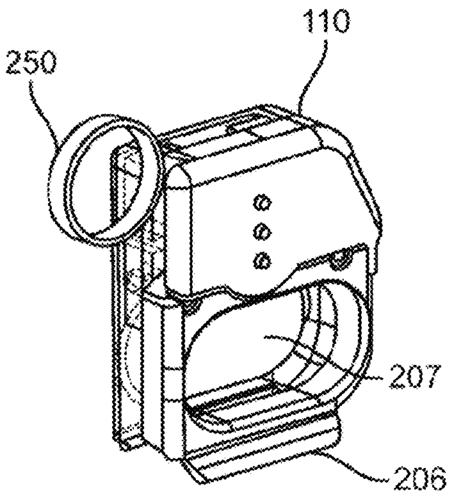
FIGS. 12A-12B illustrate further embodiment of a handle of a catheter.
Figure 12B:
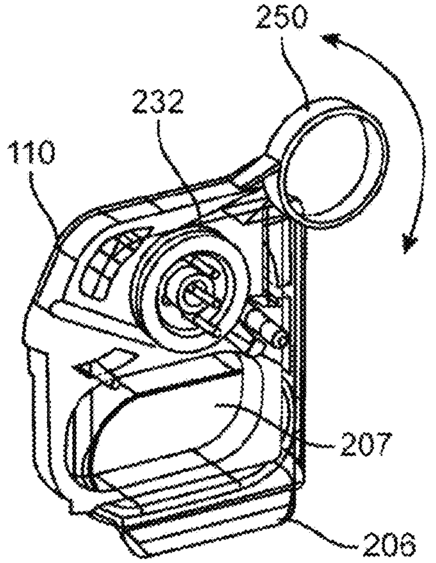

FIGS. 12A-12B illustrate another embodiment of a handle 110 of a catheter 102. However, in this embodiment, the handle 110 includes features of the grip device that are integral with its design. Therefore, it is not mountable on a grip device since it acts as a handle and grip device in one. For example, the handle 110 includes a grip saddle 206 for positioning against a handle 113 of an endoscope, such as a bronchoscope 112. In this embodiment, the grip saddle 206 has curved edges which curve around the handle 113 to assist in securing its positioning. The handle 110 includes an opening 207 above the grip saddle 206 for passing fingers of a hand therethrough. This allows the user to hold the handle 110 and the handle 113 of the bronchoscope 112 at the same time with one hand. In this embodiment, the handle 110 includes an energy delivery body manipulation mechanism 132 comprising a trigger actuator 250. In this embodiment, the trigger actuator 250 has a circular shape configured for insertion of one or more fingers therethrough. Depression of the trigger actuator 250 causes expansion the energy delivery body 108. In particular, in this embodiment, the distal end of the energy delivery body 108 is attached to a cord whereby pulling the cord draws the distal end of the energy delivery body 108 toward the proximal end of the energy delivery body 108 which causes the wire basket electrode to expand. In this embodiment, the cord 230 is attached to a gear, such as a planetary gear 232 within the handle 110. In this embodiment, the planetary gear increases rotation of a pulley while requiring less travel from the trigger actuator 250.

Figure 13:
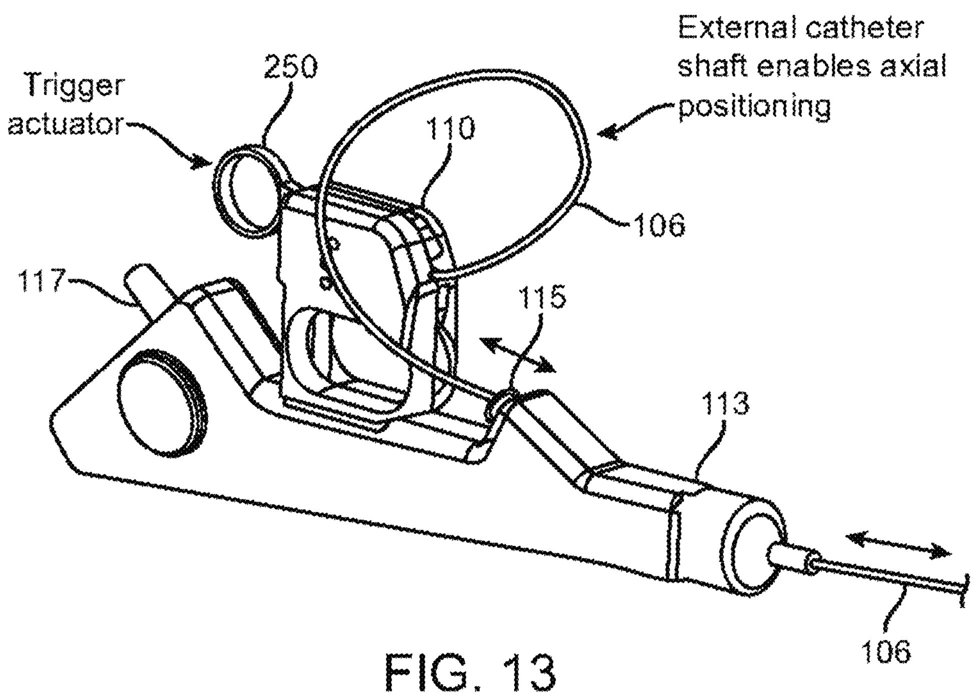
FIG. 13 illustrates the handle of FIGS. 12A-12B mounted on the handle of a bronchoscope.

FIG. 13 illustrates the handle 110 mounted on the handle of a bronchoscope 112. As shown, the grip saddle 206 is disposed upon a side of the handle 113, such as along a contour between a working channel port 115 and a suction port 117. In some embodiments, the grip saddle 206 is contoured to mate with the handle 113, such as having curved edges which curve around the handle 113 to assist in securing its positioning. In some instances, the grip saddle 206 is removably or fixedly attached to the handle 113, such as with Velcro®-style hooks and loops, tape, adhesive, snaps, ties or other attachment mechanisms. In some instances, the handle 113 and/or entire bronchoscope 112 are disposable allowing such fixation without a need for later removal. Such positioning of the handle 110 allows the shaft 106 of the catheter 102 to be inserted into the working channel port 115 of the bronchoscope 112. Here, the shaft 106 may be manipulated by the user by grasping the shaft 106 between the handle 110 and the working channel port 115. For example, axial movement of the catheter 102 and therefore energy delivery body 108 may be achieved by advancing or retracting the shaft 106 without moving the handle 110 itself.

Figure 14:
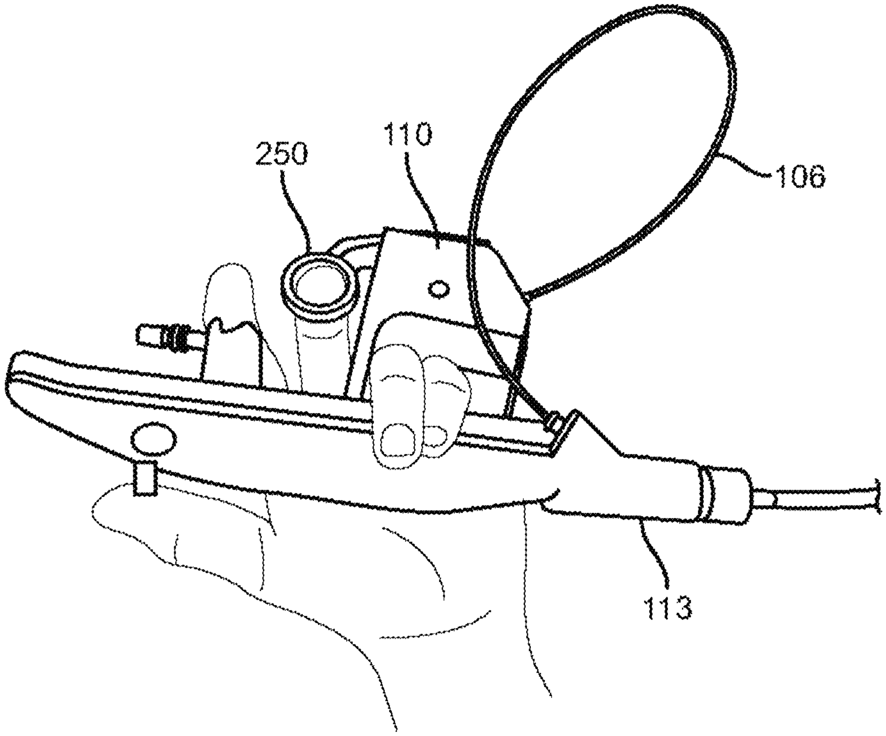
FIG. 14 illustrates the handle of FIGS. 12A-12B mounted on a bronchoscope handle and how a user is able to hold both the handle and the bronchoscope handle with one hand.

FIG. 14 illustrates the handle 110 mounted on a bronchoscope handle 113 and how a user is able to hold both the handle 110 and the bronchoscope handle 113 with one hand. In some instances, the user holds the handle 110 in place in relation to the bronchoscope handle 113 and in other instances the handle 110 is secured to the bronchoscope handle 113 with the assistance of an attachment mechanism as previously described. Thus, the user is able to move both the bronchoscope 112 and the catheter 102 in relation to the patient with the gross motion of a single hand due to the catheter 102 being fixed in relation to the bronchoscope 112 by the handle 110. Movement of the shaft 106 in relation to the bronchoscope 112 can be achieved with the other hand of the user or optionally with the same hand.

Figure 15:
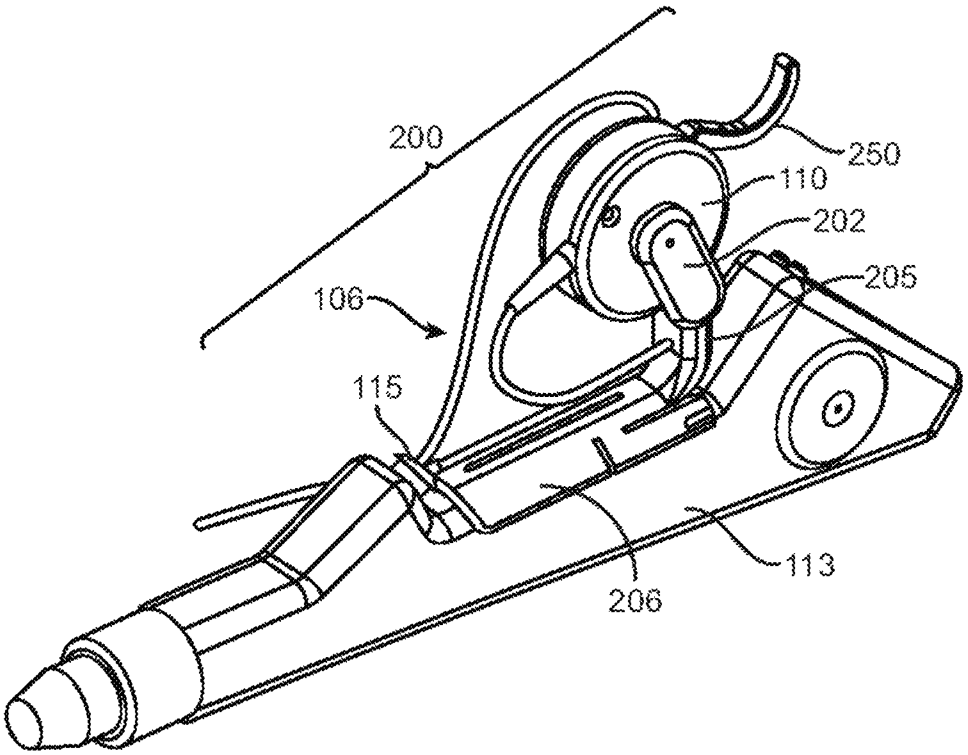
FIGS. 15-17 illustrate another embodiment of a grip device.
Figure 16:
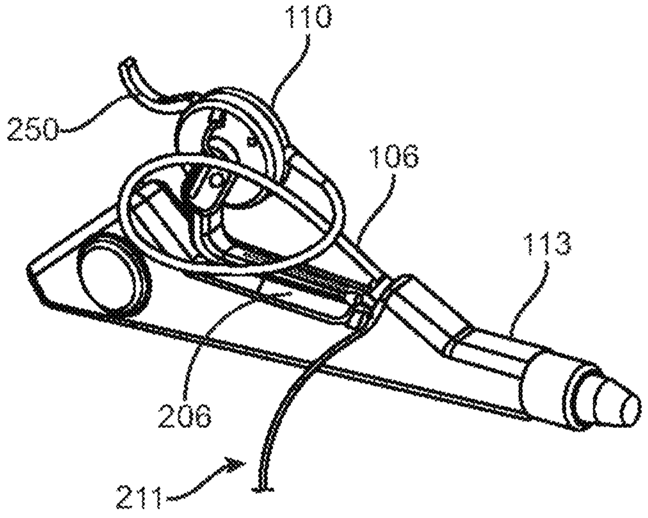
Figure 17:
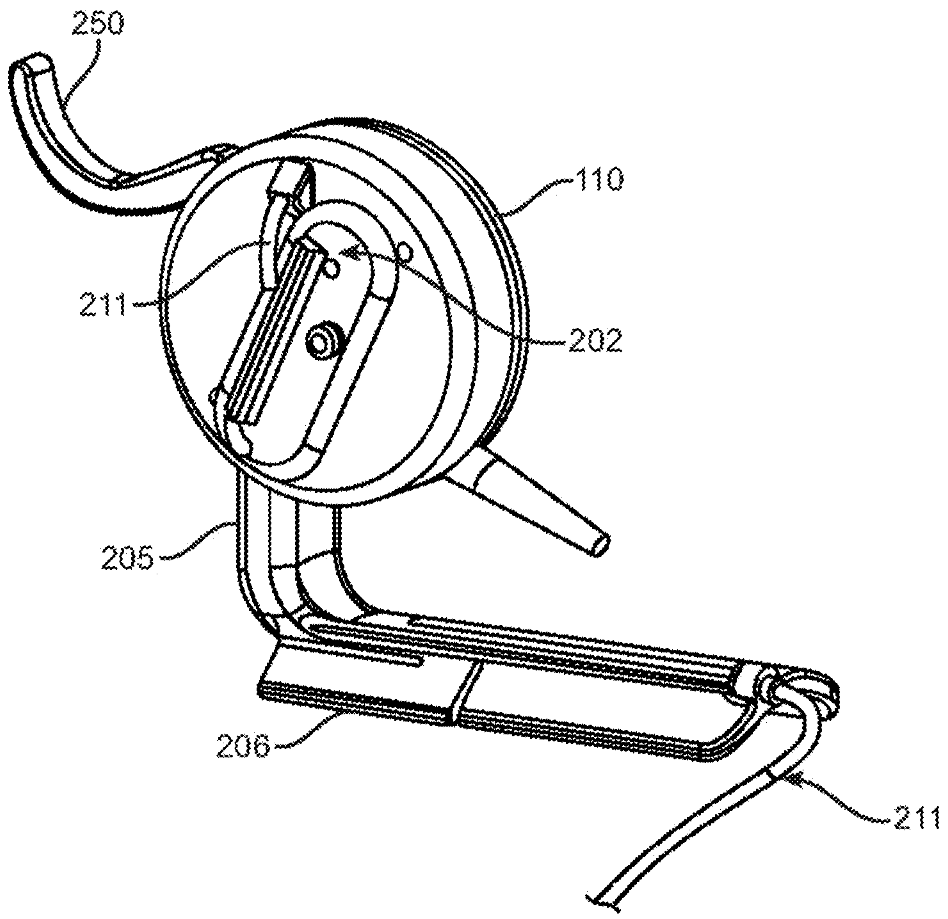

FIGS. 15-17 illustrate another embodiment of a grip device 200. In this embodiment, the grip device 200 comprises a mounting element 202, an arm 205 and a grip saddle 206. Here, the mounting element 202 is configured to receive a handle 110 of a treatment catheter. In this embodiment, the handle 110 has a round or circular shape. In some embodiments the handle 110 is able to rotate in relation to the mounting element 202 and in other embodiments the handle 110 is coupleable to the mounting element 202 and the mounting element is able to rotate in relation to the arm 205. In either case, such rotation allows the handle 110 to move in relation to the grip device 200 and likewise the endoscope upon which the grip device 200 is mounted.

As shown, the grip saddle 206 is disposed upon a side of the handle 113, such as along a contour between a working channel port 115 and a suction port 117. In this embodiment, the grip saddle 206 is contoured to mate with the handle 113, such as having curved edges which curve around the handle 113 to assist in securing its positioning. Such positioning of the grip device 200 allows the shaft 106 of the catheter 102 to be inserted into the working channel port 115 of the bronchoscope 112, as shown. Thus, the shaft 106 is able to be advanced or retracted within the working channel by moving the handle 110 or by manipulating the shaft 106 directly, such as with the other hand of the user. In this embodiment, the handle 110 also includes an energy delivery body manipulation mechanism 132 comprising a trigger actuator 250. In this embodiment, the trigger actuator 250 has an arc shape configured for resting one or more fingers thereon. Depression of the trigger actuator 250 causes expansion the energy delivery body 108.

Referring to FIG. 16, in some embodiments, the grip device 200 includes a power cable 211 that can be used to deliver energy to, for example, the mounting element 202 and/or handle 110 of the treatment catheter 102. Thus, various manipulation mechanisms can be electrically controlled or assisted rather than mechanically operated. In this embodiment, the power cable 211 is attached to the grip saddle 206 and runs through the arm 205 up to the handle 110. FIG. 17 provides a closer view of the grip device 200, separate from the endoscope and the treatment catheter.

Figure 18:
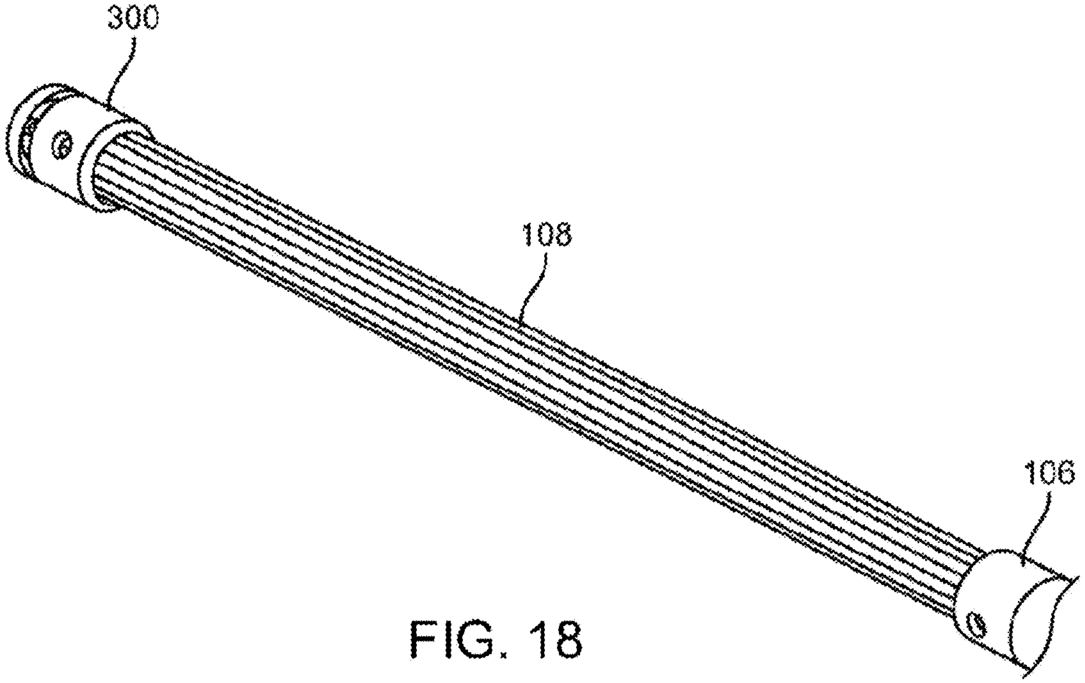
FIG. 18 illustrates an embodiment of a treatment catheter having an embodiment of a flushing tip disposed along its distal end.
Figure 19A:
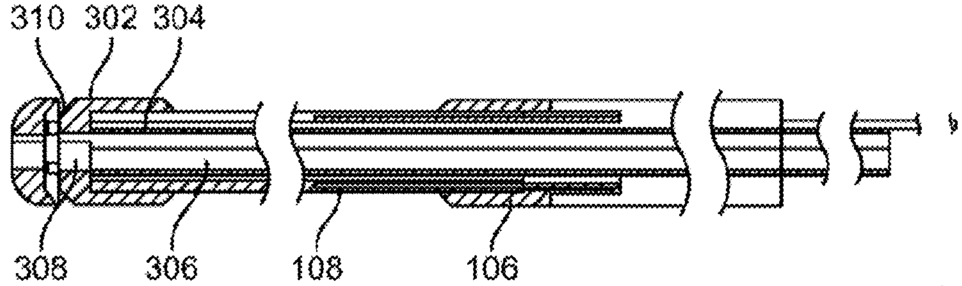
FIG. 19A illustrates the embodiment of FIG. 18 in cross-section.
Figure 19B:
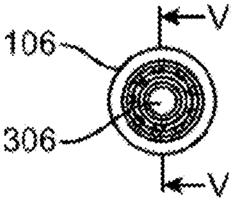
FIG. 19B provides a cross-sectional view of FIG. 18A.

It may be appreciated that the energy delivery body 108 is often positioned in a lung passageway that has excess mucus. Such excess mucus can become problematic in terms of obscuring view through the bronchoscope 112 and/or clogging features of the bronchoscope 112 or treatment catheter 102, such as portions of the energy delivery body 108. In some embodiments, the catheter 102 includes a flushing mechanism to allow fluid to flush out mucus and other debris from devices used in the treatment. FIG. 18 illustrates an embodiment of a treatment catheter 102 having an embodiment of a flushing tip 300 disposed along its distal end. Here the energy delivery body 108 is illustrated in its collapsed configuration and the flushing tip 300 is disposed distal to the energy delivery body 108. In this embodiment, the flushing tip 300 comprises a cylindrical cap 302. FIG. 19A illustrates the embodiment of FIG. 18 in cross-section. As shown, the cylindrical cap 302 includes an inner cavity 304 that fits over the end of the shaft 106, adjacent to the energy delivery body 108. The shaft 106 includes an inner lumen 306 for fluid delivery therethrough. The inner lumen 306 passes into a receptacle 308 in the cap 302 which is fluidly connected with a slot 310 that forces the fluid radially outwardly so as to exit the cap 302. The slot 310 is contoured having an angle directing the fluid backwards, toward the energy delivery body 108 and the proximal end of the shaft 106. FIG. 19B provides a cross-sectional view of FIG. 19A.

Figure 20A:
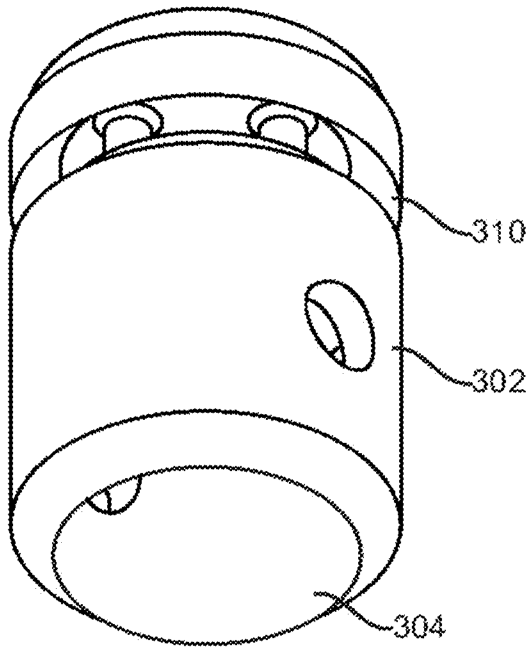
FIGS. 20A-20B provide a closeup view of an embodiment of a cylindrical cap.
Figure 20B:
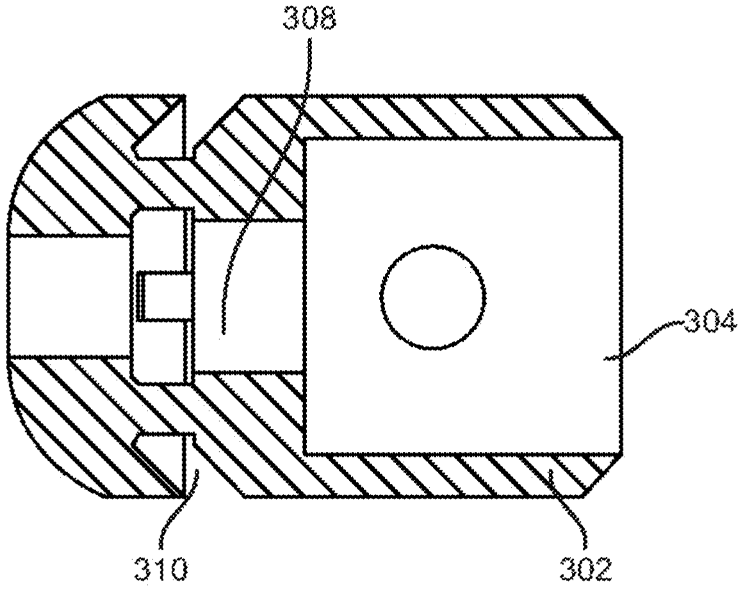

FIGS. 20A-20B provides a closeup view of this embodiment of the cylindrical cap 302. FIG. 20A provides a perspective view of the embodiment of the cylindrical cap 302 and FIG. 20B provides a cross-sectional view of the embodiment of the cylindrical cap 302. As shown, the cap 302 has an inner cavity 304 that receives the shaft 106. This allows fluid from lumen 306 in the shaft 106 to enter the receptable 308 and the slot 310 which directs the fluid radially outwardly so as to exit the cap 302. As shown, the slot 310 is contoured having an angle directing the fluid backwards, toward the energy delivery body 108 and the shaft 106. This allows the fluid to flush the energy delivery body 108 and/or flush the distal tip of the bronchoscope 112 through which it is protruding. The tip of the bronchoscope 112 typically includes an objective lens, one or more light guides and an instrument or working channel through which the catheter 102 is advanced. Mucus from the lung can obscure or clog any of these features. Mucus obscuring the lens interferes with visualization of the procedure. Therefore, as needed, the catheter 102 can be flushed wherein fluid exiting the flushing tip 300 is directed toward the face of the bronchoscope distal tip thereby cleaning its surfaces and removing the excess mucus. This can clean the lens and improve or restore visualization. Likewise, such flushing may reduce the transfer of mucus and other bodily fluids from one portion of the lung to another.

It may be appreciated that the fluid may be directed at a variety of locations by a change in shape of the slot 310. In particular, the slot includes a lip that extends radially outwardly at an angle relative to the longitudinal axis of the shaft 106. A larger angle directs the fluid in the proximal direction at a wider radius from the longitudinal axis than a smaller angle. The angle can be optimized for particular target locations. Likewise, the flowrate of the fluid may be optimized for particular uses.

The therapeutic energy delivery catheter 102 is connectable with the generator 104 along with a dispersive (return) electrode 140 applied externally to the skin of the patient P. Thus, in some embodiments, monopolar energy delivery is achieved by supplying energy between the energy delivery body 108 disposed near the distal end of the catheter 102 and the return electrode 140. It may be appreciated that bipolar energy delivery and other arrangements may alternatively be used. In this embodiment, the generator 104 includes a user interface 150, one or more energy delivery algorithms 152, a processor 154, a data storage/retrieval unit 156 (such as a memory and/or database), and an energy-storage sub-system 158 which generates and stores the energy to be delivered. In some embodiments, one or more capacitors are used for energy storage/delivery, but as new technology is developed any suitable element may be used. In addition, one or more communication ports are included.

It may be appreciated that in some embodiments, the generator 104 is comprised of three sub-systems; 1) a high energy storage system, 2) a high voltage, medium frequency switching amplifier, and 3) the system control, firmware, and user interface. The system controller includes a cardiac synchronization trigger monitor that allows for synchronizing the pulsed energy output to the patient's cardiac rhythm. The generator takes in AC (alternating current) mains to power multiple DC (direct current) power supplies. The generator's controller instructs the DC power supplies to charge a high-energy capacitor storage bank before energy delivery is initiated. At the initiation of therapeutic energy delivery, the generator's controller, high-energy storage banks and a bi-phasic pulse amplifier operate simultaneously to create a high-voltage, medium frequency output.

The processor 154 can be, for example, a general-purpose processor, a field programmable gate array (FPGA), an application specific integrated circuit (ASIC), a digital signal processor (DSP), and/or the like. The processor 154 can be configured to run and/or execute application processes and/or other modules, processes and/or functions associated with the system 100, and/or a network associated with the system 100.

As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a FPGA, an ASIC, a DSP) and/or software-based module (e.g., a module of computer code stored in memory and/or executed at the processor) capable of performing one or more specific functions associated with that module.

The data storage/retrieval unit 156 can be, for example, a random access memory (RAM), a memory buffer, a hard drive, a database, an erasable programmable read-only memory (EPROM), an electrically erasable read-only memory (EEPROM), a read-only memory (ROM), flash memory, and/or so forth. The data storage/retrieval unit 156 can store instructions to cause the processor 154 to execute modules, processes and/or functions associated with the system 100.

Some embodiments the data storage/retrieval unit 156 comprises a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In some embodiments, the system 100 can be communicably coupled to a network, which can be any type of network such as, for example, a local area network (LAN), a wide area network (WAN), a virtual network, a telecommunications network, a data network, and/or the Internet, implemented as a wired network and/or a wireless network. In some embodiments, any or all communications can be secured using any suitable type and/or method of secure communication (e.g., secure sockets layer (SSL)) and/or encryption. In other embodiments, any or all communications can be unsecured.

The user interface 150 can include a touch screen and/or more traditional buttons to allow for the operator to enter patient data, select a treatment algorithm (i.e. energy delivery algorithm 152), initiate energy delivery, view records stored on the storage/retrieval unit 156, or otherwise communicate with the generator 104.

Any of the systems disclosed herein can include a user interface 150 configured to allow operator-defined inputs. The operator-defined inputs can include duration of energy delivery or other timing aspects of the energy delivery pulse, power, target temperature, mode of operation, or a combination thereof. For example, various modes of operation can include system initiation and self-test, operator input, algorithm selection, pre-treatment system status and feedback, energy delivery, post energy delivery display or feedback, treatment data review and/or download, software update, or a combination thereof.

In some embodiments, the system 100 also includes a mechanism for acquiring an electrocardiogram (ECG), such as an external cardiac monitor 170. Example cardiac monitors are available from AccuSync Medical Research Corporation. In some embodiments, the external cardiac monitor 170 is operatively connected to the generator 104 Here, the cardiac monitor 170 is used to continuously acquire the ECG. External electrodes 172 may be applied to the patient P and to acquire the ECG. The generator 104 analyzes one or more cardiac cycles and identifies the beginning of a time period where it is safe to apply energy to the patient P, thus providing the ability to synchronize energy delivery with the cardiac cycle. In some embodiments, this time period is within milliseconds of the R wave to avoid induction of an arrhythmia which may occur if the energy pulse is delivered on a T wave. It may be appreciated that such cardiac synchronization is typically utilized when using monopolar energy delivery, however it may be utilized in other instances.

In some embodiments, the processor 154, among other activities, modifies and/or switches between the energy-delivery algorithms, monitors the energy delivery and any sensor data, and reacts to monitored data via a feedback loop. It may be appreciated that in some embodiments the processor 154 is configured to execute one or more algorithms for running a feedback control loop based on one or more measured system parameters (e.g., current), one or more measured tissue parameters (e.g., impedance), and/or a combination thereof. In these embodiments, the sensing of signals to gather data can be provided by using the energy delivery body, or dedicated, energetically-isolated sensors located on or near the energy delivery body.

The data storage/retrieval unit 156 stores data related to the treatments delivered and can optionally be downloaded by connecting a device (e.g., a laptop or thumb drive) to a communication port. In some embodiments, the device has local software used to direct the download of information, such as, for example, instructions stored on the data storage/retrieval unit 156 and executable by the processor 154. In some embodiments, the user interface 150 allows for the operator to select to download data to a device and/or system such as, but not limited to, a computer device, a tablet, a mobile device, a server, a workstation, a cloud computing apparatus/system, and/or the like. The communication ports, which can permit wired and/or wireless connectivity, can allow for data download, as just described but also for data upload such as uploading a custom algorithm or providing a software update.

As described herein, a variety of energy delivery algorithms 152 are programmable, or can be pre-programmed, into the generator 104, such as stored in memory or data storage/retrieval unit 156. Alternatively, energy delivery algorithms can be added into the data storage/retrieval unit to be executed by processor 154. Each of these algorithms 152 may be executed by the processor 154. Examples algorithms will be described in detail herein below. In some embodiments, the catheter 102 includes one or more sensors 160 that can be used to determine temperature, impedance, resistance, capacitance, conductivity, permittivity, and/or conductance, to name a few. Sensor data can be used to plan the therapy, monitor the therapy and/or provide direct feedback via the processor 154, which can then alter the energy-delivery algorithm 152. For example, impedance measurements can be used to determine not only the initial dose to be applied but can also be used to determine the need for further treatment, or not.

It may be appreciated that any of the systems disclosed herein can include an automated treatment delivery algorithm that could dynamically respond and adjust and/or terminate treatment in response to inputs such as temperature, impedance, treatment duration or other timing aspects of the energy delivery pulse, treatment power and/or system status.

In some embodiments, imaging is achieved with the use of a commercially-available system, such as a bronchoscope 112 connected with a separate imaging screen 180. It may be appreciated that imaging modalities can be incorporated into the catheter 102 or used alongside or in conjunction with the catheter 102. The imaging modality can be mechanically, operatively, and/or communicatively coupled to the catheter 102 using any suitable mechanism.

Figure 21:
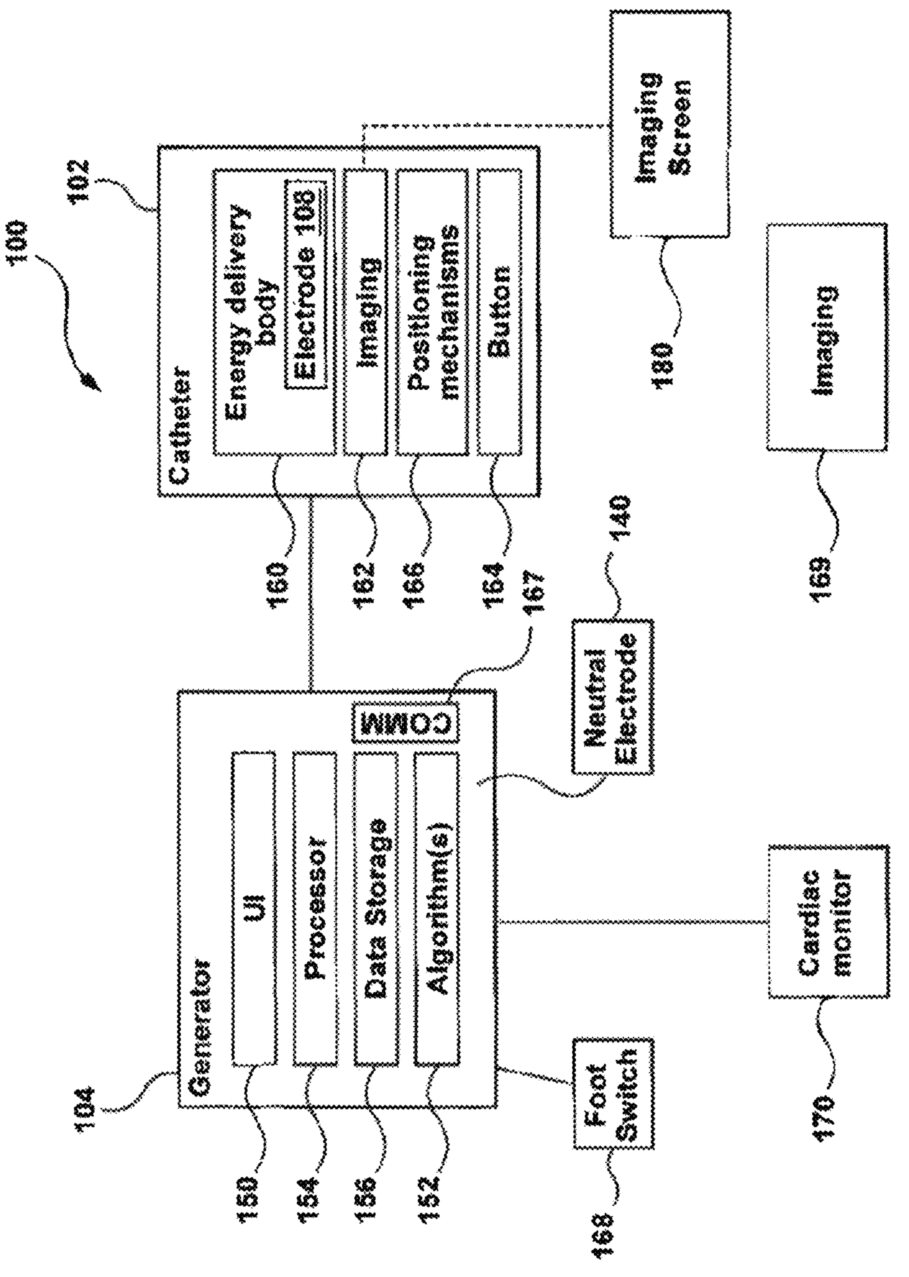
FIG. 21 is a schematic illustration of an embodiment of a pulmonary tissue modification system.

FIG. 21 is a schematic illustration of an embodiment of a pulmonary tissue modification system 100. In this embodiment, the catheter 102 is configured for monopolar energy delivery. As shown, a dispersive (neutral) or return electrode 140 is operatively connected to the generator 104 while affixed to the patient's skin to provide a return path for the energy delivered via the catheter 102. The energy-delivery catheter 102 includes one or more energy delivery bodies 108 (comprised of electrode(s)), one or more sensors 160, one or more imaging modalities 162, one or more buttons 164, and/or positioning mechanisms 166 (e.g., such as, but not limited to, levers and/or dials on a handle with pull wires, telescoping tubes, a sheath, and/or the like) the one or more energy delivery bodies 108 into contact with the tissue. In some embodiments, a foot switch 168 is operatively connected to the generator 104 and used to initiate energy delivery.

As mentioned previously, the user interface 150 can include a touch screen and/or more traditional buttons to allow for the operator to enter patient data, select a treatment algorithm 152, initiate energy delivery, view records stored on the storage/retrieval unit 156, or otherwise communicate with the generator 104. The processor 154 manages and executes the energy-delivery algorithm, monitors the energy delivery and any sensor data, and reacts to monitored data via a feedback loop. The data storage/retrieval unit 156 stores data related to the treatments delivered and can be downloaded by connecting a device (e.g., a laptop or thumb drive) to a communication port 167.

The catheter 102 is operatively connected to the generator 104 and/or a separate imaging screen 180. Imaging modalities 162 can be incorporated into the catheter 102 or used alongside or in conjunction with the catheter 102. Alternatively or in addition, a separate imaging modality or apparatus 169 can be used, such as a commercially-available system (e.g., a bronchoscope). The separate imaging apparatus 169 can be mechanically, operatively, and/or communicatively coupled to the catheter 102 using any suitable mechanism.

Figure 22A:
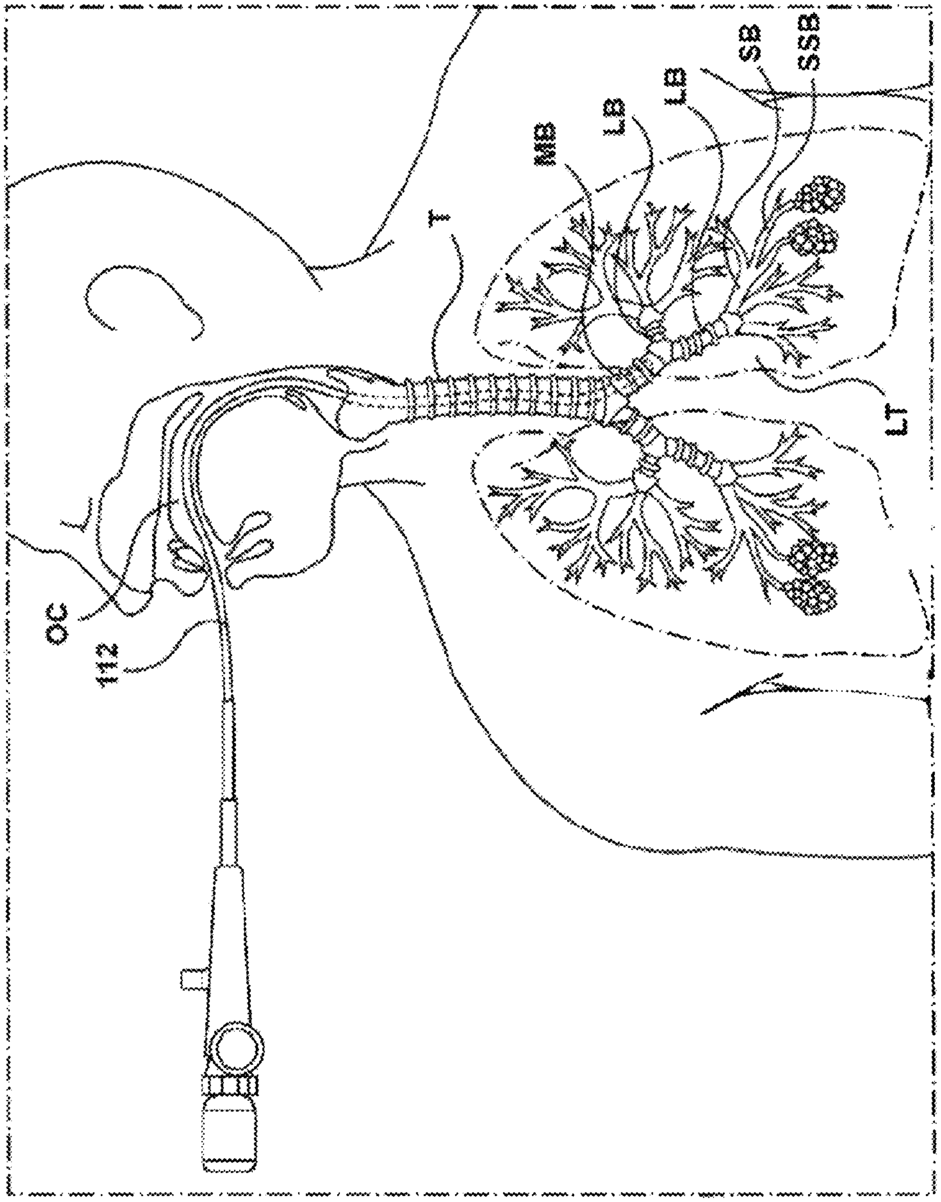
FIGS. 22A-22B illustrate a bronchoscope inserted in the mouth/oral cavity of the patient and the nose/nasal cavity of the patient, respectively.
Figure 22B:
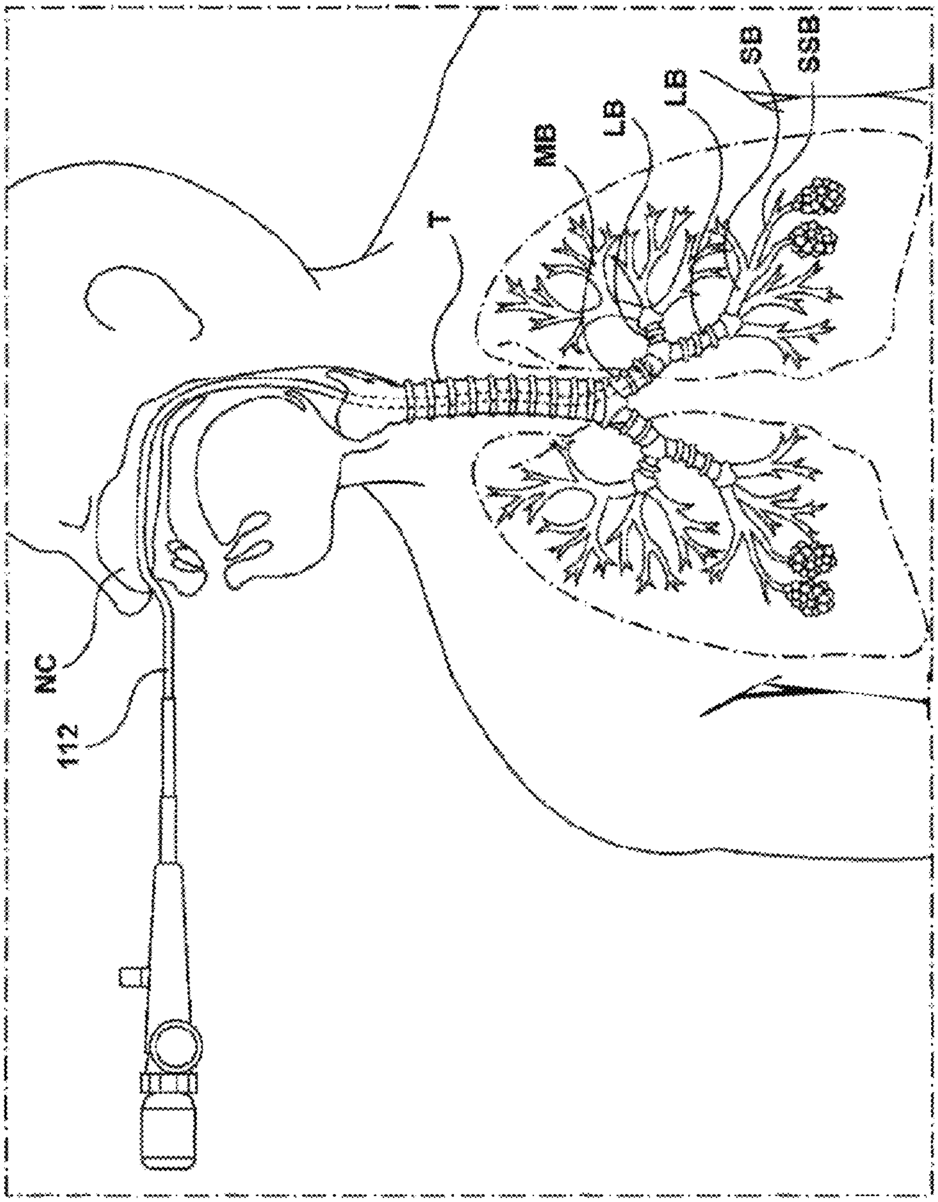

Referring to FIG. 22A, a bronchoscope 112 is inserted in the mouth or oral cavity OC of the patient P. It may be appreciated that methods for accessing the airway can include use of other natural orifices such as the nose or nasal cavity NC. Alternatively, a suitable artificial orifice may be used (not shown e.g., stoma, tracheotomy). Use of the bronchoscope 112 allows for direct visualization of the target tissues and the working channel of the bronchoscope 112 can be used to deliver the catheter 102 as per the apparatuses and systems disclosed herein, allowing for visual confirmation of catheter placement and deployment. FIGS. 22A-22B illustrate advancement of the distal end of the catheter 102 into the trachea T and the mainstem bronchi MB, though it may be appreciated that the catheter 102 may be advanced into the lobar bronchi LB, more distal segmental bronchi SB and sub-segmental bronchi SSB if desired.

Figure 23:
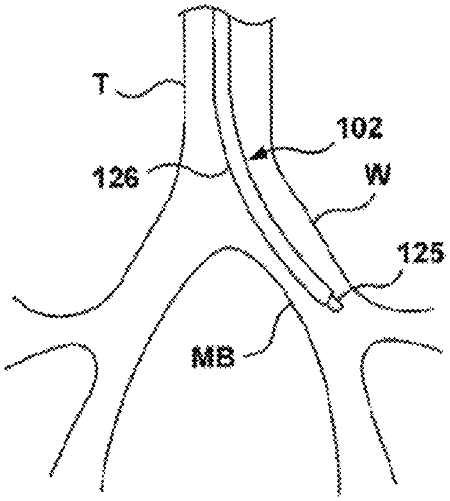
FIGS. 23, 24, 25 illustrate positioning of the distal end of the catheter into the mainstem bronchi for treatment of the airway.
Figure 24:
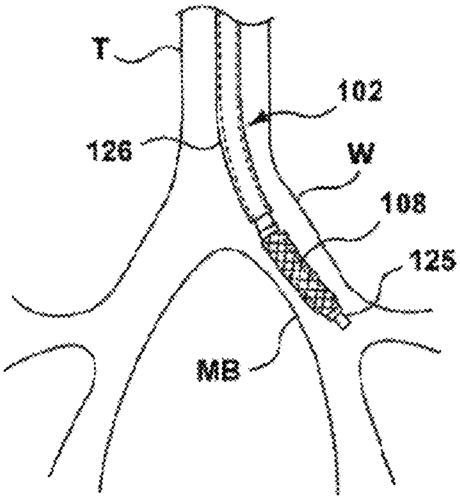
Figure 25:
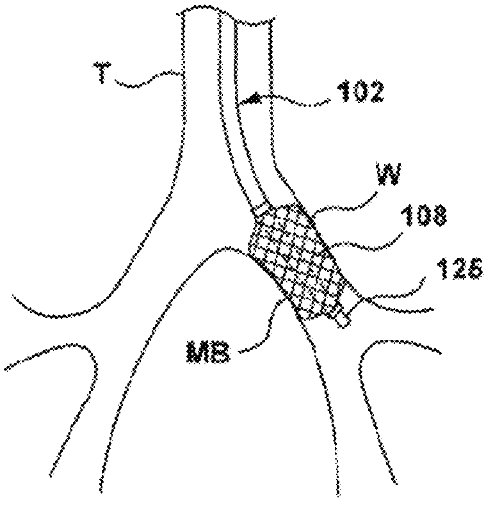

FIGS. 23-25 illustrate positioning of the distal end of the catheter 102 into the mainstem bronchi MB for treatment of the airway. In some embodiments, the catheter 102 has an atraumatic tip 125 to allow advancement through the airways without damaging or the airway walls W. FIG. 23 illustrates the catheter 102 advanced into the mainstem bronchi MB while the sheath 126 is covering the energy delivery body 108. Positioning of the catheter 102 may be assisted by various imaging techniques. For example, the bronchoscope 112 may be used to provide real-time direct visual guidance to the target site and may be used to observe accurate positioning of the catheter 102 before, during and after the delivery of treatment. FIG. 24 illustrates withdrawal of the sheath 126, exposing the energy delivery body 108. It may be appreciated that in some embodiments, the energy delivery body 108 is self-expanding so that the sheath 126 holds the energy delivery body 108 in a collapsed configuration. In such embodiments, withdrawal of the sheath 126 releases the energy delivery body 108, allowing self-expansion. In other embodiments, the energy delivery body 108 is expanded by other mechanisms, such as movement of the knob 132, which may occur after the sheath 126 is withdrawn. FIG. 25 illustrates the basket-shaped energy delivery body 108 in an expanded configuration, wherein the energy delivery body 108 contacts the airway walls W. Additional imaging can be used to verify positioning and/or make additional measurements (e.g., depth).

Once the energy delivery body 108 is desirably positioned, treatment energy is provided to the airway wall W by the energy delivery body 108. The treatment energy is applied according to at least one energy delivery algorithm.

In some embodiments, the user interface 150 on the generator 104 is used to select the desired treatment algorithm 152. In other embodiments, the algorithm 152 is automatically selected by the generator 104 based upon information obtained by one or more sensors on the catheter 102, which will be described in more detail in later sections. A variety of energy delivery algorithms may be used. In some embodiments, the algorithm 152 generates a signal having a waveform comprising a series of energy packets with rest periods between each packet, wherein each energy packet comprises a series of high voltage pulses. In some embodiments, each high voltage pulse is between about 500 V to 10 kV, or about 500 V to about 5,000 V, including all values and subranges in between. In some embodiments, the energy provided is within the frequency range of about 10 kHz to about 10 MHz, or about 100 kHz to about 1 MHz, including all values and subranges in between.

The algorithm 152 delivers energy to the walls of the airway so as to provide the desired treatment with minimal or no tissue heating. In some embodiments, a temperature sensor is used to measure electrode and/or tissue temperature during treatment to ensure that energy deposited in the tissue does not result in any clinically significant tissue heating. For example, a temperature sensor can monitor the temperature of the tissue and/or electrode, and if a predefined threshold temperature is exceeded (e.g., 65° C.), the generator can alter the algorithm to automatically cease energy delivery or modify the algorithm to reduce temperature to below the pre-set threshold. For example, if the temperature exceeds 65° C., the generator can reduce the pulse width or increase the time between pulses and/or packets in an effort to reduce further cumulative temperature rise. This can occur in a pre-defined step-wise approach, as a percentage of the parameter, or by other methods.

In some embodiments, the generator has several fixed algorithm settings whereby the targeted cell depth is reflected in each setting. For instance, when treating a lung passageway, one setting/algorithm may primarily affect the pathogens resident in the mucus layer, another setting/algorithm may target the epithelium, another setting/algorithm may primarily target the epithelium, basement membrane, submucosa and/or smooth muscle, while yet another setting/algorithm may primarily target the epithelium, basement membrane, submucosa, smooth muscle, submucosal glands and/or nerves. In some embodiments, treatment is performed at the same location, but in others, the operator may choose to affect certain cell types at different locations. The setting utilized by the operator may be dependent on the physiologic nature of the patient's condition.

II. Energy Delivery Algorithms

As mentioned previously, one or more energy delivery algorithms 152 are programmable, or can be pre-programmed, into the generator 104 for delivery to the patient P. The one or more energy delivery algorithms 152 specify electric signals which provide energy delivered to the airway walls W which are non-thermal (e.g. below a threshold for thermal ablation; below a threshold for inducing coagulative thermal damage), reducing or avoiding inflammation, and preventing denaturation of stromal proteins. In general, the algorithm 152 is tailored to affect tissue to a pre-determined depth and/or to target specific types of cellular responses to the energy delivered. It may be appreciated that depth and/or targeting may be affected by parameters of the energy signal prescribed by the one or more energy delivery algorithms 152, the design of the catheter 102 (particularly the one or more energy delivery bodies 108), and/or the choice of monopolar or bipolar energy delivery. In some instances, bipolar energy delivery allows for the use of a lower voltage to achieve the treatment effect, as compared to monopolar energy delivery. In a bipolar configuration, the positive and negative poles are close enough together to provide a treatment effect both at the electrode poles and in-between the electrode poles. This can concentrate the treatment effect over a specific tissue area thus involving a lower voltage to achieve the treatment effect compared to monopolar. Likewise, this focal capability using lower voltages, may be used to reduce the depth of penetration, such as to affect the epithelial cells rather than the submucosal cells. In other instances, this reduced effect penetration depth may be used to focus the energy such as to target epithelial and submucosal layers, while sparing the deeper cartilage tissue. In addition, lower voltage requirements may obviate the use of cardiac synchronization if the delivered voltage is low enough to avoid stimulation of the cardiac muscle cells.

It may be appreciated that a variety of energy delivery algorithms 152 may be used. In some embodiments, the algorithm 152 prescribes a signal having a waveform comprising a series of energy packets wherein each energy packet comprises a series of high voltage pulses. In such embodiments, the algorithm 152 specifies parameters of the signal such as energy amplitude (e.g., voltage) and duration of applied energy, which is comprised of the number of packets, number of pulses within a packet, and the fundamental frequency of the pulse sequence, to name a few. Additional parameters may include switch time between polarities in biphasic pulses, dead time between biphasic cycles, and rest time between packets, which will be described in more detail in later sections. There may be a fixed rest period between packets, or packets may be gated to the cardiac cycle and are thus variable with the patient's heart rate. There may be a deliberate, varying rest period algorithm or no rest period may also be applied between packets. A feedback loop based on sensor information and an auto-shutoff specification, and/or the like, may be included.

Figure 26:
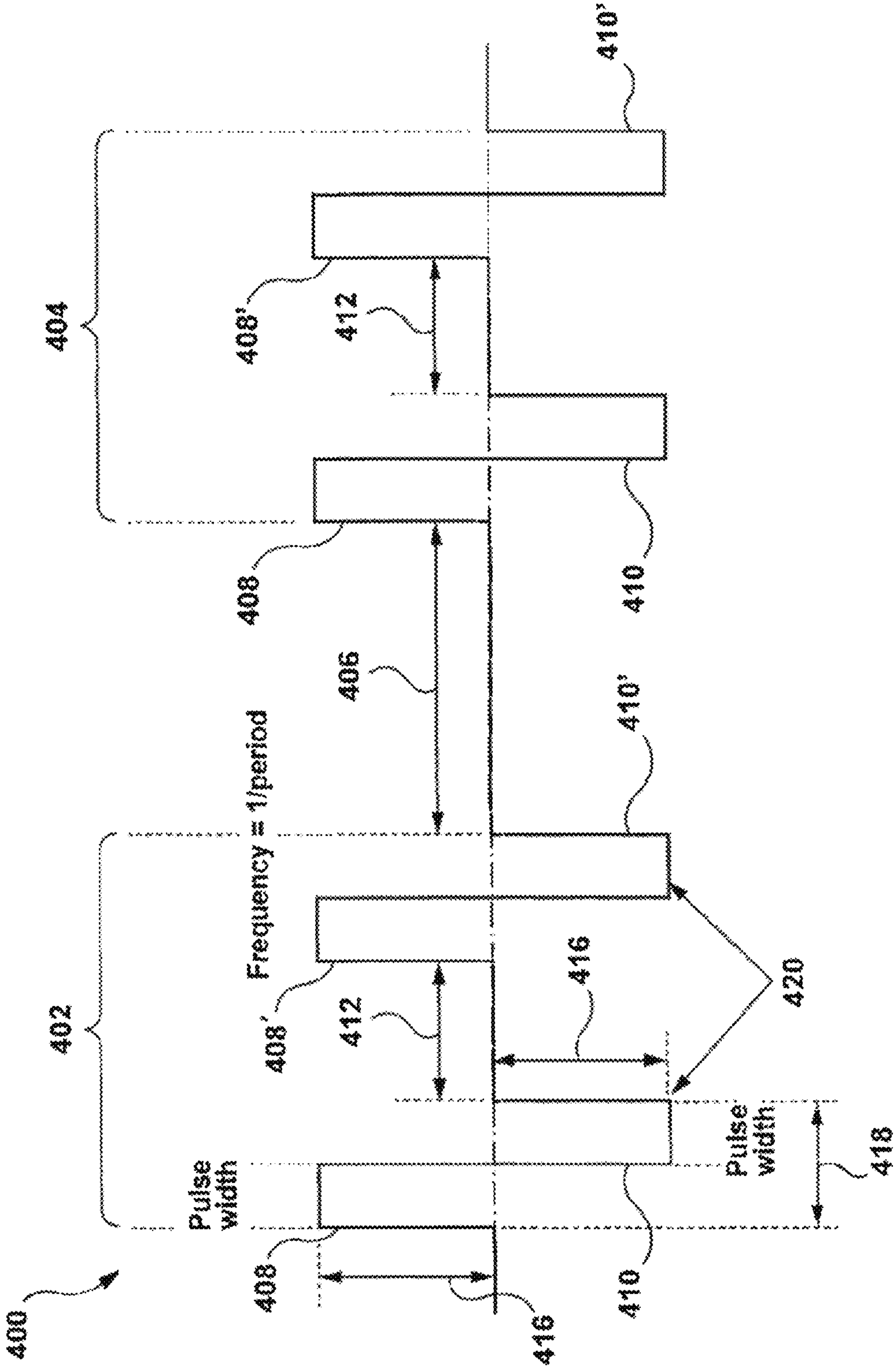
FIG. 26 illustrates an embodiment of a waveform of a signal prescribed by an energy delivery algorithm.

FIG. 26 illustrates an embodiment of a waveform 400 of a signal prescribed by an energy delivery algorithm 152. Here, two packets are shown, a first packet 402 and a second packet 404, wherein the packets 402, 404 are separated by a rest period 406. In this embodiment, each packet 402, 404 is comprised of a first biphasic cycle (comprising a first positive pulse peak 408 and a first negative pulse peak 410) and a second biphasic cycle (comprising a second positive pulse peak 408' and a second negative pulse peak 410'). The first and second biphasic pulses are separated by dead time 412 (i.e., a pause) between each pulse. In this embodiment, the biphasic pulses are symmetric so that the set voltage 416 is the same for the positive and negative peaks. Here, the biphasic, symmetric waves are also square waves such that the magnitude and time of the positive voltage wave is approximately equal to the magnitude and time of the negative voltage wave. When using a bipolar configuration, portions of the airway wall W cells facing the negative voltage wave undergo cellular depolarization in these regions, where a normally negatively charged cell membrane region briefly turns positive. Conversely, portions of the airway wall W cells facing the positive voltage wave undergo hyperpolarization in which the cell membrane region's electric potential becomes extremely negative. It may be appreciated that in each positive or negative phase of the biphasic pulse, portions of the airway wall W cells will experience the opposite effects. For example, portions of cell membranes facing the negative voltage will experience depolarization, while the portions 180° to this portion will experience hyperpolarization. In some embodiments, the hyperpolarized portion faces the dispersive or return electrode 140.

A. Voltage

The voltages used and considered may be the tops of square-waveforms, may be the peaks in sinusoidal or sawtooth waveforms, or may be the RMS voltage of sinusoidal or sawtooth waveforms. In some embodiments, the energy is delivered in a monopolar fashion and each high voltage pulse or the set voltage 416 is between about 500 V to 10,000 V, particularly about 500 V to 5000 V, about 500 V to 4000 V, about 1000 V to 4000 V, about 2500 V to 4000V, about 2000 to 3500, about 2000 V to 2500V, about 2500 V to 3500 V, including all values and subranges in between including about 500 V, 1000 V, 1500 V, 2000 V, 2500 V, 3000 V, 3500 V, 4000 V. In some embodiments, each high voltage pulse is in range of approximately 1000 V to 2500 V which can penetrate the airway wall W in particular parameter combinations so as to treat or affect particular cells somewhat shallowly, such as epithelial cells. In some embodiments, each high voltage pulse is in the range of approximately 2500 V to 4000 V which can penetrate the airway W in particular parameter combinations so as to treat or affect particular cells somewhat deeply positioned, such as submucosal cells or smooth muscle cells.

It may be appreciated that the set voltage 416 may vary depending on whether the energy is delivered in a monopolar or bipolar fashion. In bipolar delivery, a lower voltage may be used due to the smaller, more directed electric field. In some embodiments, the energy is delivered in a bipolar fashion and each pulse is in the range of approximately 100 V to 1900 V, particularly 100 V to 999 V, more particularly approximately 500 V to 800 V, such as 500 V, 550 V, 600 V, 650 V, 700 V, 750 V, 800 V. In other embodiments, the energy is delivered in a bipolar fashion and each pulse is between approximately 50 and 5000 volts, including 250 to 1500 volts.

The bipolar voltage selected for use in therapy is dependent on the separation distance of the electrodes, whereas the monopolar electrode configurations that use a distant dispersive pad electrode may be delivered with less consideration for exact placement of the catheter electrode and dispersive electrode placed on the body. In monopolar electrode embodiments, larger voltages are typically used due to the dispersive behavior of the delivered energy through the body to reach the dispersive electrode, on the order of 10 cm to 100 cm effective separation distance. Conversely, in bipolar electrode configurations, the relatively close active regions of the electrodes, on the order of 0.5 mm to 10 cm, including 1 mm to 1 cm, results in a greater influence on electrical energy concentration and effective dose delivered to the tissue from the separation distance. For instance, if the targeted voltage-to-distance ratio is 3000 V/cm to evoke the desired clinical effect at the appropriate tissue depth (1.3 mm), if the separation distance is changed from 1 mm to 1.2 mm, this would result in a necessary increase in treatment voltage from 300 to about 360 V, a change of 20%.

B. Frequency

The number of biphasic cycles per second of time is the frequency. In some embodiments, biphasic pulses are utilized to reduce undesired muscle stimulation, particularly cardiac muscle stimulation. In other embodiments, the pulse waveform is monophasic, and there is no clear inherent frequency, and instead a fundamental frequency may be considered by doubling the monophasic pulse length to derive the frequency. In some embodiments, the signal has a frequency in the range 100 kHz-1 MHz, more particularly 100 kHz-1000 kHz. In some embodiments, the signal has a frequency in the range of approximately 100-600 kHz which typically penetrates the airway W so as to treat or affect particular cells somewhat deeply positioned, such as submucosal cells or smooth muscle cells. In some embodiments, the signal has a frequency in range of approximately 600 kHz-1000 kHz or 600 kHz-1 MHz which typically penetrates the airway wall W so as to treat or affect particular cells somewhat shallowly, such as epithelial cells. It may be appreciated that at some voltages, frequencies at or below 300 kHz may cause undesired muscle stimulation. Therefore, in some embodiments, the signal has a frequency in the range of 400-800 kHz or 500-800 kHz, such as 500 kHz, 550 kHz, 600 kHz, 650 kHz, 700 kHz, 750 kHz, 800 kHz. In particular, in some embodiments, the signal has a frequency of 600 kHz. In addition, cardiac synchronization is typically utilized to reduce or avoid undesired cardiac muscle stimulation during sensitive rhythm periods. It may be appreciated that even higher frequencies may be used with components which minimize signal artifacts.

C. Voltage-Frequency Balancing

The frequency of the waveform delivered may vary relative to the treatment voltage in synchrony to retain adequate treatment effect. Such synergistic changes would include the decrease in frequency, which evokes a stronger effect, combined with a decrease in voltage, which evokes a weaker effect. For instance, in some cases the treatment may be delivered using 3000 V in a monopolar fashion with a waveform frequency of 800 kHz, while in other cases the treatment may be delivered using 2000 V with a waveform frequency of 400 kHz.

When used in opposing directions, the treatment parameters may be manipulated in a way that makes it too effective, which may increase muscle contraction likelihood or risk effects to undesirable tissues, such as cartilage for airway treatments. For instance, if the frequency is increased and the voltage is decreased, such as the use of 2000 V at 800 kHz, the treatment may not have sufficient clinical therapeutic benefit. Opposingly, if the voltage was increased to 3000 V and frequency decreased to 400 kHz, there may be undesirable treatment effect extent to cartilage tissues or other collateral sensitive tissues. In some cases, the over-treatment of these undesired tissues could result in morbidity or safety concerns for the patient.

D. Packets

As mentioned, the algorithm 152 prescribes a signal having a waveform comprising a series of energy packets wherein each energy packet comprises a series of high voltage pulses. The cycle count 420 is half the number of pulses within each biphasic packet. Referring to FIG. 26, the first packet 402 has a cycle count 420 of two (i.e. four biphasic pulses). In some embodiments, the cycle count 420 is set between 1 and 100 per packet, including all values and subranges in between. In some embodiments, the cycle count 420 is up to 5 pulses, up to 10 pulses, up to 25 pulses, up to 40 pulses, up to 60 pulses, up to 80 pulses, up to 100 pulses, up to 1,000 pulses or up to 2,000 pulses, including all values and subranges in between.

The packet duration is determined by the cycle count. The higher the cycle count, the longer the packet duration and the larger the quantity of energy delivered. In some embodiments, packet durations are in the range of approximately 50 to 100 microseconds, such as 50 μs, 60 μs, 70 μs, 80 μs, 90 μs or 100 μs. In other embodiments, the packet durations are in the range of approximately 100 to 1000 microseconds, such as 150 μs, 200 μs, 250 μs, 500 μs, or 1000 μs.

The number of packets delivered during treatment, or packet count, may include 1 packet, 2 packets, 3 packets, 4 packets, 5 packets, 10 packets, 15 packets, 20 packets, 50 packets, 100 packets, 1,000 packets, up to 5 packets, up to 10 packets, up to 15 packets, up to 20 packets, up to 100 packets, or up to 1000 packets, including all values and subranges in between. In some embodiments, 5 packets are delivered, wherein each packet has a packet duration of 100 microseconds and a set voltage of 2500 V. In some embodiments, 5 to 10 packets are delivered, wherein each packet has a packet duration of 100 microseconds and a set voltage of 2500 V, which results in a treatment effect that has increased intensity and uniformity. In some embodiments, less than 20 packets, wherein each packet has a packet duration of 100 microseconds and a set voltage of 2500 V, are delivered to avoid affecting the cartilage layer CL. In some embodiments, a total energy-delivery duration between 0.5 to 100 milliseconds at a set voltage of 2500 V can be optimal for the treatment effect.

E. Rest Period

In some embodiments, the time between packets, referred to as the rest period 406, is set between about 0.1 seconds and about 5 seconds, including all values and subranges in between. In other embodiments, the rest period 406 ranges from about 0.001 seconds to about 10 seconds, including all values and subranges in between. In some embodiments, the rest period 406 is approximately 1 second. In particular, in some embodiments the signal is synced with the cardiac rhythm so that each packet is delivered synchronously within a designated period relative to the heartbeats, thus the rest periods coincide with the heartbeats. In other embodiments wherein cardiac synchronization is utilized, the rest period 406 may vary, as the rest period between the packets can be influenced by cardiac synchronization, as will be described in later sections.

F. Switch Time and Dead Time

A switch time is a delay or period of no energy that is delivered between the positive and negative peaks of a biphasic pulse. In some embodiments, the switch time ranges between about 0 to about 1 microsecond, including all values and subranges in between. In other embodiments, the switch time ranges between 1 and 20 microseconds, including all values and subranges in between.

Delays may also be interjected between each cycle of the biphasic pulses, referred as "dead-time". Dead time occurs within a packet, but between biphasic pulses. This is in contrast to rest periods which occur between packets. In some embodiments, the dead time 412 is set between about 0 and about 500 nanoseconds, including 0 to 20 microseconds, including all values and subranges in between. In other embodiments, the dead time 412 is in a range of approximately 0 to 10 microseconds, or about 0 to about 100 microseconds, or about 0 to about 100 milliseconds, including all values and subranges in between. In some embodiments, the dead time 412 is in the range of 0.2 to 0.3 microseconds. Dead time may also be used to define a period between separate, monophasic, pulses within a packet.

Delays, such as switch times and dead times, are introduced to a packet to reduce the effects of biphasic cancellation within the waveform. Biphasic cancellation or bipolar cancellation is a term used to refer to the reduced induction of cellular modulation in response to biphasic waveforms versus monophasic waveforms, particularly when switch times and dead times are small, such as below 10 μs. One explanation for this phenomenon is provided here, though it may be appreciated that there are likely other biological, physical, or electrical characteristics or alterations that result in the reduced modulation from biphasic waveforms. When cells are exposed to the electromotive force induced by the electric field presence, there is electrokinetic movement of ions and solutes within the intracellular and extracellular fluids. These charges accumulate at dielectric boundaries such as cell and organelle membranes, altering the resting transmembrane potentials (TMPs). When the electric field is removed, the driving force that generated the manipulated TMPs is also eliminated, and the normal biotransport and ionic kinetics operating with concentration gradients begin to restore normative distributions of the solutes. This induces a logarithmic decay of the manipulated TMP on the membranes. However, if rather than eliminating the electric field, the electric field polarity is retained but with a reversed polarity, then there is a new electromotive force actively eliminating the existing TMP that was induced, followed by the accumulation of a TMP in the opposite polarity. This active depletion of the initially manipulated TMP considerably restricts the downstream effects cascade that may occur to the cell, weakening the treatment effect from the initial electric field exposure. Further, where the subsequent electric field with reversed polarity must first "undo" the original TMP manipulation generated, and then begin accumulating its own TMP in the opposite polarity; the final TMP reached by the second phase of the electric field is not as strong as the original TMP, assuming identical durations of each phase of the cycle. This reduces the treatment effects generated from each phase of the waveform resulting in a lower treatment effect than that generated by either pulse in the cycle would achieve alone. This phenomenon is referred as biphasic cancellation. For packets with many cycles, this pattern is repeated over the entire set of cycles and phase changes within the cycles for the packet. This dramatically limits the effect from the treatment. When cell behavior is modulated as a result of the pulsed electric fields by mechanisms other than purely transmembrane potential manipulation, it may be appreciated that the effects of biphasic cancellation are less pronounced, and thus the influence of switch times and dead times on treatment outcome are reduced.

Thus, in some embodiments, the influence of biphasic cancellation is reduced by introducing switch time delays and dead time. In some instances, the switch time and dead time are both increased together to strengthen the effect. In other instances, only switch time or only dead time are increased to induce this effect.

It may be appreciated that typically appropriate timing is for the relaxation of the TMP to complete after 5× the charging time-constant, t. For most cells, the time constant may be approximated as 1 μs. Thus, in some embodiments the switch time and the dead time are both set to at least 5 μs to eliminate biphasic cancellation. In other embodiments, the reduction in biphasic cancellation may not require complete cell relaxation prior to reversing the polarity, and thus the switch time and the dead time are both set at 0.5 μs to 2 μs. In other embodiments, the switch time and the dead time are set to be the same length as the individual pulse lengths, since further increases in these delays may only offer diminishing returns in terms of increased treatment effect and the collateral increase in muscle contraction. In this way, the combination of longer-scale pulse durations (>500 ns) and stacked pulse cycles with substantial switch time and dead time delays, it is possible to use biphasic waveforms without the considerably reduced treatment effect that occurs due to biphasic cancellation. In some cases, the tuning of these parameters may be performed to evoke stronger treatment effects without a comparably proportional increase in muscle contraction. For example, using 600 kHz waveform with switch time=dead time=1.66 μs (2× the duration as the pulses), may be used to retain the reduction in muscle contraction versus monophasic pulse waveforms, but with the retention of stronger treatment effects.

In some embodiments, the switch time duration is adjusted such that the degree of therapy effect relative to distant cell effects is optimized for the target of the therapy. In some embodiments, the switch time duration is minimized to decrease distant muscle cell contractions, with lesser local therapy effect. In other embodiments, the switch time duration is extended to increase the local therapy effect, with potential additional distant muscle cell contractions. In some embodiments, the switch time or dead time duration are extended to increase the local therapy effect, and the use of neuromuscular paralytics are employed to control the resulting increase in muscle contraction. In some embodiments, switch time duration is 10 ns to 2 μs, while in other embodiments, the switch time duration is 2 μs to 20 μs. In some instances, when cell modulation is targeted in a way where transmembrane potential manipulation is not the primary mechanism needed to evoke the targeted treatment effects, the switch time and dead time delays are minimized to less than 0.1 μs or to 0 μs. This elimination of delays minimizes the peripheral, non-targeted treatment effects such as skeletal muscle contraction or cardiac muscle action potential and contraction, but will not alter the treatment effect intensity at the targeted site.

Another benefit of utilizing switch time and the dead time delays to increase treatment effects for biphasic waveforms is a reduction in generator demands, whereby the introduction of pauses will enable stronger treatment effects without requiring asymmetric/unbalanced pulse waveforms. In this case, unbalanced waveforms are described as those that are monophasic, or have an unbalanced duration or voltage or combination in one polarity relative to the other. In some cases, unbalanced means that the integral of the positive portions of the waveform are not equal to the integral of the negative portions of the waveform. Generators capable of delivering unbalanced waveforms have a separate set of design considerations that are accounted for thereby increasing potential generator complexity.

Energy delivery may be actuated by a variety of mechanisms, such as with the use of a button 164 on the catheter 102 or a foot switch 168 operatively connected to the generator 104. Such actuation typically provides a single energy dose. The energy dose is defined by the number of packets delivered and the voltage of the packets. Each energy dose delivered to the airway wall W maintains the temperature at or in the wall W below a threshold for thermal ablation, particularly thermal ablation of the basement membrane BM which comprises denaturing stromal proteins in the basement membrane or deeper submucosal extracellular protein matrices. In addition, the doses may be titrated or moderated over time so as to further reduce or eliminate thermal build up during the treatment procedure. Instead of inducing thermal damage, defined as protein coagulation, the energy dose provide energy at a level which induces biological mechanisms and cellular effects which ultimately lead to the regeneration of healthy tissue.

III. Catheter Embodiments

A variety of energy delivery catheter 102 embodiments are envisioned. Characteristics and features described herein can be used in any combination to achieve the desired tissue effects. Typically, such catheters 102 are sized and configured to treat lung passageways having a lumen diameter of approximately 3-20 mm. Typically, energy delivery bodies 108 expand within the lung passageway lumen so as to reside near, against, in contact, or exerting pressure or force against the wall W of the lumen. In some embodiments, the energy delivery body 108 expands to a diameter of up to 22 mm, particularly 3-20 mm or 3-22 mm.

It may be appreciated that the systems, methods and devices described herein may include a variety of variations, particularly various types of energy delivery bodies 108 and treatment methods. Example variations are described and illustrated in commonly assigned patent applications including international patent application number PCT/US2017/039527 titled "GENERATOR AND A CATHETER WITH AN ELECTRODE AND A METHOD FOR TREATING A LUNG PASSAGEWAY" which claims priority to U.S. provisional application Nos. 62/355,164 and 62/489,753, PCT/US2018/067504 titled "OPTIMIZATION OF ENERGY DELIVERY FOR VARIOUS APPLICATIONS" which claims priority to U.S. provisional application Nos. 62/610,430 and 62/693,622, and international patent application number PCT/US2020/028844 titled "DEVICES, SYSTEMS AND METHODS FOR THE TREATMENT OF ABNORMAL TISSUE" which claims priority to U.S. provisional application No. 62/835,846, each of which are incorporated by reference for all purposes. It may be appreciated that such designs are sized and configured to be used in the appropriate portion of the respiratory anatomy.

It may be appreciated that although the embodiments described herein primarily focus on treating lung conditions, such devices, systems and methods are not so limited. A variety of conditions may be treated with the devices, systems and methods described herein, typically involving introduction of a treatment catheter endoluminally to a body lumen. Thus, the devices and systems may be used with all types of endoscopes, not limited to bronchoscopes. Example endoscopes include anoscopes, arthroscopes, bronchoscopes, colonoscopes, colposcopes, cystoscopes, esophagoscopes, gastroscopes, laparoscopes, laryngoscopes, neuroendoscopes, proctoscopes, sigmoidoscopes, and thoracoscopes, to name a few.

As used herein, the terms "about" and/or "approximately" when used in conjunction with numerical values and/or ranges generally refer to those numerical values and/or ranges near to a recited numerical value and/or range. In some instances, the terms "about" and "approximately" can mean within ±10% of the recited value. For example, in some instances, "about 100 [units]" can mean within ±10% of 100 (e.g., from 90 to 110). The terms "about" and "approximately" can be used interchangeably.

While preferred embodiments have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments described herein may be employed in practice.

What is claimed is:

1. A grip device for mating a handle of a treatment catheter with an endoscope handle of an endoscope, comprising:

a mounting element configured to mate with the handle of the treatment catheter, wherein the treatment catheter includes a shaft coupled with the handle and configured to be advanced through a working channel port of the endoscope; and a grip saddle configured to mate with the endoscope handle so that movement of the endoscope handle moves the mated handle of the treatment catheter in unison while the shaft is independently advanceable through the working channel port of the endoscope.

2. The grip device of claim 1, wherein the grip saddle is shaped to conform to a portion of the endoscope handle.

3. The grip device of claim 2, wherein the portion of the endoscope handle resides between a suction port and the working channel port.

4. The grip device of claim 2, wherein the mounting element is coupled to an arm that holds the mounting element at a distance from the grip saddle.

5. The grip device of claim 4, wherein the distance is sufficient to allow at least a hand to be inserted between the mounting element and the grip saddle.

6. The grip device of claim 4, wherein the mounting element is coupled to the arm by a joint connection which allows the mounting element to rotate in relation to the arm.

7. The grip device of claim 6, wherein the joint connection allows the mounting element to rotate forward and/or backward.

8. The grip device of claim 6, wherein the joint connection allows the mounting element to rotate left and/or right.

9. The grip device of claim 6, wherein the joint connection comprises a pivot joint.

10. The grip device of claim 6, wherein the joint connection allows the mounting element to rotate in all directions.

11. The grip device of claim 1, wherein the mounting element is configured to slidably mate with the handle of the treatment catheter.

12. The grip device of claim 1, wherein the handle of the treatment catheter includes one or more mechanisms for manipulating the treatment catheter, and wherein the mounting element is configured so that the one or more mechanisms is manipulatable by a hand while simultaneously holding the grip saddle against the endoscope handle with the hand.

13. The grip device of claim 12, wherein the treatment catheter comprises an energy delivery body, and wherein manipulation of the one or more mechanisms affects the energy delivery body.

14. The grip device of claim 13, wherein the energy delivery body comprises an expandable structure, and wherein manipulation of the one or more mechanisms expands and/or contracts the expandable structure.

15. The grip device of claim 14, wherein the one or more mechanisms is coupled to the expandable structure by a planetary gear train.

16. The grip device of claim 1, further comprising at least one attachment mechanism configured to attach the grip saddle to the endoscope handle.

17. The grip device of claim 1, wherein the treatment catheter comprises an energy delivery body comprising an expandable basket-shaped electrode.

18. The grip device of claim 1, wherein the endoscope comprises a bronchoscope.

19. A system for treating a patient with the use of an endoscope having an endoscope handle, comprising:

a treatment catheter having a distal end and a proximal end, wherein the treatment catheter includes a handle near the proximal end and a shaft extending toward the distal end, and wherein the shaft is configured to be advanced through a working channel port of the endoscope; and a grip device configured to mate with the handle of the treatment catheter and the endoscope handle so that movement of the endoscope handle moves the handle of the treatment catheter in unison and so that the shaft is independently advanceable through the working channel port of the endoscope.

20. The system of claim 19, wherein:

the treatment catheter comprises an energy delivery body disposed along the distal end, the shaft comprises a longitudinal axis and a lumen, the handle comprises at least one manipulation mechanism configured to manipulate the energy delivery body so as to contact a lung passageway of the patient in a manner that transposes mucus to the energy delivery body, and further comprising:

a cap having a slot, wherein the cap is disposed at the distal end of the treatment catheter so that the lumen of the shaft is fluidly connected with the slot, and wherein the slot is contoured so that fluid flowing through the lumen is directed through the slot to an outside of the shaft at an angle that directs the fluid toward the energy delivery body in a manner that removes at least a portion of the mucus from the energy delivery body.

* * * * *